United States Patent
Málnási-Csizmadia et al.

(10) Patent No.: US 11,746,112 B2
(45) Date of Patent: Sep. 5, 2023

(54) PHARMACEUTICALLY EFFECTIVE COMPOUNDS INHIBITING SELECTIVELY THE MYOSIN 2 ISOFORMS

(71) Applicants: PRINTNET KERESKEDELMI ÉS SZOLGÁLTATÓ KFT., Veresegyház (HU); EÖTVÖS LORÁND TUDOMÁNYEGYETEM, Budapest (HU)

(72) Inventors: András Málnási-Csizmadia, Budapest (HU); Maté Gyimesi, Budapest (HU); András Szabó, Budapest (HU); Péter Hári, Veresegyház (HU); Suthar Sharad Kumar, Budapest (HU); Mihály Kovács, Kecskemét (HU); Ádám István Horváth, Balatonfüred (HU); Máté Pénzes, Budapest (HU); István Lörincz, Budapest (HU); László Végner, Budapest (HU); Zoltán Simon, Oroszlány (HU); Sándor Bátori, Budapest (HU); Zoltán Szönyegi, Budapest (HU); Vajk Horváth, Budapest (HU); József Répási, Érd (HU)

(73) Assignees: EÖTVÖS LORÁND TUDOMÁNYEGYETEM, Budapest (HU); PRINTNET KERESKEDELMI ÉS SZOLGÁLTATÓ KFT., Veresegyház (HU)

( * ) Notice: Subject to any disclaimer, the term of this patent is extended or adjusted under 35 U.S.C. 154(b) by 0 days.

(21) Appl. No.: 17/048,206

(22) PCT Filed: Apr. 18, 2019

(86) PCT No.: PCT/HU2019/050017
§ 371 (c)(1),
(2) Date: Oct. 16, 2020

(87) PCT Pub. No.: WO2019/202346
PCT Pub. Date: Oct. 24, 2019

(65) Prior Publication Data
US 2021/0087201 A1 Mar. 25, 2021

(30) Foreign Application Priority Data
Apr. 18, 2018 (HU) .................... P1800129

(51) Int. Cl.
*C07D 487/14* (2006.01)
(52) U.S. Cl.
CPC .................. *C07D 487/14* (2013.01)
(58) Field of Classification Search
CPC .................................................. C07D 487/14
USPC ....................................................... 514/183
See application file for complete search history.

(56) References Cited

U.S. PATENT DOCUMENTS

| | | | |
|---|---|---|---|
| 9,492,441 B2 | 11/2016 | Disanto |
| 9,827,238 B2 | 11/2017 | Disanto |
| 9,943,512 B2 | 4/2018 | Disanto |
| 10,858,357 B2 | 12/2020 | Lenkei et al. |
| 11,091,464 B2 | 8/2021 | Hunt et al. |
| 2011/0190270 A1 | 8/2011 | Jackson et al. |
| 2013/0071927 A1 | 3/2013 | Lu et al. |
| 2016/0030482 A1 | 2/2016 | Van Den Bos et al. |
| 2017/0020861 A1 | 1/2017 | Disanto |
| 2017/0129886 A1 | 5/2017 | Disanto et al. |
| 2021/0060012 A1 | 3/2021 | Russell et al. |

FOREIGN PATENT DOCUMENTS

| | | |
|---|---|---|
| EA | 23580 B1 | 6/2016 |
| EP | 2 777 703 | 9/2014 |
| JP | 63-500518 A | 2/1988 |
| WO | WO-2009/094718 | 8/2009 |
| WO | WO-2010/120785 | 10/2010 |

(Continued)

OTHER PUBLICATIONS

King, Med. Chem., Principle and Practice (1994), pp. 206-208.*

(Continued)

*Primary Examiner* — Taofiq A Solola
(74) *Attorney, Agent, or Firm* — Cooley LLP

(57) ABSTRACT

The present invention relates to compounds of formula (I) or (II)

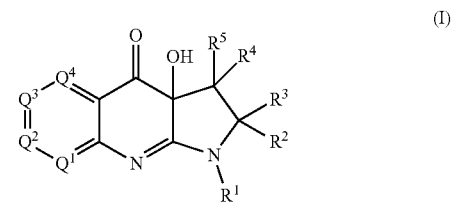

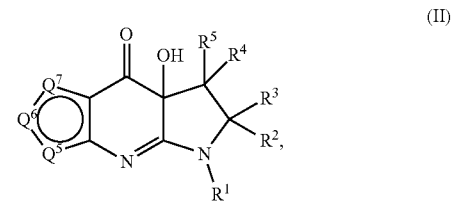

pharmaceutically acceptable salts, solvates, tautomers, stereoisomers thereof, including enantiomers, diastereomers, racemic mixtures, mixtures of enantiomers, or combinations thereof, and pharmaceutical uses of the compounds.

23 Claims, 1 Drawing Sheet

(56) References Cited

FOREIGN PATENT DOCUMENTS

| WO | WO-2012/113555 | | 8/2012 |
|---|---|---|---|
| WO | WO-2012/158942 | | 11/2012 |
| WO | WO-2016/161192 | | 10/2016 |
| WO | WO-2016/180918 | | 11/2016 |
| WO | 2017/129782 | A1 * | 8/2017 |
| WO | WO-2017/129782 | A1 | 8/2017 |
| WO | WO-2019/164852 | A1 | 8/2019 |
| WO | WO-2019/241469 | A1 | 12/2019 |

OTHER PUBLICATIONS

Bastin R.J. et al.: "Salt selection and optimisation procedures for pharmaceutical new chemical entities", Organic Process Research & Development, 2000, V. 4, N. 5, p. 427-435.
Farman et al "Blebbistatin: use as inhibitor of muscle contraction" 2008 Eur J Physiol, doi: 10.1007/s00424-007-0375-3.
Heissler, S. et al. (2013). Nonmuscle myosin-2: mix and match. Cellular and molecular life sciences, 70(1), pp. 1-21.
International Search Report and Written Opinion of the International Searching Authority dated Nov. 11, 2019, for PCT Application No. PCT/HU2019/050017, filed on Apr. 18, 2019, 9 pages.
Kepiro, M. et al. (2014). para-Nitroblebbistatin, the Non-Cytotoxic and Photostable Myosin II Inhibitor, Angew. Chem. Int. Ed. 53:8211-8215.
Kepiro, M. et al. (2014). Para-Nitroblebbistatin, the non-cytotoxic and photostable myosin II inhibitor, Angewandte Chemie, International Edition, vol. 53, No. 31, pp. 8350-8354.
Kneussel, M. et al. (2013). Myosin motors at neuronal synapses: drivers of membrane transport and actin dynamics. Nature Reviews Neuroscience, 14(4), 233-247.
Lima, L.M. (2005). Bioisosterism: A Useful Strategy for Molecular Modification and Drug Design, Curr. Medin. Chem. 12:23-49.
Lucas-Lopez et al. Org Biomol Chem. Jun. 21, 2008;6(12):2076-84. doi: 10.1039/b801223g.
Lucas-Lopez, C. et al. (2005). Absolute Stereochemical Assignment and Fluorescence Tuning of the Small Molecule Tool, (−)-Blebbistatin, Eur. J. Org. Chem. 1736-1740.
Ma, X. et al. (2014). The role of vertebrate nonmuscle II in development and human disease. Bioarchitecture 4:88-102.
Moreira Lima et al Curr Med Chem. 2005;12(1):23-49. doi: 10.2174/0929867053363540.
Newell-Litwa, KA. et al. (2015). Non-muscle myosin II in disease: mechanisms and therapeutic opportunities. Disease models & mechanisms, 8(12), 1495-1515.
Pénzes et al.: "Direct myosin-2 inhibition enhances cerebral perfusion resulting in functional improvement after ischemic stroke" Theranostics, 2020, 10(12) 5341-5356.
Pinniger et al 2005 J Muscle Res Cell Motil, 10.1007/s10974-005-2679-2.
Rauscher et al.: "Targeting Myosin by Blebbistatin Derivatives: Optimization and Pharmacological Potential" Trends in Biochemical Sciences, Sep. 2018, 43(9), 700-713.
Verhasselt, S. et al. (2017). Discovery of (S)-3'-hydroxyblebbistatin and (S)-3'-aminoblebbistatin: polar myosin II inhibitors with superior research tool properties, Org. Biomol. Chem. 15:2104-2118.
Verhasselt, S. et al. (2017). Improved synthesis and comparative analysis of the tool properties of new and existing D-ring modified (S)-blebbistatin analogs, Europe J. Medicinal Chem. 136:85-103.
Verhasselt, S. et al. (2017). Insights into the myosin II inhibitory potency of A-ring-modified (S)-blebbistatin analogs, Bioorg. Medicinal Chem. Letters 27:2986-2989.
Vicente-Manzamares, M. et al. (2009). Non-muscle myosin II takes centre stage in cell adhesion and migration, Nature Reviews Molecular Cell Biology 10(11):778-790.
Wang et al Biochem Soc Trans. Distinct and redundant roles of the non-muscle myosin II isoforms and functional domains Oct. 2011; 39(5): 1131-1135. doi:10.1042/BST0391131.

Wigton, E.J. et al. (2016). Myosin-IIA regulates leukemia engraftment and brain infiltration in a mouse model of acute lymphoblastic leukemia. J. Leukoc. Biol. 100(1):143-15. doi: 10.1189/jlb.1A0815-342R.
Zhai, K. et al. (2015). NMMHC IIA inhibition impedes tissue factor expression and venous thrombosis via Akt/GSKβ-NF-κB signalling pathways in the endothelium. Thromb. Haemost. 114(1):173-185. doi: 10.1160/TH14-10-0880.
Zhang, Y. et al. (2017). The Myosin II Inhibitor, Blebbistatin, Ameliorates FeCl3-induced Arterial Thrombosis via the GSK3β-NF-κB Pathway. Int. J. Biol. Sci. 13(5):630-639. doi: 10.7150/ijbs.18485.
Wang, Y. et al. (2017). Myosin IIA-related Actomyosin Contractility Mediates Oxidative Stress-induced Neuronal Apoptosis. Front. Mol. Neurosci. 10:75. doi: 10.3389/fnmol.2017.00075.
Young, E.J. et al. (2017). Nonmuscle myosin II inhibition disrupts methamphetamine-associated memory in females and adolescents. Neurobiol. Learn. Mem. 139:109-116. doi:10.1016/j.nlm.2017.01.001.
Young, E.J. et al. (2016). Nonmuscle myosin IIB as a therapeutic target for the prevention of relapse to methamphetamine use. Mol. Psychiatry. 21(5):615-623. doi: 10.1038/mp.2015.103.
Doller, A. et al. (2015). The cytoskeletal inhibitors latrunculin A and blebbistatin exert antitumorigenic properties in human hepatocellular carcinoma cells by interfering with intracellular HuR trafficking. Exp. Cell. Res. 330(1):66-80. doi: 10.1016/j.yexcr.2014.09.010.
Tomii, S. et al. (2017). Cortical Actin Alteration at the Matrix-Side Cytoplasm in Lung Adenocarcinoma Cells and Its Significance in Invasion. Pathobiology. 84(4):171-183. doi: 10.1159/000452838.
Southern, B.D. et al. (2016). Matrix-driven Myosin II Mediates the Pro-fibrotic Fibroblast Phenotype. J. Biol. Chem. 291 (12):6083-6095. doi: 10.1074/jbc.M115.712380.
Liu, Z. et al. (2010). Blebbistatin inhibits contraction and accelerates migration in mouse hepatic stellate cells. Br. J. Pharmacol. 159(2):304-315. doi: 10.1111/j.1476-5381.2009.00477.x.
Atluri, K. et al. (2016). Blebbistatin-Loaded Poly(d,l-lactide- coglycolide) Particles for Treating Arthrofibrosis. ACS Biomater. Sci. Eng. 2(7):1097-1107. doi: 10.1021 /acsbiomaterials.6b00082.
Su, Z. et al. (2016). Oxidized Low-Density Lipoprotein-Induced Cyclophilin A Secretion Requires ROCK-Dependent Diphosphorylation of Myosin Light Chain. J. Vasc. Res. 53(3-4):206-215. doi: 10.1159/000449387.
Yoshimoto, T. et al. (2016). Aggregatibacter actinomycetemcomitans outer membrane protein 29 (Omp29) induces TGF-β-regulated apoptosis signal in human gingival epithelial cells via fibronectin/integrinβ1/FAK cascade. Cell. Microbiol. 18(12):1723-1738. doi: 10.1111/cmi.12607.
Jiang, L. et al. (2016). Substrate stiffness of endothelial cells directs LFA-1/ICAM-1 interaction: A physical trigger of immune-related diseases? Clin. Hemorheol. Microcirc. 61(4):633-643. doi: 10.3233/CH-151951.
Cymerys, J. et al. (2016). Function of myosin during entry and egress of equid herpesvirus type 1 in primary murine neurons. Acta Virol. 60(4):410-416. doi: 10.4149/av_2016_04_410.
Ivkovic, S. et al. (2012). Direct inhibition of myosin II effectively blocks glioma invasion in the presence of multiple motogens. Mol. Biol. Cell. 23(4):533-542. doi: 10.1091/mbc.e06-05-0431.
Kolega, J. (2006). The role of myosin II motor activity in distributing myosin asymmetrically and coupling protrusive activity to cell translocation. Mol. Biol. Cell. 17(10):4435-4445. doi: 10.1091/mbc.e06-05-0431.
Guerreo-Valero, M. et al. (2021). Dysregulation of myelin synthesis and actomyosin function underlies aberrant myelin in CMT4B1 neuropathy. Proc. Natl. Acad. Sci. USA. 118(10):e2009469118. doi: 10.1073/pnas.2009469118.
Jun, M.-H. et al. (2020).Nonmuscle myosin IIB regulates Parkinmediated mitophagy associated with amyotrophic lateral sclerosis-linked TDP-43. Cell Death Dis. 11(11):952 doi: 10.1038/s41419-020-03165-7.
Xiao, J.-W. et al. (2015). Acute effects of Rho-kinase inhibitor fasudil on pulmonary arterial hypertension in patients with congenital heart defects. Circ. J. 79(6):1342-1348. doi: 10.1253/circj.CJ-14-1015.

(56) References Cited

OTHER PUBLICATIONS

He, W.-Q. et al. (2011). Role of myosin light chain kinase in regulation of basal blood pressure and maintenance of salt-induced hypertension. Am. J. Physiol. Heart Circ. Physiol. 301(2):H584-591. doi: 10.1152/ajpheart.01212.2010.

Takefuji, M. (2013). RhoGEF-mediated vasoconstriction in hypertension. Hypertens. Res. 36(11):930-931. doi: 10.1038/hr.2013.101.

Qin, B. and Zhou, J. (2015). Src Family Kinases (SFK) Mediate Angiotensin II-Induced Myosin Light Chain Phosphorylation and Hypertension. PLoS One. 10(5):e0127891. doi: 10.1371/journal.pone.0127891.

Han, Y.-J. et al. (2006). Increased myosin light chain kinase expression in hypertension: Regulation by serum response factor via an insertion mutation in the promoter. Mol. Biol. Cell. 17(9):4039-4050. doi: 10.1091/mbc.e06-04-0353.

Sun, J. et al. (2019). CPI-17-mediated contraction of vascular smooth muscle is essential for the development of hypertension in obese mice. J. Genet. Genomics. 46(3):109-118. doi: 10.1016/j.jgg.2019.02.005.

Zhang, X.-H. et al. (2009). In vitro and in vivo relaxation of corpus cavernosum smooth muscle by the selective myosin II inhibitor, blebbistatin. J. Sex. Med. 6(10):2661-2671. doi: 10.1111/j.1743-6109.2009.01424.x.

Morgan, K.G. (2014). The importance of the smooth muscle cytoskeleton to preterm labour. Exp. Physiol. 99(3):525-529. doi: 10.1113/expphysiol.2013.072876.

Roffino, S. et al. (2012). Premature birth is associated with not fully differentiated contractile smooth muscle cells in human umbilical artery. Placenta. 33(6):511-517. doi: 10.1016/j.placenta.2012.03.005.

Zhang, X. et al. (2011). In vitro and in vivo relaxation of urinary bladder smooth muscle by the selective myosin II inhibitor, blebbistatin. BJU Int. 107(2):310-317. doi: 10.1111/j.1464-410X.2010.09366.x.

Wróbel, A. et al. (2019). Blebbistatin, a Myosin II Inhibitor, Exerts Antidepressant-Like Activity and Suppresses Detrusor Overactivity in an Animal Model of Depression Coexisting with Overactive Bladder. Neurotox. Res. 35(1):196-207. doi: 10.1007/s12640-018-9948-5.

Zhang, X. et al. (2011). Blebbistatin, a myosin II inhibitor, as a novel strategy to regulate detrusor contractility in a rat model of partial bladder outlet obstruction. Plos One. 6(10):e25958. doi: 10.1371/journal.pone.0025958.

Kampourakis, T. et al. (2018). Omecamtiv mercabil and blebbistatin modulate cardiac contractility by perturbing the regulatory state of the myosin filament. J. Physiol. 596(1):31-46. doi: 10.1113/JP275050.

Ujfalusi, Z. et al. (2018). Dilated cardiomyopathy myosin mutants have reduced force-generating capacity. J. Biol. Chem. 293(23):9017-9029. doi: 10.1074/jbc.RA118.001938.

Tang, W. et al. (2017). Modulating Beta-Cardiac Myosin Function at the Molecular and Tissue Levels. Front. Physiol. 7:659. doi: 10.3389/fphys.2016.00659.

Day, S.M. et al. (2022). Myosin modulators: emerging approaches for the treatment of cardiomyopathies and heart failure. J. Clin. Invest. 132(5):e148557. doi: 10.1172/JCI148557.

Alsulami, K. and Marston, S. (2020). Small Molecules acting on Myofilaments as Treatments for Heart and Skeletal Muscle Diseases. Int. J. Mol. Sci. 21(24):9599. doi: 10.3390/ijms21249599.

Heitner, S.B. et al. (2019). Mavacamten Treatment for Obstructive Hypertrophic Cardiomyopathy: A Clinical Trial. Ann. Intern. Med. 170(11):741-748. doi: 10.7326/M18-3016.

Olivotto, I. et al. (2020). Mavacamten for treatment of symptomatic obstructive hypertrophic cardiomyopathy (EXPLORER-HCM): a randomised, double-blind, placebo-controlled, phase 3 trial. Lancet. 396(10253):759-769. doi: 10.1016/S0140-6736(20)31792-X.

Tower-Rader, A. et al. (2020). Mavacamten: a novel small molecule modulator of β-cardiac myosin for treatment of hypertrophic cardiomyopathy. Expert Opin. Investig. Drug. 29(11):1171-1178. doi: 10.1080/13543784.2020.1821361.

Green, E.M. et al. (2016). A small-molecule inhibitor of sarcomere contractility suppresses hypertrophic cardiomyopathy in mice. Science. 351(6273):617-621. doi: 10.1126/science.aad3456.

Gyimesi, M. et al. (2021). Improved Inhibitory and Absorption, Distribution, Metabolism, Excretion, and Toxicology (ADMET) Properties of Blebbistatin Derivatives Indicate That Blebbistatin Scaffold is Ideal for drug Development Targeting Myosin-2. J. Pharmacol. Exp. Ther. 376(3):358-373. doi: 10.1124/jpet.120.000167.

Várkuti, B.H. (2016). A highly soluble, non-phototoxic, non-fluorescent blebbistatin derivative. Sci. Rep. 6:26141. doi: 10.1038/srep26141.

Gyimesi, M. et al. (2020). Single Residue Variation in Skeletal Muscle Myosin Enables Direct and Selective Drug Targeting for Spasticity and Muscle Stiffness. Cell. 183(2):335-346.e13. doi: 10.1016/j.cell.2020.08.050.

Maher, C. et al. (2017). Non-specific low back pain. Lancet. 389(10070):736-747. doi: 10.1016/S0140-6736(16)30970-9.

Van Tulder, M.W. et al. (2003). Muscle relaxants for non-specific low back pain. Cochrane Database Syst. Rev. 2003(2):CD004252. doi: 10.1002/14651858.CD004252.

Blake, P. and Burstein, R. (2019). Emerging evidence of occipital nerve compression in unremitting head and neck pain. J. Headache Pain. 20(1):76. doi: 10.1186/s10194-019-1023-y.

Ferreira, J.R. and Souza, R.P. (2012). Botulinum toxin for vaginismus treatment. Pharmacology. 89(5-6):256-259. doi: 10.1159/000337383.

Karp, B.I. et al. (2019). Methodological approaches to botulinum toxin for the treatment of chronic pelvic pain, vaginismus, and vulvar pain disorders. Int. Urogynecol. J. 30(7):1071-1081. doi: 10.1007/s00192-018-3831-z.

Pacik, P.T. (2014). Understanding and treating vaginismus: a multimodal approach. Int. Urogynecol. J. 25(12):1613-1620. doi: 10.1007/S00192-014-2421-y.

Otero-Romero, S. et al. (2016). Pharmacological management of spasticity in multiple sclerosis: Systematic review and consensus paper. Mult. Scler. 22(11):1386-1396. doi: 10.1177/1352458516643600.

Chen, H.-Y. et al. (2016). Treatment of drug-induced seizures. Br. J. Clin. Pharmacol. 81(3):412-419. doi: 10.1111/bcp.12720.

Walker, K.F. and Thornton, J.G. (2016). Tocolysis and preterm labour. Lancet. 387(10033):2068-2070. doi: 10.1016/S0140-6736(16)00590-0.

Mameniškienė, R. and Wolf, P. (2017). Epilepsia partialis continua: A review. Seizure. 44:74-80. doi: 10.1016/j.seizure.2016.10.010.

Lahaie, M.-A. et al. (2010). Vaginismus: a review of the literature on the classification/diagnosis, etiology and treatment. Womens Health (Lond). 6(5):705-19. doi: 10.2217/whe.10.46.

Kwong, F. et al. Mild and Efficient Copper-Catalyzed Amination of Aryl Bromides with Primary Alkylamines. Organic Letters 2003, vol. 5, No. 6, 793-796.

Lawson, C. et al. Application of the copper catalysed N-arylation of amidines in the synthesis of analogues of the chemical tool, blebbistatin. The Royal Society of Chemistry 2011 Chem. Commun., 2011, 47, 1057-1059.

Roman, B. et al. The Medicinal Chemistry and Use of Myosin II Inhibitor (S)-Blebbistatin and Its Derivatives. J. Med. Chem., Just Accepted Manuscript, DOI: 10.1021/acs.jmedchem.8b00503, Publication Date (Web): Jun. 7, 2018 Downloaded from http://pubs.acs.org on Jun. 7, 2018.

Wang, D. et al. An Efficient Copper-Catalyzed Amination of Aryl Halides by Aqueous Ammonia. Adv. Synth. Catal. 2009, 351, 1722-1726. doi: 10.1002/adsc.200900327.

Zhu, D. et al. Efficient copper-catalyzed amination of aryl halides with amines and N H heterocycles using rac-BINOL as ligand. Journal of Molecular Catalysis A: Chemical 256 (2006) 256-260.

Chuang, C. et al., "Discovery of Aficamten (CK-274), a Next-Generation Cardiac Myosin Inhibitor for the Treatment of Hypertrophic Cardiomyopathy," Journal of Medicinal Chemistry, 2021, vol. 64, pp. 14142-14152.

Matthews, Connie P. et al., "Dominant-Negative Activator Protein 1 (TAM67) Targets Cyclooxygenase02 and Osteopontin under

(56) References Cited

OTHER PUBLICATIONS

Conditions in which It Specifically Inhibits Tumorigenesis," Cancer Research, 2007, vol. 67, pp. 2430-2438.

\* cited by examiner

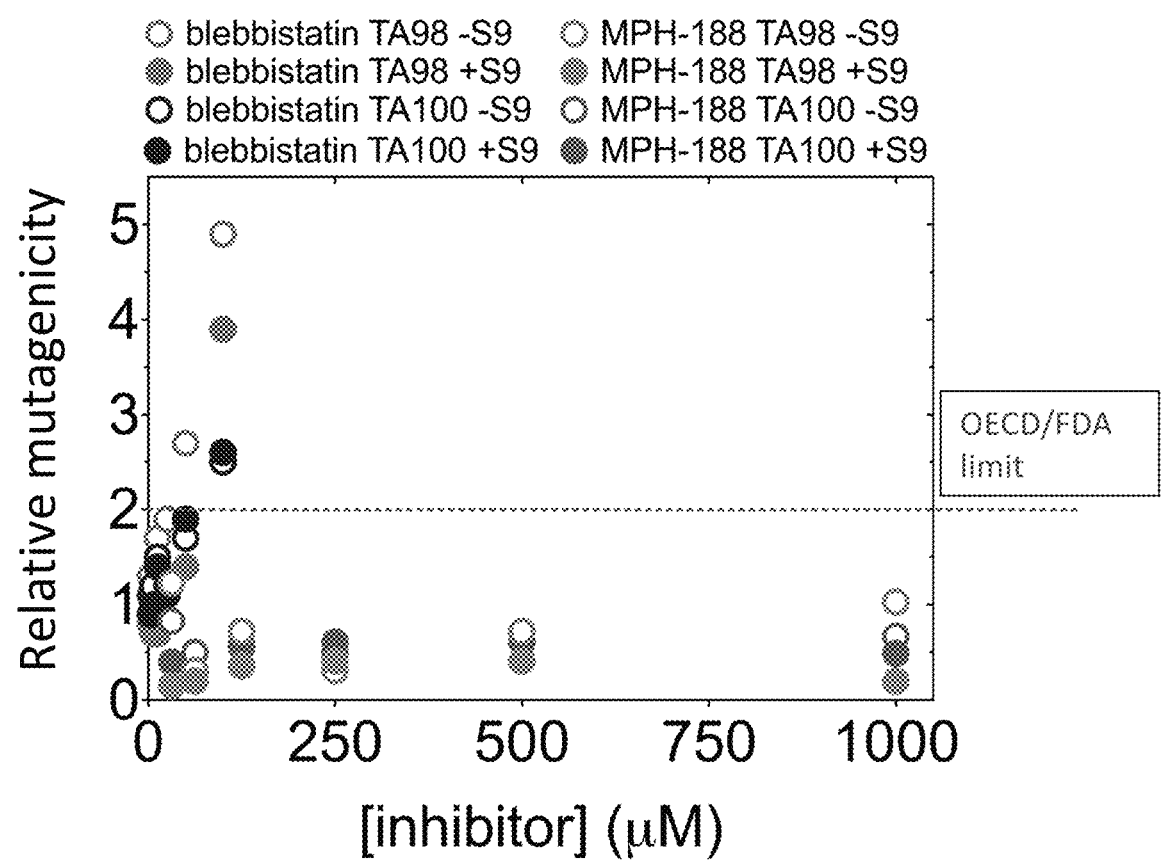

PHARMACEUTICALLY EFFECTIVE COMPOUNDS INHIBITING SELECTIVELY THE MYOSIN 2 ISOFORMS

CROSS-REFERENCE TO RELATED APPLICATIONS

This application is a U.S. National Stage application of International Application PCT/HU2019/050017, filed Apr. 18, 2019, which claims priority to HU P1800129, filed on Apr. 18, 2018, both of which are incorporated herein by reference in their entireties.

The present invention relates to compounds of formula (I) or (II)

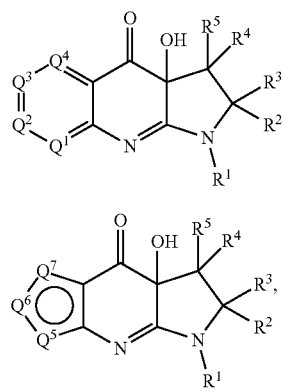

pharmaceutically acceptable salts, solvates, tautomers, stereoisomers thereof, including enantiomers, diastereomers, racemic mixtures, mixtures of enantiomers, or combinations thereof, and pharmaceutical uses of the compounds.

DESCRIPTION OF THE STATE OF THE ART

Isoforms of Myosin 2 and their Occurrence in the Human (Animal) Organism

Myosins are motor proteins present in all eukaryotic cells that use the free enthalpy from the hydrolysis of adenosine triphosphate (AfP) to move along the strands of the actine cell backbone. Myosins are composed of heavy and light chain subunits. The heavy chain is composed of the motor-domain responsible for ATP hydrolytic (ATPase) activity and power generation containing the actin and ATP binding sites; the neck region playing role in the power transmission and control and light chain linking; and a tail region comprising polymerization and effector functions. The superfamily of myosins is classified into more than 30 classes based on the phylogenetic analysis of heavy chain sequences (Sellers, J. R. (1999)). Myosins. John Wiley & Sons Ltd; Coluccio, L. M. (Ed.). (2007). Myosins: a superfamily of molecular motors (Vol. 7). Springer Science & Business Media].

The members of the myosin class 2 are found in all eukaryotic organisms except for the higher plants [Sellers, J. R. (1999). Myosins. John Wiley & Sons Ltd]. Heavy chains of these myosins form dimers that can settle into higher structures called fibers (filaments). The size and dynamics of the fibers within the class show great variation between the individual isoforms (protein variants encoded by different genes). Sarcomeric myosin 2 isoforms in transverse muscles (skeletal muscle, myocardium) constitute the so-called thick filaments. Non-sarcomeric myosin 2 isoforms include smooth muscle and non-muscle myosins (nonmuscle myosin 2, NM2). Non-sarcomeric myosins are filaments capable of reversible polymerization and minifilaments in case of NM2.

The mammalian and human genome contains 15 heavy chain isoforms of myosin (see Table 1). Many isoforms of myosin 2 light chains (a heavy chain binds a so-called essential (ELC) and a so-called regulatory (RLC) light chain) are also known; however, their distribution in the body and function is much less discovered than that of heavy chains. The active substances that are the subject of the present application act through the heavy chain of myosin, therefore we are limited to discussing heavy chain isoforms.

Of the sarcomomeric isoforms, MYH1, MYH2 and MYH4 are the major motor components for skeletal muscles [Coluccio, L. M. (Ed.). (2007). Myosins: a superfamily of molecular motors (Vol. 7). Springer Science & Business Media]. MYH3 is expressed in fetal age, while MYH8 is perinatal. MYH7b also occurs in the heart next to skeletal muscle. MYH13 is found in oculomotor muscles, the function of MYH15 is less discovered, while the MYH16 chewing muscle myosin gene is inactivated in humans. Sarcomeric isoforms also include two human myocardial myosin: MYH6 (alpha-myocardial myosin), is the main protein component of myocardium in the heart atrium, while MYH7 (beta-myocardial myosin) is the main protein component of myocardium in the chamber. (In small body mammals (e.g. rodents), the myocardium alpha myosin is also the main isoform in the ventricular wall.

The only isoform of human smooth muscle myosin 2 (MYH11) or three NM2 (NM2A: MYH9, NM2B: MYH10, NM2C: MYH14) are phylogenetically close to each other; collectively, these are called non-sarcomeric myosin 2 isoforms [Coluccio, L. M. (Ed.). (2007). Myosins: a superfamily of molecular motors (Vol. 7). Springer Science & Business Media]. Each of these myosins is regulated by phosphorylation of RLC or reversible filament polymerization linked thereto. Smooth muscle myosin 2 is the main motor for smooth muscle of hollow organs (except the heart). Several splice forms thereof are known: in the loop-1 region of the ATP binding site of the motordomain a 7 amino acid insert is present in the SMA isoform, whereas SMB does not contain this peptide segment.

TABLE 1

Human myosin 2 heavy chain genes and their encoded myosin heavy chain isoforms

| Myosin heavy chain gene | Isoform |
| --- | --- |
| MYH1 | skeletal muscle 2x/d |
| MYH2 | skeletal muscle 2a |
| MYH3 | embryonic |
| MYH4 | skeletal muscle 2b |
| MYH6 | alpha-cardiac muscle (atrium, atrialis) |
| MYH7 | beta-cardiac muscle (chamber, ventricular) |
| MYH7b | sarcomeric |
| MYH8 | perinatal |
| MYH9 | NM2A |
| MYH10 | NM2B |
| MYH11 | smooth muscle |
| MYH13 | oculomotor muscle (extraocularis) |
| MYH14 | NM2C |
| MYH15 | sarcomeric |
| MYH16 | chewing muscle (pseudo gene inactive in humans) |

NM2 isoforms have a high prevalence in the human body, they are present even in muscle cells. Several types of NM2 isoforms occur in most cell types. The NM2 isoforms of individual organs and tissues also change during the ontogeny. Platelets, a number of blood cell types, lymph nodes, spleen and thymus cells are rich in NM2A. NM2A and NM2C are expressed in the stomach and colon, while 2A isoforms are not present in cardiomyocytes. The brain and testis are also rich in NM2B [Coluccio, L. M. (Ed.). (2007). Myosins: a superfamily of molecular motors (Vol. 7). Springer Science & Business Media].

Various splice forms are expressed by the alternative splicing of the genes of the NM2B and NM2C isoforms: the B1 or C1 forms in the loop-1 region, while the B2 and C2 forms in the loop-2 region of the actin binding site contain insert [Heissler, S. M. and Manstein, D. J. (2013). Non-muscle myosin-2: mix and match. Cellular and molecular life sciences, 70(1), 1-21]. Any combination of the presence of these inserts appears in the body. Forms B1, B2 and C2 are found in the brain and spinal cord, while form C1 is present in all tissues containing NM2C except for adult heart and skeletal muscle.

Each NM2B splice form is expressed in different regions of the brain of adult mice. B2 isoforms are present at low levels in fetal and neonatal mice brains, but are present in higher amounts in the postpartum dendritic and synaptogenesis of the cerebellum Purkinje cells. C0 (no insert) and C1 forms are common, while form C2 is found in nerve tissue or C1C2 form is found in neurites; the latter is the dominant form of NM2C during neuritogenesis.

In most tissues of the adult mouse, NM2C is present in the smallest amount of the three NM2 isoforms. However, immortalized cell lines (e.g., COS-7, HT29) contain significant amounts of NM2C. In tumor cell lines, the C1 form was measured as an increase as compared to non-tumor cell lines from the same tissue.

The Physiological Role of the Individual Isoforms

Sarcomeric myosin 2 isoforms create the driving force of skeletal muscle contraction, which is the basis of voluntary movement activities such as posture changing, walking, chewing, fine movements and speech. The physiological properties of each muscle fiber types (e.g., the speed and energy consumption of muscle contraction) are primarily determined by their myosin 2 heavy chain composition. The different mechanical properties of the heart atria and -ventricles are also determined by the molecular function of the faster mechanochemical cycle atrium (alpha) and slower activity ventricular (beta) myocardial isoforms. Myosin mutations in myocardial myocardium cause a significant proportion of hereditary hypertrophic cardiomyopathies or may also cause dilative cardiomyopathy.

Smooth muscle myosin 2 is responsible for the contraction or toning of the walls of most organs. The faster (having higher ATPase activity and potertial for faster motility) SMB isoform primarily drive the so-called phased, transient contraction (e.g. in the walls of the bladder or portal vein and in the longitudinal smooth muscle layer of the ileum), whereas the slower acting SMA isoform is primarily responsible for slow contraction and long-term strength maintenance (e.g. in the large arteries and trachea wall).

In most cell types, NM2 isoforms have essential or specific functions for cellular movement, cell migration, cell adhesion, cytokinesis, morphogenetic movements (e.g., gastrulation), tissue formation, wound healing, angiogenesis, immune control functions, epithelial-renewal, growth and retraction of cell protrusions (e.g., neurites), membrane transport in cells, clathrin-mediated endocytosis, phagocytosis, exocytosis, plasma membrane fusion of secretory vesicles, and wound induced exocytosis-dependent membrane repair [Newell-Litwa, K A., Horwitz, R. and Lamers, M. L (2015). Non-muscle myosin II in disease: mechanisms and therapeutic opportunities. Disease models & mechanisms, 8(12), 1495-1515]. NM2 isoforms perform these functions in interactions with several cellular actin structures, forming stress strands during cytokinesis in the form of a contractile ring and in the process of cell adhesion forming a peripheral ring.

As with other myosins, the diversity of the molecular activity of isoforms also serves as the basis for the physiological roles of NM2 isoforms. Although all NM2 isoforms have a much slower rate of action compared to muscle myosins, NM2A and NM2C isoforms are relatively faster and have a lower duty ratio (duty ratio, steady-state actin-binding ratio), while NM2B is slower and its function is characterized by significantly higher duty ratio. Of the splice variants, Form B1 exhibits increased ATPase activity and faster motility, while form B2 has no detectable actin-activated ATPase activity and motility. Similarly to form B1, also C1 insert lends an increased ATPase activity and provides potertial for faster motility to myosin, while C1C2 variant has activity independent of RLC phosphorylation.

Of the above-mentioned cell processes, the role of NM2A in clathrin-mediated endocytosis and exocytosis has been demonstrated. Also, the NM2A isoform plays a role in the platelet formation from megakaryocytes.

In the process of cell adhesion, NM2 isoforms play a key role in the dynamic rearrangement of cell-cell contacts and in the formation of apical junction complexes between the apicolateral surfaces of epithelial cells [Vicente-Mananares, M., Ma, X, Adelstein, R. S. and Horwitz, A. R. (2009). Non-muscle myosin II takes centre stage in cell adhesion and migration. Nature reviews Molecular cell biology, 10(11), 778-790].

During cell migration, NM2 isoforms play role in retraction of the rear part of the cell and in the drive of retrograde actin flow in the lamella podium. These myosins exert their power through the stress cables to the generated so-called focal complexes, play a central role in sensing the mechanical stress of the extracellular matrix, coordinate cellular protractions and stabilize the cellular polarity. NM2B is an important component of the power sensing structures found at the back of the cell, while the NM2A isoform is an important factor in the dynamic actin network of the anterior part of the cell. NM2A also plays an important role in the dynamic crosstalk between actin fibers and microtubules.

NM2A and NM2B isoforms co-operate in driving the retrograde actin flow in the axon-end [Kneussel, M. and Wagner, W. (2013). Myosin motors at neuronal synapses: drivers of membrane transport and actin dynamics. Nature Reviews Neuroscience, 14(4), 233-247], and in the growth and retraction of neurites. The reduced expression of the NM2C1C2 isoform leads to the shortening of the neurites.

During cell division, NM2 isoforms generate force in the equatorial region of the dividing cell and play a role in the creation of the mitotic spindle [Wang, A., Ma, X, Conti, M. A. and Adelstein, R. S. (2011). Distinct and redundant roles of the non-muscle myosin II isoforms and functional domains]. The role of the NM2C1 isoform has also been demonstrated in abnormal cell proliferation. Changes in the NM2 function in tumor metastasis can play a role in reducing cell adhesion, promotion of tissue invasion, and promotion of tumor-induced angiogenesis.

Mutations in the NM2A gene cause May-Hegglin anomalies, characterized by a reduced number of platelets, bleeding problems, nephritis, deafness or development of cataracts [Ma, X and Adelstein, R. S. (2014). The role of vertebrate nonmuscle Myosin II in development and human disease. Bioarchitecture, 4(3), 88-102]. The lack of NM2A protein in the mouse causes embryonic lethality through cell adhesion and gastrointestinal defects. Mutations in the NM2B gene in the mouse cause cardiac (cardiomyocyte multinuclease) and brain defects. Ablation of NM2B1 form induces hydrocephalus while the knock out of NM2B2 form causes cerebellar disorders. In humans, the deafness activating point mutation of the NM2C isoform is known.

The role of myosin 2 megakaryocyte (MK) in endomytosis was investigated in WO2012113555A1 international patert publication document, and found that the addition of blebbastatin to MK cell cultures resulted in a significant increase in MK polyploidy.

Inhibitors of Myosin 2

The two most recent reviews on myosin inhibitors and inhibition mechanisms was born in 2013 and 2016. The following table summarizes the structure and effect of myosin 2 inhibitors:

TABLE 2

Structure and effect of myosin 2 inhibitors

| Name | Structure | Binding location | Effect | Binding strength |
|---|---|---|---|---|
| blebbistatin | 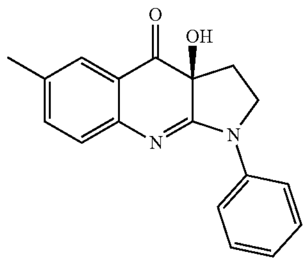 [SMILES: Cc1ccc2c(c1)C(=O)[C@]1(O)CCN(c3ccccc3)C1=N2] | hydrophobic pocket between nucleotide binding pocket and actin binding trench | noncompetitive, inhibits phosphate release | ~0.5-5 μM |
| N-Benzyl-p-toluene-sulfonamide (BTS) | 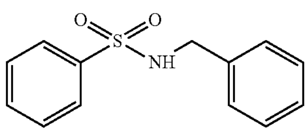 [SMILES: O=S(=O)(NCc1ccccc1)c1ccccc1] | 50 kDa inside the trench | noncompetitive, inhibits phosphate release and ADP release | ~5 μM |
| 2,3-butanedione monoxime (BDM) | 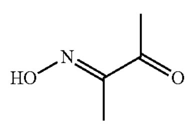 | not characterized | noncompetitive, inhibits phosphate release | ~5 mM |
| vanadate (Vi) | 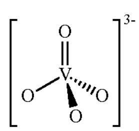 | nucleotide binding pocket | competitive, traps in a kinetically inert state | |

N-Benzyl-p-Toluenesulfonamide (BTS)

Of myosin 2 isoforms, BTS inhibits fast muscle skeletal myosin-2 100 times more stronger, than slow skeletal muscle myosin-2, myocardial myosin-2 or non-muscle myosin 2, and does not inhibit platelet myosin 2-t.

2,3-Butanedione Monoxime (BDM)

BDM inhibits skeletal muscle myosin 2, but binds weakly (IC50~5 mM), data are contradictory on inhibition of other myosin isoforms, and has many other non-myosin targets.

Vanadate (Vi)

Vanadate is a phosphate analogue, in the nucleotide binding pocket in complex with ADP keeps myosin in ATP bound state. It is a general ATP analogue that does not inhibits exclusively the myosin 2 isoform.

Blebbistatin

The best known and most widely used myosin specific inhibitor is blebbistatin. Blebbistatin is an effective inhibitor of non-muscle myosin 2A and B, myocardium, skeletal muscle, and smooth muscle myosin forms, but it does not inhibit myosin 1, myosin 5, and myosin 10.

Blebbistatin rings are hereinafter referred to as A, B, C, and D, respectively.

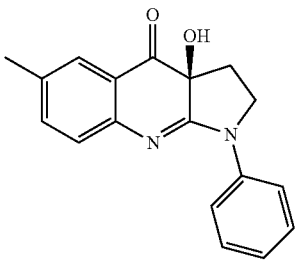 [SMILES: Cc1ccc2c(c1)C(=O)[C@]1(O)CCN(c3ccccc3)C1=N2]

For example, international patent application publication No. WO2009094718A1 discloses the use of certain inhibitors in the treatment of thromboembolic disorders. The document referred to also describes, inter alia, the investigation of the effect of myosin 2A isoform on regulation of blood clot stability in vivo. In this context, blebbastatin is used to inhibit myosin.

Non-muscle myosin 2 ATPase inhibitors are referred to as megakaryocyte modulator compounds in WO2016180918A1 international patent publication document. The document cited relates only to blebbistatin and azidoblebbistatin as examples of said inhibitors.

US2013071927A1 US patert publication document also discloses only two small molecule myosin 2 inhibitors:

N-benzyl-p-toluenesulfonamide and the best described and characterized myosin 2 inhibitor, blebbastatin.

European patent application publication number EP2777703A1 discloses non-muscle myosin 2 antagonists in connection with the treatment of certain diseases by stem cell therapy. As small molecule compounds among said myosin 2 antagonists 2,3-butanedione-2-monoxime, blebbistatin and analogues, derivatives or variants thereof, and pyrrolidone derivatives are mentioned, but the document does not provide information on the structure for analogs, derivatives and variants.

International patent application publication No. WO2016161192A1 discloses blebbistatin and its analogues, such as para-nitro-blebbistatin, (S)-nitro-blebbistatin, and S-(−)7 desmethyl-8-nitro-blebbistatin, as well as N-benzyl-p-toluenesulfonamide and 2,3-butanedione monoxime among small molecule myosin 2 inhibitors. The inhibitors of the cited document differ in structure from the small molecule inhibitors disclosed in the present invention.

International patent application publication No. WO2017129782A1 discloses blebbistatin-skeleton compounds and their preparation which are useful for inhibiting myosin 2 isoforms, in particular for the in vivo inhibiting of the activity of ATPase in neuronal non-muscle myosin 2 isoforms. The referenced document also discloses the use of the disclosed compounds for the treatment or prevention of myosin 2-mediated diseases (e.g., schizophrenia, Alzheimer's disease, Parkinson's disease, cerebral ischemia). The disclosed compounds are characterized by the substitution of ring A and ring D of the blebbistatin backbone with various substituents, i.e., the general formula of the disclosed compounds does not contain a heteroaromatic ring in the position of ring A.

US 2017129886A1 US patent publication document also discloses myosin 2 ATPase inhibitors. The document discloses that the disclosed compounds are suitable for the treatment of overactive bladder. The compounds disclosed there are also blebbistatin-backbone compounds wherein the blebbistatin backbone A, at ring nitrogen and position 2, ring C and/or ring D are substituted with various substituents. The compounds described there do not contain a heteroaromatic ring at the A ring.

International patent application publication No. WO2012158942A2 also relates to myosin 2 ATPase inhibiting compounds, processes for their preparation and their use in the treatment of bladder overactivity. The disclosed compounds are blebbistatin derivatives that are substituted at the 6 and 7 positions of the blebbistatin skeleton, i.e. on ring A, with different substituents. This document does not disclose compounds which contain a heteroaromatic ring at the position of the A ring of the blebbistatin backbone, either.

International patent application publication No. WO2010120785A2 mentions blebbastatin and a number of analogues thereof as a myosin 2 inhibitors. Said analogs are compounds in which the ring A of the blebbastatin backbone is substituted with various substituents, i.e., there is no heteroaromatic ring in place of ring A.

The Problem to be Solved by the Invention

There is a need for novel compounds which, in addition to modular selective/specific inhibition of myosin 2 isoforms, have further advantageous properties such as improved solubility and improved mutagenicity as compared to the state of the art, which properties make these compounds suitable for use in medicine.

The Discovery According to the Present Invention

We have discovered that 1. the structure of the compounds of the present invention has improved solubility and better mutagenicity properties compared to the blebbistatin backbone, and can be used for specific medical indications based on its ability to inhibit myosin 2; and 2. by modifying the D ring, the mutagenicity and specificity of different myosin-2 isoforms (such as skeletal, cardiac, smooth, non-muscle myosin-2/NM2 A, B, C) may be further modulated.

BRIEF DESCRIPTION OF THE FIGURES

FIG. 1: Measurement data for mutagenicity testing for S(−)-blebbistatin (blue) and 188 (green) compounds on TA98 (light circle) and TA100 (dark circle) strains without S9 liver fraction (blank circle) or in the presence of S9 liver fraction (complete disease).

BRIEF DESCRIPTION OF THE INVENTION

1. Compounds of Formula (I) or (II):

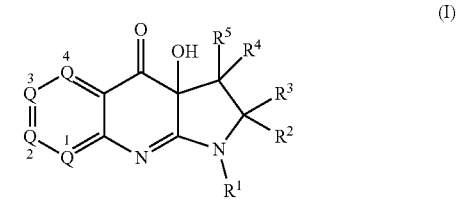

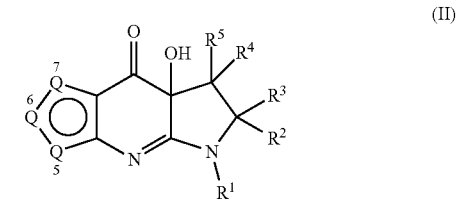

wherein in formula (I)

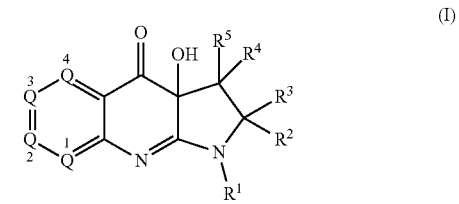

$R^1$ is hydrogen or a group of the following formula,

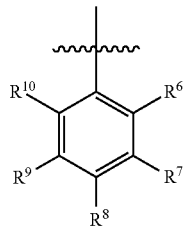

wherein $R^6$ and $R^{10}$ are H-atom;

$R^7$, $R^8$ and $R^9$ are each independently H-atom, halogen, or a saturated, partially saturated, unsaturated, or aromatic 5, 6 or 7 membered heterocyclic group containing, each independently, one or more N, O, S atoms; which may be substituted by one or more groups selected from the group consisting of C1-12 straight or branched alkyl, C3-12 cycloalkyl, C1-12 straight or branched alkenyl, C1-12 straight or branched alkynyl, hydroxyl, C1-12 hydroxyalkyl, C3-12 hydroxycycloalkyl, amino (—NH$_2$), C1-12 alkylamino, C3-12 cycloalkylamino or C1-12 dialkylamino, wherein the amino group may be acylated with a C1-6 straight chain or cyclic or aromatic carboxylic acid, or sulfonylated with C1-6 straight chain or cyclic or aromatic sulfonic acid; nitro (—NO$_2$), cyano (nitrile), C1-12 alkylcyano, C3-12 cycloalkylcyano, C1-12 saturated, unsaturated or aromatic carboxylic acid, C1-12 carboxylic acid amide formed with saturated, unsaturated or aryl-amine, wherein the carboxylic acid amide is a group of formula C(O)NH$_2$—, C(O)NHR$^{11}$— or C(O)NR$^{11}$R$^{12}$—, wherein R$^{11}$ and R$^{12}$ are each independently C1-6 alkyl; C3-12 cycloalkyl, C1-6 alkenyl or C6-12 aryl; C1-12 carboxylic acid ester formed with saturated, unsaturated or aryl alcohol, C1-12 alkoxy, C1-12 alkenyloxy, C1-12 alkynyloxy or C1-12 alkoxyalkyl, wherein the alkyl, cycloalkyl, alkenyl and alkynyl groups may be substituted by one or more halogen atoms; halogen, C1-12 alkylthio, C3-12 cycloalkylthio, C1-12 alkenylthio, C1-12 alkynylthio or alkylthioalkyl, wherein the alkyl, cycloalkyl, alkenyl and alkynyl groups may be substituted with one or more halogen; S(O)OH—, C1-4 alkyl-S(O)$_2$OH— or C3-6 cycloalkyl-S(O)$_2$OH—, S(O)$_2$OR$^{13}$—, C1-4 alkyl-S(O)$_2$OR$^{13}$— or C3-6 cycloalkyl-S(O)$_2$OR$^{13}$—, S(O)R$^{13}$—, C1-4 alkyl-S(O)R$^{13}$— or C3-6 cycloalkyl-S(O)R$^{13}$—, S(O)$_2$R$^{13}$, C1-4 alkyl-S(O)$_2$R$^{13}$— or C3-6 cycloalkyl-S(O)$_2$R$^{13}$—, P(O)$_2$OH—, C1-4 alkyl-P(O)$_2$OH— or C3-6 cycloalkyl-P(O)$_2$OH— P(O)$_2$OR$^{13}$—, C1-4 alkyl-P(O)$_2$OR$^{13}$— or C3-6 cycloalkyl-P(O)$_2$OR$^{13}$—, P(O)$_2$NH$_2$—, C1-4 alkyl-P(O)$_2$NH$_2$— or C3-6 cycloalkyl-P(O)$_2$NH$_2$—, P(O)$_2$NHR$^{13}$—, C1-4 alkyl-P(O)$_2$NHR$^{13}$— or C3-6 cycloalkyl-P(O)$_2$NHR$^{13}$—, P(O)$_2$NR$^{13}$R$^{14}$— or C1-4 alkyl-P(O)$_2$NR$^{13}$R$^{14}$— or C3-6 cycloalkyl-P(O)$_2$NR$^{13}$R$^{14}$-group, wherein R$^{13}$ and R$^{14}$ groups are selected from the group consisting of C1-6 straight chain or branched alkyl, cycloalkyl or C6-12 aryl; or R$^7$, R$^8$ and R$^9$ may be each independently C1-12 straight chain or branched alkyl, C3-12 cycloalkyl, C1-12 straight or branched alkenyl, C1-C12 straight chain or branched alkynyl, hydroxy, C1-12 hydroxy-alkyl, C3-12 hydroxy-cycloalkyl, amino (NH$_2$), C1-12 alkylamino, C3-12 cycloalkylamino or C1-12 dialkylamino, wherein the amino group may be acylated with C1-6 straight chain, or cyclic or aromatic carboxylic acid, or sulfonylated with C1-6 straight chain or cyclic or aromatic sulfonic acid; nitro-(—NO$_2$), cyano (nitrile), C1-12 alkylcyano, C1-12, saturated, unsaturated or aromatic carboxylic acid, C1-12 carboxylic acid amide formed with saturated, unsaturated or aryl-amine, wherein the carboxylic acid amide is a group according to any one of formulae C(O)NH$_2$—, C(O)NHR$^{11}$— or C(O)NR$^{11}$R$^{12}$—, wherein in the formula R$^{11}$ and R$^{12}$ is each independently C1-6 alkyl, C3-12 cycloalkyl, C1-6 alkenyl or C6-12 aryl; C1-12 carboxylic acid ester formed with saturated, unsaturated or aryl alcohol, C1-12 alkoxy, C1-12 alkenyloxy, C1-12 alkynyloxy or alkoxyalkyl, wherein the alkyl, cycloalkyl, alkenyl and alkynyl groups may be substituted with one or more halogen atoms; C1-12 alkylthio, C3-12 cycloalkylthio, C1-12 alkenylthio, C1-12 alkynylthio or alkylthioalkyl, wherein the alkyl, cycloalkyl, alkenyl and alkynyl groups may be substituted with one or more halogen; S(O)$_2$OH—, C1-4 alkyl-S(O)$_2$OH— or C3-6 cycloalkyl-S(O)$_2$OH—, S(O)$_2$OR$^{13}$—, C1-4 alkyl-S(O)$_2$OR$^{13}$— or C3-6 cycloalkyl-S(O)$_2$OR$^{13}$—, S(O)R$^{13}$—, C1-4 alkyl-S(O)R$^{13}$— or C3-6 cycloalkyl-S(O)R$^{13}$—, S(O)$_2$R$^{13}$—, C1-4 alkyl-S(O)$_2$R$^{13}$— or C3-6 cycloalkyl-S(O)$_2$R$^{13}$—, P(O)$_2$OH—, C1-4 alkyl-P(O)$_2$OH— or C3-6 cycloalkyl-P(O)$_2$OH— P(O)$_2$OR$^{13}$—, C1-4 alkyl-P(O)$_2$OR$^{13}$— or C3-6 cycloalkyl-P(O)$_2$OR$^{13}$—, P(O)$_2$NH$_2$—, C1-4 alkyl-P(O)$_2$NH$_2$— or C3-6 cycloalkyl-P(O)$_2$NH$_2$—, P(O)$_2$NHR$^{13}$—, C1-4 alkyl-P(O)$_2$NHR$^{13}$— or C3-6 cycloalkyl-P(O)$_2$NHR$^{13}$—, P(O)$_2$NR$^{13}$R$^{14}$— or C1-4 alkyl-P(O)$_2$NR$^{13}$R$^{14}$— or C3-6 cycloalkyl-P(O)$_2$NR$^{13}$R$^{14}$-group, wherein R$^{13}$ and R$^{14}$ are selected from the group consisting of C1-6 straight chain or branched alkyl, cycloalkyl or C6-12 aryl; methanesulfonylaminomethyl, trifluoromethanesulfonylamino, N,N-dimethylaminocarbonylmethyl [CH$_2$—CO—N(CH$_3$)$_2$], acetyl, methanesulfonylamino, methoxymethyl;

or R$^1$ is a 5, 6 or 7 membered, saturated, partially saturated, unsaturated or aromatic heterocyclic group containing, each independently, one or more N, O, S atoms; which may be substituted by one or more groups selected from the group consisting of C1-12 straight chain or branched alkyl, C3-12 cycloalkyl, C1-12 straight chain or branched alkenyl, C1-12 straight chain or branched alkynyl, hydroxy, C1-12 hydroxyalkyl, C3-12 hydroxycycloalkyl, amino (—NH$_2$), C1-12 alkylamino, C3-12 cycloalkylamino or C1-12 dialkylamino, wherein the amino group may be acylated with C1-6 straight chain or cyclic or aromatic carboxylic acid, or sulfonylated with C1-6 straight chain or cyclic or aromatic sulfonic acid; nitro (—NO$_2$), cyano (nitrile), C1-12 alkylcyano, C3-12 cycloalkylcyano, C1-12 saturated, unsaturated or aromatic carboxylic acid, C1-12 carboxylic acid amide formed with saturated, unsaturated or arylamine, wherein the carboxylic acid amide is a group according to formula C(O)NH$_2$—, C(O)NHR$^{11}$— or C(O)NR$^{11}$R$^{12}$—, wherein R$^{11}$ and R$^{12}$ are each independently C1-6 alkyl-, C3-12 cycloalkyl-, C1-6 alkenyl- or C6-12 aryl; C1-12 carboxylic acid ester formed with saturated, unsaturated or aryl alcohol, C1-12 alkoxy, C1-12 alkenyloxy, C1-12 alkynyloxy- or C1-12 alkoxyalkyl, wherein the alkyl, cycloalkyl, alkenyl and alkynyl groups may be substituted by one or more halogen atoms; halogen; halogen; C1-12 alkylthio, C3-12 cycloalkylthio, C1-12 alkenylthio, C1-12 alkynylthio or alkylthioalkyl, wherein the alkyl, cycloalkyl, alkenyl and alkynyl groups may be substituted with one or more halogen; S(O)$_2$OH—, C1-4 alkyl-S(O)$_2$OH— or C3-6 cycloalkyl-S(O)$_2$OH—, S(O)$_2$OR$^{13}$—, C1-4 alkyl-S(O)$_2$OR$^{13}$— or C3-6 cycloalkyl-S(O)$_2$OR$^{13}$—, S(O)R$^{13}$—, C1-4 alkyl-S(O)R$^{13}$— or C3-6 cycloalkyl-S(O)R$^{13}$—, S(O)$_2$R$^{13}$—, C1-4 alkyl-S(O)$_2$R$^{13}$— or C3-6 cycloalkyl-S(O)$_2$R$^{13}$—, P(O)$_2$OH—, C1-4 alkyl- P(O)₂OH— or C3-6 cycloalkyl-P(O)₂OH— P(O)₂OR¹³—, C1-4 alkyl-P(O)₂OR¹³— or C3-6 cycloalkyl-P(O)₂OR¹³—, P(O)₂NH₂—, C1-4 alkyl-P(O)₂NH₂— or C3-6 cycloalkyl-P(O)₂NH₂—, P(O)₂NHR¹³—, C1-4 alkyl-P(O)₂NHR¹³— or C3-6 cycloalkyl-P(O)₂NHR¹³—, P(O)₂NR¹³R¹⁴— or C1-4 alkyl-P(O)₂NR¹³R¹⁴— or C3-6 cycloalkyl-P(O)₂NR¹³R¹⁴ group. $R^2$, $R^3$, $R^4$ and $R^5$ are selected from the group consisting of H-atom, halogen, preferably F or C1-6 alkyl; and One or more of $Q^1$, $Q^2$, $Q^3$ and $Q^4$ are each independently selected from the group consisting of N-atom and the remaining groups are CH;

(II)

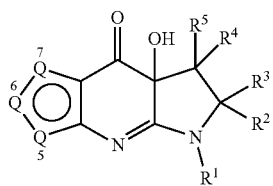

wherein in formula (II)
$R^1$ is H-atom, or a group according to the following formula

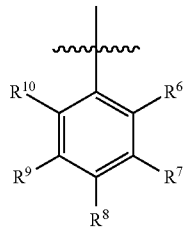

wherein
$R^6$ and $R^{10}$ is H-atom; and
$R^7$, $R^8$ and $R^9$ are each independently H-atom, halogen, a 5, 6 or 7 membered, saturated, partially saturated, unsaturated or aromatic heterocyclic group containing, each independently, one or more N, O, S atoms; which may be substituted by one or more groups selected from the group consisting of C1-12 straight chain or branched alkyl, C3-12 cycloalkyl-, C1-12 straight chain or branched alkenyl-, C1-12 straight chain or branched alkynyl-, hydroxy, C1-12 hydroxyalkyl, C3-12 hydroxycycloalkyl-, amino (—NH₂), C1-12 alkylamino, C3-12 cycloalkylamino or C1-12 dialkylamino, wherein the amino group may be acylated with C1-6 open chain, or cyclic or aromatic carboxylic acid, or sulfonylated with C1-6 open chain, or cyclic or aromatic sulfonic acid; nitro (—NO₂), cyano-(nitrile), C1-12 alkylcyano-, C3-12 cycloalkylcyano, C1-12 saturated, unsaturated or aromatic carboxylic acid, C1-12 carboxylic acid amide formed with saturated, unsaturated or aryl-amine, wherein the carboxylic acid amide is a group according to any one of the following formulae C(O)NH₂—, C(O)NHR¹¹— or C(O)NR¹¹R¹²—, wherein R¹¹ and R¹² is each independently C1-6 alkyl, C3-12 cycloalkyl, C1-6 alkenyl or C6-12 aryl; C1-12 carboxylic acid ester formed with saturated, unsaturated or aryl alcohol, C1-12 alkoxy, C1-12 alkenyloxy, C1-12 alkynyloxy or C1-12 alkoxyalkyl, wherein as alkyl, cycloalkyl, alkenyl and alkynyl groups may be substituted by one or more halogen atoms, halogen, C1-12 alkylthio, C3-12 cycloalkylthio, C1-12 alkenylthio-, C1-12 alkynylthio or alkylthioalkyl, wherein alkyl, cycloalkyl, alkenyl and alkynyl groups may be substituted by one or more halogen atoms; S(O)₂OH—, C1-4 alkyl-S(O)₂OH— or C3-6 cycloalkyl-S(O)₂OH—, S(O)₂OR¹³—, C1-4 alkyl S(O)₂OR¹³— or C3-6 cycloalkyl-S(O)₂OR¹³—, S(O)R¹³—, C1-4 alkyl S(O)R¹³— or C3-6 cycloalkyl-S(O)R¹³—, S(O)₂R¹³—, C1-4 alkyl-S(O)₂R¹³— or C3-6 cycloalkyl-S(O)₂R¹³—, P(O)₂OH—, C1-4 alkyl-P(O)₂OH— or C3-6 cycloalkyl-P(O)₂OH—, P(O)₂OR¹³—, C1-4 alkyl-P(O)₂OR¹³— or C3-6 cycloalkyl-P(O)₂OR¹³—, P(O)₂NH₂—, C1-4 alkyl-P(O)₂NH₂— or C3-6 cycloalkyl-P(O)₂NH₂—, P(O)₂NHR¹³—, C1-4 alkyl-P(O)₂NHR¹³— or C3-6 cycloalkyl-P(O)₂NHR¹³—, P(O)₂NR¹³R¹⁴— or C1-4 alkyl-P(O)₂NR¹³R¹⁴— or C3-6 cycloalkyl-P(O)₂NR¹³R¹⁴, wherein $R^{13}$ and $R^{14}$ groups are selected from the group consisting of C1-6 straight chain or branched alkyl, cycloalkyl or C6-12 aryl; or $R^7$, $R^8$ and $R^9$ may be each independently C1-12 straight chain or branched alkyl, C3-12 cycloalkyl, C1-12 straight chain or branched alkenyl, C1-12 straight chain or branched alkynyl, hydroxy, C1-12 hydroxyalkyl, C3-12 hydroxycycloalkyl, amino (NH₂), C1-12 alkylamino, C3-12 cycloalkylamino or C1-12 dialkylamino, wherein the amino group may be acylated with C1-6 open chain, or cyclic or aromatic carboxylic acid, or sulfonylated with C1-6 open chain, or cyclic or aromatic sulfonic acid; nitro (—NO₂), cyano (nitrile), C1-12 alkylcyano, C1-12, saturated, unsaturated or aromatic carboxylic acid, C1-12 carboxylic acid amide formed with saturated, unsaturated or arylamine, wherein the carboxylic acid amide is a group according to any one of the following formulae: C(O)NH₂—, C(O)NHR¹¹— or C(O)NR¹¹R¹²—, wherein R¹¹ and R¹² are each independently C1-6 alkyl, C3-12 cycloalkyl, C1-6 alkenyl or C6-12 aryl; C1-12 carboxylic acid ester formed with saturated, unsaturated or aryl alcohol, C1-12 alkoxy, C1-12 alkenyloxy, C1-12 alkynyloxy or alkoxyalkyl, wherein the alkyl, cycloalkyl, alkenyl and alkynyl groups may be substituted by one or more halogen atoms, C1-12 alkylthio, C3-12 cycloalkylthio, C1-12 alkenylthio, C1-12 alkynylthio or alkylthioalkyl, wherein the alkyl-, cycloalkyl-, alkenyl and alkynyl groups may be substituted by one or more halogen atoms; S(O)₂OH—, C1-4 alkyl-S(O)₂OH— or C3-6 cycloalkyl-S(O)₂OH—, S(O)₂OR¹³—, C1-4 alkyl-S(O)₂OR¹³— or C3-6 cycloalkyl-S(O)₂OR¹³—, S(O)R¹³—, C1-4 alkyl-S(O)R¹³— or C3-6 cycloalkyl-S(O)R¹³—, S(O)₂R¹³—, C1-4 alkyl-S(O)₂R¹³— or C3-6 cycloalkyl-S(O)₂R¹³—, P(O)₂OH—, C1-4 alkyl-P(O)₂OH— or C3-6 cycloalkyl-P(O)₂OH—, P(O)₂OR¹³—, C1-4 alkyl-P(O)₂OR¹³— or C3-6 cycloalkyl-P(O)₂OR¹³—, P(O)₂NH₂—, C1-4 alkyl-P(O)₂NH₂— or C3-6 cycloalkyl-P(O)₂NH₂—, P(O)₂NHR¹³—, C1-4 alkyl-P(O)₂NHR¹³— or C3-6 cycloalkyl-P(O)₂NHR¹³—, P(O)₂NR¹³R¹⁴— or C1-4 alkyl-P(O)₂NR¹³R¹⁴— or C3-6 cycloalkyl-P(O)₂NR¹³R¹⁴-group, wherein $R^{13}$ and $R^{14}$ is selected from the group consisting of C1-6 straight chain or branched alkyl, cycloalkyl or C6-12 aryl; methanesulfonylaminomethyl, trifluoromethanesulfonylamino, N,N-dimethylaminocarbonylmethyl [CH₂—CO—N(CH₃)₂], acetyl, methanesulfonylamino, methoxymethyl;

or $R^1$ is a 5, 6 or 7 membered, saturated, partially saturated, unsaturated or aromatic heterocyclic group containing, each independently, one or more N, O, S atoms; which may be substituted by one or more groups selected from the group consisting of: C1-12 straight chain or branched alkyl, C3-12 cycloalkyl, C1-12 straight chain or branched alkenyl, C1-straight chain or branched alkynyl, hydroxy, C1-12 hydroxyalkyl, C3-12 hydroxycycloalkyl, amino (—NH₂), C1-12 alkylamino, C3-12 cycloalkylamino or C1-12 dialkylamino, wherein the amino group may be acylated with C1-6 open chain or cyclic or aromatic carboxylic acid, or sulfonylated with C1-6 open chain or cyclic or aromatic sulfonic acid; nitro (—NO$_2$), cyano (nitrile), C1-12 alkyl-cyano, C3-12 cycloalkylcyano, C1-12 saturated, unsaturated or aromatic carboxylic acid, C1-12 carboxylic acid amide formed with saturated, unsaturated or aryl-amine, wherein the carboxylic acid amide is a group according to any one of the following formulae: C(O)NH$_2$—, C(O)NHR$^{11}$— or C(O)NR$^{11}$R$^{12}$, wherein R$^{11}$ and R$^{12}$ are each independently C1-6 alkyl, C3-12 cycloalkyl, C1-6 alkenyl or C6-12 aryl; C1-12 carboxylic acid ester formed with saturated, unsaturated or aryl alcohol, C1-12 alkoxy, C1-12 alkenyloxy-, C1-12 alkynyloxy- or C1-12 alkoxyalkyl, wherein the alkyl, cycloalkyl, alkenyl and alkynyl groups may be substituted by one or more halogen atoms, halogen; C1-12 alkylthio, C3-12 cycloalkylthio, C1-12 alkenylthio, C1-12 alkynylthio or alkylthioalkyl, wherein the alkyl, cycloalkyl, alkenyl and alkynyl groups may be substituted with one or more halogen; S(O)$_2$OH—, C1-4 alkyl-S(O)$_2$OH— or C3-6 cycloalkyl-S(O)$_2$OH—, S(O)$_2$OR$^{13}$—, C1-4 alkyl-S(O)$_2$OR$^{13}$— or C3-6 cycloalkyl-S(O)$_2$OR$^{13}$—, S(O)R$^{13}$—, C1-4 alkyl-S(O) R$^{13}$— or C3-6 cycloalkyl-S(O) R$^{13}$—, S(O)$_2$R$^{13}$—, C1-4 alkyl-S(O)$_2$R$^{13}$— or C3-6 cycloalkyl-S(O)$_2$R$^{13}$—, P(O)$_2$OH—, C1-4 alkyl-P(O)$_2$OH— or C3-6 cycloalkyl-P(O)$_2$OH— P(O)$_2$OR$^{13}$—, C1-4 alkyl-P(O)$_2$OR$^{13}$— or C3-6 cycloalkyl-P(O)$_2$OR$^{13}$—, P(O)$_2$NH$_2$—, C1-4 alkyl-P(O)$_2$NH$_2$— or C3-6 cycloalkyl-P(O)$_2$NH$_2$—, P(O)$_2$NHR$^{13}$—, C1-4 alkyl-P(O)$_2$NHR$^{13}$— or C3-6 cycloalkyl-P(O)$_2$NHR$^{13}$—, P(O)$_2$NR$^{13}$R$^{14}$— or C1-4 alkyl-P(O)$_2$NR$^{13}$R$^{14}$— or C3-6 cycloalkyl-P(O)$_2$NR$^{13}$R$^{14}$-group.

R$^2$, R$^3$, R$^4$ and R$^5$ are selected from H-atom, halogen, preferably F or C1-6 alkyl; and Q$^5$, Q$^6$ and Q$^7$ are each independently selected from the group consisting of S, O, N, NH or CH, provided that the aromatic nature of the ring is retained; wherein CH or NH may be substituted with C1-6 alkyl or haloalkyl;

and pharmaceutically acceptable salts, solvates, tautomers, stereoisomers thereof including enantiomers, diastereomers, racemic mixtures, mixtures of enantiomers, or combinations thereof.

2. Compounds of Formula (I) or (II) According to Item 1; wherein in formula (I)

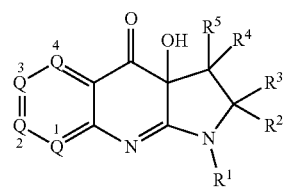

(I)

R$^1$ is hydrogen, or a group according to the following formula

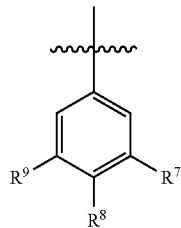

wherein in the above formula

R$^7$, R$^8$ and R$^9$ are independently selected from the group consisting of H-atom, morpholinyl, amino (—NH$_2$), nitro (—NO$_2$), cyano (nitrile), carboxylic acid amide (—CONH$_2$), methoxy (—OCH$_3$), trifluoromethyl, fluoro, trifluoromethoxy, dimethylamino, hydroxymethyl, cyanomethyl, aminomethyl, methanesulfonylaminomethyl, trifluoromethanesulfonylamino, N,N-dimethylamino carbonylmethyl [CH$_2$—CO—N(CH$_3$)$_2$—], acetyl, methanesulfonylamino, methoxymethyl, 1,4-oxazepan-4-yl, oxan-4-yl, tetrahydro-thiopyran-4-yl, 1,1-dioxo-tetrahydropyran-4-yl, thiomorpholin-4-yl, 1,1-dioxothiomorpholin-4-yl, tetrahydropyran-4-yl, 1-methyl piperidin-4-yl; or R$^4$ is selected from the group consisting of 3-pyridyl or 4-pyridyl, 2-thienyl, 3-thienyl, 2-methoxy-4-pyridyl, 6-methoxy-3-pyridyl;

R$^2$, R$^3$, R$^4$ and R$^5$ are H-atom; and one of Q$^1$, Q$^2$, Q$_3$ and Q$^4$ groups is N-atom and the others are CH; and wherein in formula (II)

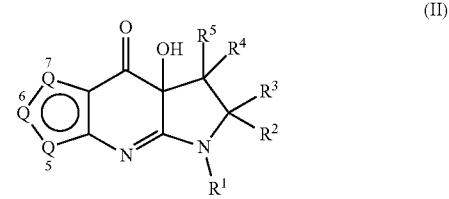

(II)

R$^1$ is hydrogen, or a group according to the following formula

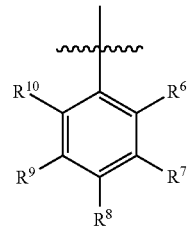

wherein in the above formula

R$^6$ and R$^{40}$ are H-atom, and

R$^7$, R$^8$ and R$^9$ are independently selected from the group consisting of H-atom, morpholinyl, amino (—NH$_2$), nitro (—NO$_2$), cyano (nitrile), carboxylic acid amide (—CONH$_2$), methoxy (—OCH$_3$), trifluoromethyl, fluoro, trifluoromethoxy, dimethylamino, hydroxymethyl, cyanomethyl, aminomethyl, methanesulfonylaminomethyl, trifluoromethanesulfonylamino, N,N-dimethylamino carbonylmethyl [CH$_2$—CO—N(CH$_3$)$_2$—], acetyl, methanesulfonylamino, methoxymethyl, 1,4-oxazepan-4-yl, oxan-4-yl, tetrahydro thiopyran-4-yl, 1,1-dioxo-tetrahydropyran-4-yl, thiomorpholin-4-yl, 1,1-dioxothiomorpholin-4-yl, tetrahydropyran-4-yl, 1-methyl piperidin-4-yl; or $R^1$ is selected from the group consisting of 3-pyridyl or 4-pyridyl, 2-thienyl, 3-thienyl, 2-methoxy-4-pyridyl, 6-methoxy-3-pyridyl;

$R^2$, $R^3$, $R^4$ and $R^5$ are H-atom; and $Q^5$, $Q^6$ and $Q^7$ are as follows: $Q^5$ is S-atom and $Q^6$ and $Q^7$ are CH, or $Q^7$ is S-atom and $Q^5$ and $Q^6$ is CH, or $Q^5$ is N—CH$_3$ and $Q^6$ is N-atom and $Q^7$ is CH, or $Q^5$ is S-atom and $Q^6$ is C—CH$_3$ and $Q^7$ is CH, and pharmaceutically acceptable salts, solvates, tautomers, stereoisomers thereof including enantiomers, diastereomers, racemic mixtures, mixtures of enantiomers, or combinations thereof.

3. The Compounds of Formulae (I) or (II) According to Item 1 or 2, wherein in formula (I)

(I)

$R^1$ is hydrogen, or a group according to the following formula wherein in the above formula $R^6$ and $R^{10}$ are H-atom, and $R^7$ and $R^9$ are selected from the group consisting of H-atom, amino (—NH$_2$), cyano or methoxy (—OCH$_3$), and $R^8$ is selected from the group consisting of H-atom, morpholinyl, amino (—NH$_2$), nitro (—NO$_2$), cyano (nitrile), carboxylic acid amide (—CONH$_2$), methoxy (—OCH$_3$), trifluoromethyl, fluoro, trifluoromethoxy, dimethylamino, hydroxymethyl, cyanomethyl, aminomethyl, methanesulfonylaminomethyl, trifluoromethanesulfonylamino, N,N-dimethylaminocarbonylmethyl [CH$_2$—CO—N(CH$_3$)$_2$—], acetyl, methanesulfonylamino, methoxymethyl, 1,4-oxazepan-4-yl, oxan-4-yl, tetrahydro-thiopyran-4-yl, 1,1-dioxotetrahydropyran-4-yl, thiomorpholin-4-yl, 1,1-dioxothiomorpholin-4-yl, tetrahydropyran-4-yl, 1-methylpiperidin-4-yl]; or $R^1$ is selected from the group consisting of 3-pyridyl or 4-pyridyl, 2-thienyl, 3-thienyl, 2-methoxy-4-pyridyl, 6-methoxy-3-pyridyl;

$R^2$, $R^3$, $R^4$ and $R^5$ are H-atom; and

One of $Q^1$, $Q^2$, $Q^3$ and $Q^4$ is N-atom and the others are CH; and wherein in formula (II)

(II)

$R^1$ is hydrogen, or a group according to the following formula wherein in the above formula $R^6$ and $R^{10}$ are H-atom, and $R^7$ and $R^9$ are H-atom, amino (—NH$_2$), cyano or methoxy (—OCH$_3$), and $R^8$ is selected from the group consisting of H-atom, morpholinyl, amino (—NH$_2$), nitro (—NO$_2$), cyano (nitrile), carboxylic acid amide (—CONH$_2$), methoxy (—OCH$_3$), trifluoromethyl, fluoro, trifluoromethoxy, dimethylamino, hydroxymethyl, cyanomethyl, aminomethyl, methanesulfonylaminomethyl, trifluoromethanesulfonylamino, N,N-dimethylaminocarbonylmethyl [CH$_2$—CO—N(CH$_3$)$_2$H, acetyl, methanesulfonylamino, methoxymethyl, 1,4-oxazepan-4-yl, oxan-4-yl, tetrahydro-thiopyran-4-yl, 1,1-dioxo-tetrahydropyran-4-yl, thiomorpholin-4-yl, 1,1-dioxothiomorpholin-4-yl, tetrahydropyran-4-yl, 1-methylpiperidin-4-yl] group; or $R^1$ is selected from the group consisting of 3-pyridyl or 4-pyridyl, 2-thienyl, 3-thienyl, 2-methoxy-4-pyridyl, 6-methoxy-3-pyridyl;

$R^2$, $R^3$, $R^4$ and $R^5$ are H-atom; and $Q^5$, $Q^6$ and $Q^7$ are as follows: $Q^5$ is S-atom and $Q^6$ and $Q^7$ are CH, or $Q^7$ is S-atom and $Q^5$ and $Q^6$ are CH, or $Q^5$ are N—CH$_3$ and $Q^6$ is N-atom and $Q^7$ is CH, or $Q^5$ is S-atom and $Q^6$ is C—CH$_3$ and $Q^7$, and pharmaceutically acceptable salts, solvates, tautomers, stereoisomers thereof including enantiomers, diastereomers, racemic mixtures, mixtures of enantiomers, or combinations thereof.

4. The Compounds of Formula (I) or (II) According to Items 1 to 3, wherein in formula (I)

(I)

R¹ is hydrogen, or a group according to the following formula

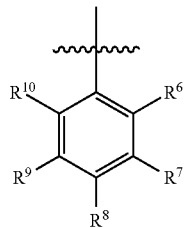

wherein in the above formula
$R^6$, $R^7$, $R^9$ and $R^{10}$ are H-atom, and
$R^8$ is H-atom or morpholinyl;
$R^2$, $R^3$, $R^4$ and $R^5$ are H-atom; and
One of $Q^1$, $Q^2$, $Q^3$ and $Q^4$ is N-atom and the others are CH; and wherein in formula (II)

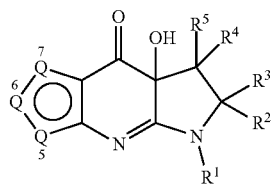
(II)

R¹ is hydrogen, or a group according to the following formula

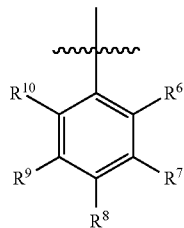

wherein in the above formula
$R^6$, $R^7$, $R^9$ and $R^{10}$ are H-atom, and
$R^8$ is H-atom or morpholinyl;
$R^2$, $R^3$, $R^4$ and $R^5$ are H-atom; and
$Q^5$, $Q^6$ and $Q^7$ are as follows: $Q^5$ is S-atom and $Q^6$ and $Q^7$ are CH, or $Q^7$ is S-atom and $Q^5$ and $Q^6$ are CH, or $Q^5$ is N—CH$_3$ and $Q^6$ is N-atom and $Q^7$ is CH,
and pharmaceutically acceptable salts, solvates, tautomers, stereoisomers thereof including enantiomers, diastereomers, racemic mixtures, mixtures of enantiomers, or combinations thereof.

5. The Following Compounds of Formula (I) or (II) According to Items 1 to 4:
3a-hydroxy-1-phenyl-1H,2H,3H,3aH,4H-pyrrolo[2,3-b]1,7-naphthyridin-4-one,
9-hydroxy-12-phenyl-4-thia-2,12-diazatricyclo[7.3.0.0³,⁷]dodeca-1,3(7),5-trien-8-one,
7-hydroxy-4-phenyl-10-thia-2,4-diazatricyclo[7.3.0.0³,⁷]dodeca-1(9),2,11-trien-8-one,
9-hydroxy-12-[4-(morpholin-4-yl)phenyl]-4-thia-2,12-diazatricyclo[7.3.0.0³,⁷]dodeca-1,3 (7),5-trien-8-one,
3a-hydroxy-1-phenyl-1H,2H,3H,3aH,4H-pyrrolo[2,3-b]1,8-naphthyridin-4-one,
8a-hydroxy-6-phenyl-6H,7H,8H,8aH,9H-pyrrolo[2,3-b]1,5-naphthyridin-9-one,
9-hydroxy-5-methyl-12-phenyl-4-thia-2,12-diazatricyclo [7.3.0.0³,⁷]dodeca-1,3 (7),5-trien-8-one,
12-phenyl-9-hydroxy-6-methyl-4-thia-2,5,12-triazatricyclo [7.3.0.0³,⁷]dodeca-1,3 (7),5-trien-8-one,
(9S)-9-hydroxy-4-thia-2,12-diazatricyclo[7.3.0.0³,⁷]dodeca-1,3(7),5-trien-8-one,
(9S)-9-hydroxy-5-methyl-12-(thiophen-2-yl)-4-thia-2,12-diazatricyclo[7.3.0.0³,⁷]dodeca-1,3(7),5-trien-8-one,
(9S)-12-(4-aminophenyl)-9-hydroxy-4-thia-2,12-diazatricyclo[7.3.0.0³,⁷]dodeca-1,3 (7),5-trien-8-one,
(9S)-9-hydroxy-12-(4-methoxyphenyl)-4-thia-2,12-diazatricyclo[7.3.0.0³,⁷]dodeca-1,3 (7),5-trien-8-one,
(9S)-9-hydroxy-12-[4-(trifluoromethoxy)phenyl]-4-thia-2,12-diazatricyclo[7.3.0.0³,⁷]dodeca-1,3(7),5-trien-8-one,
(9S)-4-{9-hydroxy-8-oxo-4-thia-2,12-diazatricyclo[7.3.0.0³,⁷]dodeca-1,3(7),5-trien-12-yl}benzonitrile,
(9S)-12-(4-acetylphenyl)-9-hydroxy-4-thia-2,12-diazatricyclo[7.3.0.0³,⁷]dodeca-1,3(7),5-trien-8-on,
(9S)-2-(4-{9-hydroxy-8-oxo-4-thia-2,12-diazatricyclo [7.3.0.0³,⁷]dodeca-1,3(7),5-trien yl}phenyl)acetonitrile,
(9S)-9-hydroxy-12-[4-(hydroxymethyl)phenyl]-4-thia-2,12-diazatricyclo[7.3.0.0³,⁷]dodeca-1,3 (7),5-trien-8-one,
(9S)-9-hydroxy-12-(thiophen-2-yl)-4-thia-2,12-diazatricyclo[7.3.0.0³,⁷]dodeca-1,3 (7),5-trien-8-one,
(9S)-9-hydroxy-12-(6-methoxypyridin-3-yl)-4-thia-2,12-diazatricyclo[7.3.0.0⁷]dodeca-1,3 (7),5-trien-8-one,
9-hydroxy-5-methyl-12-[4-(morpholin-4-yl)phenyl]-4-thia-2,12-diazatricyclo[7.3.0.0³'''']dodeca-1,3 (7),5-trien-8-one,
12-(4-aminophenyl)-9-hydroxy-5-methyl-4-thia-2,12-diazatricyclo[7.3.0.0³,⁷]dodeca-1,3 (7),5-trien-8-on,
9-hydroxy-12-(4-methoxyphenyl)-5-methyl-4-thia-2,12-diazatricyclo[7.3.0.0³,⁷]dodeca-1,3 (7),5-trien-8-one,
9-hydroxy-5-methyl-12-[4-(trifluoromethoxy)phenyl]-4-thia-2,12-diazatricyclo[7.3.0.0³,⁷]dodeca-1,3 (7),5-trien-8-one,
4-{9-hydroxy-5-methyl-8-oxo-4-thia-2,12-diazatricyclo [7.3.0.0³,⁷]dodeca-1,3 (7),5-trien-12-yl}benzonitrile,
12-(4-acetylphenyl)-9-hydroxy-5-methyl-4-thia-2,12-diazatricyclo[7.3.0.0³,⁷]dodeca-1,3 (7),5-trien-8-one,
2-(4-{9-hydroxy-5-methyl-8-oxo-4-thia-2,12-diazatricyclo [7.3.0.0³,⁷]dodeca-1,3 (7),5-trien-12-yl}phenyl) acetonitrile,
9-hydroxy-12-[4-(hydroxymethyl)phenyl]-5-methyl-4-thia-2,12-diazatricyclo[7.3.0.0³,⁷]dodeca-1,3 (7),5-trien-8-one,
9-hydroxy-5-methyl-12-(thiophen-2-yl)-4-thia-2,12-diazatricyclo[7.3.0.0³,⁷]dodeca-1,3 (7),5-trien-8-one,
9-hydroxy-12-(6-methoxypyridin-3-yl)-5-methyl-4-thia-2,12-diazatricyclo[7.3.0.0³,⁷]dodeca-1,3 (7),5-trien-8-one,
9-hydroxy-5-methyl-4-thia-2,12-diazatricyclo[7.3.0.0³,⁷] dodeca-1,3 (7),5-trien-8-one,
(9S)-9-hydroxy-12-(4-methylphenyl)-4-thia-2,12-diazatricyclo[7.3.0.0³,⁷]dodeca-1,3 (7),5-trien-8-one,
12-[4-(methyl)phenyl]-9-hydroxy-5-methyl-4-thia-2,12-diazatricyclo[7.3.0.0³,⁷]dodeca-1,3 (7),5-trien-8-one,
3a-hydroxy-1-[4-(trifluoromethoxy)phenyl]-1H,2H,3H, 3aH,4H-pyrrolo[2,3-b]1,7-naphthyridin one,
1-(4-acetylphenyl)-3α-hydroxy-1H,2H,3H,3aH,4H-pyrrolo [2,3-b]1,7-naphthyridin-4-one,
1-[4-(methyl)phenyl]-3α-hydroxy-1H,2H,3H,3aH,4H-pyrrolo[2,3-b]1,7-naphthyridin-4-one, 3α-hydroxy-1-[4-(morpholin-4-yl)phenyl]-1H,2H,3H,3aH, 4H-pyrrolo[2,3-b]1,7-naphthyridin-4-one,
(9S)-12-[4-(dimethylamino)phenyl]-9-hydroxy-4-thia-2,12-diazatricyclo[7.3.0.0$^{3,7}$]dodeca-1,3(7),5-trien-8-one,
12-[4-(dimethylamino)phenyl]-9-hydroxy-5-methyl-4-thia-2,12-diazatricyclo[7.3.0.0$^{3,7}$]dodeca-1,3(7),5-trien-8-one,
1-[4-(dimethylamino)phenyl]-3α-hydroxy-1H,2H,3H,3aH, 4H-pyrrolo[2,3-b]1,7-naphthyridin-4-one,
3α-hydroxy-1H,2H,3H,3aH,4H-pyrrolo[2,3-b]1,7-naphthyridin-4-one.

6. The compounds according to any one of Items 1 to 5 for use in the treatment of conditions and diseases selected from the group consisting of pro-platelet formation, chemotherapy, cancer metastasis, leukemic cell migration, thrombosis, including arterial thrombosis, including ischemic stroke, nerve and muscle injuries, including neuronal apoptosis and spinal cord injuries, drug prevention including prevention of relapse associated with methamphetamine use, and drug-related disorders, peripheral neuropathy, hepatocarcinoma, lung carcinoma, benign prostate enlargement, length dependent neuropathy, fibrosis, including lung, liver and joint fibrosis, wound healing, haemostasis and thrombosis, including clot retertion, periodontitis, pathological apoptosis, immune diseases, including multiple sclerosis, viral diseases including herpes caused diseases, hypertension, pulmonary (arterial) hypertension, erectile dysfunction, thrombotic disorders, urinary problems including excessive bladder activity, bladder blockage, cardiomyopathies including hypertrophic cardiomyopathy and dilated cardiomyopathy, muscle spasms including non-specific lower lower-back pains, lumbar spasm or spasmodic spasm, stress-induced occiput spasms, prolonged muscle spasms in limbs in epilepsia partialis continua, post-stroke spasticity, muscle spasms in cerebral palsy and multiple sclerosis, vaginismus, musculoskeletal muscle and smooth muscle spasm during labor, drug-induced convulsions, myopathies in myocardial and skeletal muscle, including altered ability of myofilaments to exert effort.

DETAILED DESCRIPTION OF THE INVENTION

The present invention relates to compounds of formula (I) or (II) as described above in Item 1, wherein the identifiers in the formulae are as defined in Item 1, and pharmaceutically acceptable salts, solvates, tautomers, stereoisomers thereof, including enantiomers, diastereomers, racemic mixtures, mixtures of enantiomers, or combinations thereof.

A group of compounds of the present invention is a compound of formula (I) or (II) as described above, wherein the identifiers in the formulae are as defined in Item 2, and pharmaceutically acceptable salts, solvates, tautomers thereof; stereoisomers, including enantiomers, diastereomers, racemic mixtures, mixtures of enantiomers, or combinations thereof.

Another group of compounds of the present invention are compounds of formula (I) or (II) as described above in Item 3, wherein the identifiers in the formulae are as defined in Item 3, and the pharmaceutically acceptable salts, solvates, tautomers, stereoisomers thereof, including enantiomers, diastereomers, racemic mixtures, mixtures of enantiomers, or combinations thereof.

A further group of compounds of the present invention is a compound of formula (I) or (II) as described above in Item 4, wherein the identifiers in the formulae are as defined in Item 4, and the pharmaceutically acceptable salts, solvates, tautomers, stereoisomers thereof, including enantiomers, diastereomers, racemic mixtures, mixtures of enantiomers, or combinations thereof.

A further group of compounds of the present invention is a compound of formula (I) or (II), as described above in Item 5, further identified by its chemical name, and the pharmaceutically acceptable salts, solvates, tautomers, stereoisomers thereof, including enantiomers, diastereomers, racemic mixtures, mixtures of enantiomers, or combinations thereof.

As noted above, the compounds of the present invention may exist as racemic mixtures and as optical isomers, in the form of one enantiomer which is pure or predominantly present. It will be appreciated that both racemic mixtures and enantiomers in pure form or in the mixture predominantly as compared to the other enantiomer belong to the subject matter of the invention.

According to the imine-amine tautomerism, 1,6-dihydro-7H-imidazo[4,5-b]pyridin-7-one is also known as 1,6-dihydro-7H-imidazo[4,5-b]pyridin-7-on, which equilibrium forms are different from each other in the position of a proton and a double bond. The same applies to certain compounds of the invention.

Some compounds of the present invention may contain one or more chiral centers and may therefore exist in enantiomeric or diastereoisomeric forms. The subject matter of the present invention is intended to include all isomers per se, as well as a mixture of cis and trans isomers, a mixture of diastereomers, and a mixture of enantiomers (optical isomers). Furthermore, it is possible to use well-known techniques for separating different forms, and the invention may include a purified or enriched form of a particular enantiomer or diastereomer species.

The invention further relates to pharmaceutically acceptable salts and solvates of the compounds of the invention.

Human myosin 2 isoforms play a significant role in the development of medical indications related to neurological, skeletal, cardiac and smooth muscle and cell division and cell migration.

In neurological terms, their role in apoptotic and neuroregenerative processes in nerve injuries is significant, as is the development of specific memory related to drug use. Based on these effects, the claimed myosin 2 inhibitors may be useful for improving the symptoms of neurodegenerative, neuropathic, psychiatric and neurological disorders, and neuronal injuries, such as, but not limited to, schizophrenia, cerebral ischemia, stroke, neuropathic pain, spinal cord injury, Alzheimer's disease, Parkinson's Disease, amyotropic lateral sclerosis, Huntington's Disease, addiction, cerebral tumors, brain asphyxia, post-traumatic stress syndrome, and multiple sclerosis. Additionally, depression, obsessive-compulsive disease, visual hallucination, hearing hallucination, eating disorders, bipolar disorder, cerebellar ataxia, cerebrovascular injury, corticobazal ganglion degeneration, Creutzfeldt-Jakob Syndrome, Dandy-Walker Syndrome, dementia, encephalitis, encephalomyelitis, epilepsy, Hallervorden-Spatz Syndrome, hydrocephalus, lacunar infarction, Landau-Kleffner Syndrome, Lewy-Body Disease, Machado-Joseph Disease, Meige Syndrome, Shy-Drager Syndrome, neuroaxoneal dystrophies, spinocerebellar ataxia, spinocerebellar degeneration, Tourette Syndrome.

The active compounds as subject-matter of the present invention are suitable for the alleviation of symptoms of disorders associated with muscle spasms, through relaxation of skeletal muscle, said symptoms being such as, but not limited to, non-specific lower abdominal pains, muscle spasms associated with lumbago or cartilage hernia, or in epilepsia partialis continua, prolonged muscle spasms in the limbs, and as additional symptoms, muscle spasms in multiple sclerosis, the gynecological indications include vaginismus, skeletal muscle and smooth muscle spasms during labor, myopathies in the heart and skeletal muscles in case of constipation (obstipatio).

Non-limiting further indications of the claimed active ingredients are thrombotic diseases, hypertension, pulmonary (arterial) hypertension, hypertrophic and dilated myocardial distress, urinary problems such as excessive bladder activity, bladder blockage, or erectile dysfunction.

Due to their role in cell migration, the non-limiting indications of the claimed active ingredients are cancer metastases, pulmonary, hepatic and articular fibrosis. Furthermore, non-limiting indications related to wound healing processes are idiopathic keloid and Dupuytren contractures, desmoplastic (cancerous), autoimmune (sclerodermal), inflammatory (Crohn's disease) and infectious (cirrhosis) or traumatic (cicatricial ectropia) lesions.

The invention also relates to the compounds of the invention for use in the treatment of conditions and diseases selected from the group consisting of pro-platelet formation, chemotherapy, cancer metastasis, leukemic cell migration, thrombosis including arterial thrombosis, nerve damage including neuronal apoptosis and spinal cord injuries, drug prevention, including prevention of methamphetamine-related relapse and drug-abuse related disorders, peripheral neuropathy, hepatocarcinoma, lung carcinoma, benign prostate enlargement, length dependent neuropathy, fibrosis including lung, liver and joint fibrosis, wound healing, hemostasis and thrombosis including blood clot retertion, periodontitis, pathological apoptosis, immune diseases including multiple sclerosis, virus-induced diseases including diseases caused by herpes virus, hypertension, pulmonary (arterial) hypertension, erectile dysfunction, thrombotic disorders, urinary problems including excessive bladder activity, bladder blockage, cardiomyopathies including hypertrophic cardiomyopathy and dilated cardiomyopathy, muscle spasms including non-specific lower-back pains, lumbago, or spasms associated with disc herniation, stress-induced occiput spasms, prolonged muscle spasms in limbs in epilepsia partialis continua, and as additional symptoms, muscle spasms in multiple sclerosis, vaginismus, skeletal muscle and smooth muscle spasms during labor, and drug-induced spasms, myopathies in cardiac and skeletal muscle, including altered ability of myofilaments to exert effort.

Preparation of Compounds of the Invention

The synthesis of compounds of the present invention having an aromatic heterocycle in ring A can be accomplished by the following reaction scheme:

Scheme 1

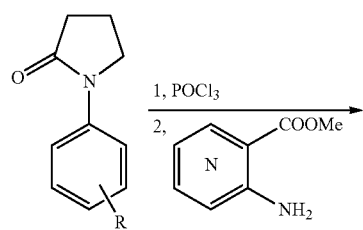

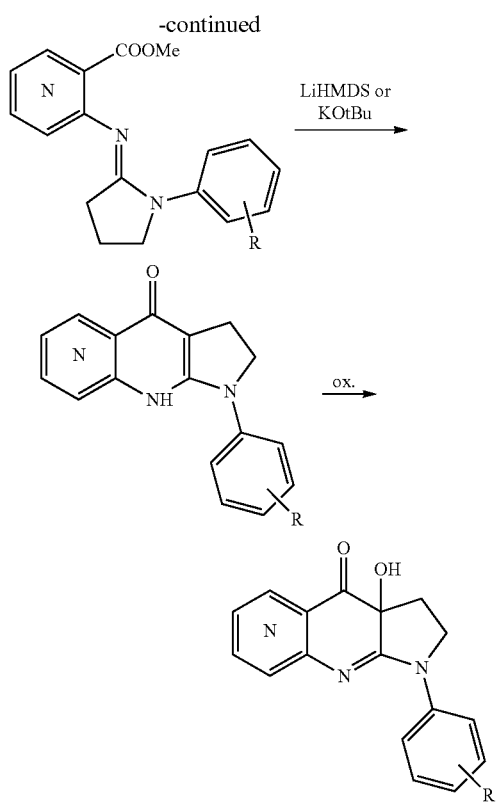

In Scheme 1, instead of the aromatic ring designated as N, the 5-membered ring of formula (II) may also be used, wherein the 5-membered ring variables are as defined in Item 1 above. Furthermore, the group R in Scheme 1 has the same meaning as $R^6$, $R^7$, $R^8$, $R^9$ and $R^{10}$ as defined in Item 1.

Examples of the compounds of the invention that can be prepared by the above-mentioned Scheme 1 include, but are not limited to, the following compounds:

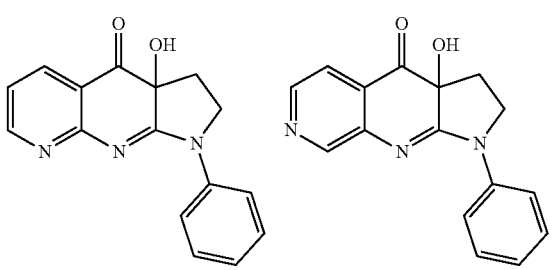

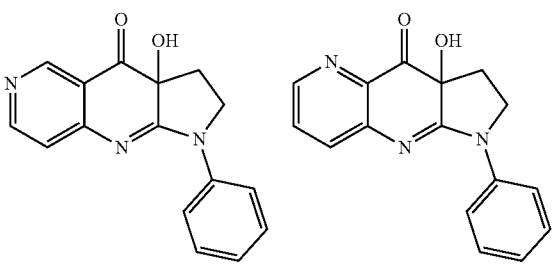

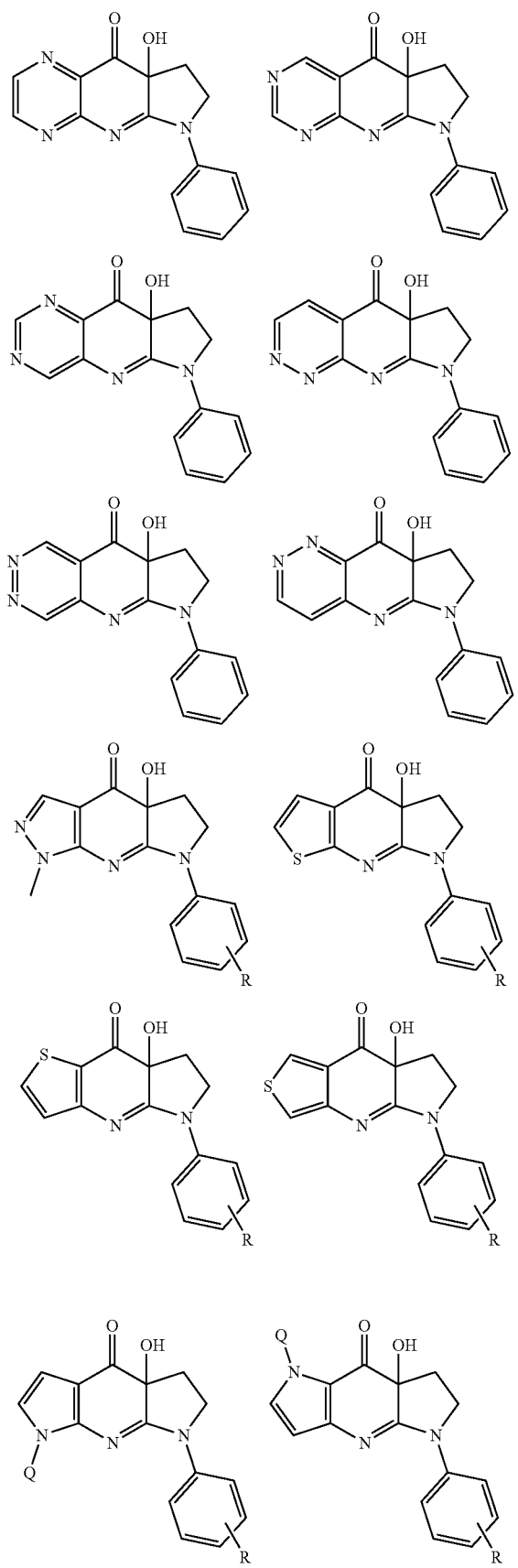

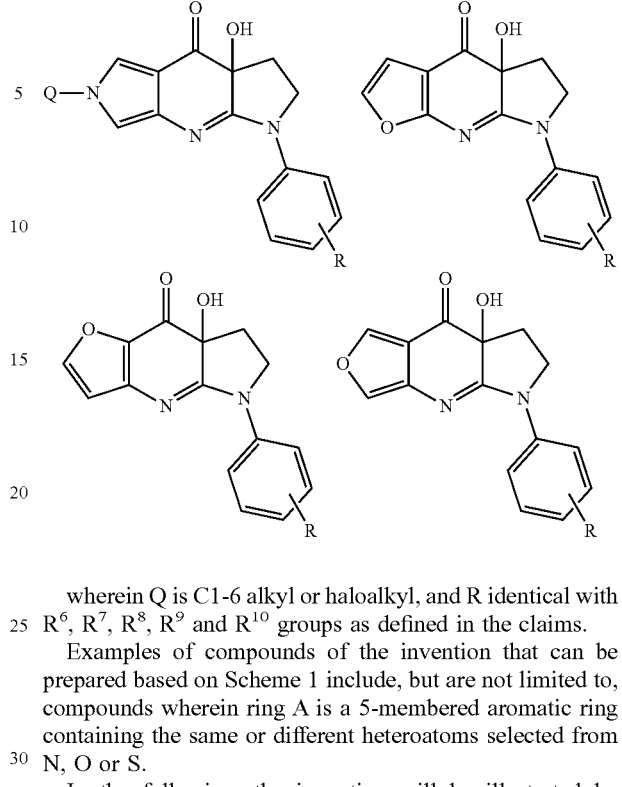

wherein Q is C1-6 alkyl or haloalkyl, and R identical with $R^6$, $R^7$, $R^8$, $R^9$ and $R^{10}$ groups as defined in the claims.

Examples of compounds of the invention that can be prepared based on Scheme 1 include, but are not limited to, compounds wherein ring A is a 5-membered aromatic ring containing the same or different heteroatoms selected from N, O or S.

In the following, the invention will be illustrated by means of exemplary embodiments which, however, are not to be construed as limiting the invention.

EXAMPLES

Example 1: Preparation of 3a-Hydroxy-1-phenyl-1H,2H,3H,3aH,4H-pyrrolo[2,3-b)]1,7-naphthyridin-4-one (Compound 1)

Step a) Preparation of Ethyl-3-{[(2E)-1-phenylpyrrolidin-2-ylidene]amino}pyridine-4-carboxylate (Compound 1a)

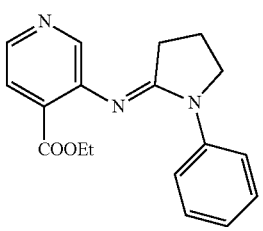

(Compound 1a)

4.36 g (27.08 mmol, 1 eq.) of 1-phenylpyrrolidin-2-one were dissolved in dichloromethane (35 mL) under argon and 4.15 g (2.5 mL, 27.08 mmol, 1 eq.) $POCl_3$ is added. After stirring for 3 hours at room temperature, a solution of 5.00 g (30.09 mmol, 1.1 eq.) of ethyl 3-aminopyridine-4-carboxylate in dichloromethane (35 mL) was added over 5 minutes through a dripping top. The reaction mixture was refluxed for 16 hours. At the end of the reflux, the reaction mixture was cooled to room temperature and stirred with saturated $NaHCO_3$ solution to keep the aqueous phase alkaline (pH=8). The solution is added gently due to foaming. The organic phase is then dried over $Na_2SO_4$, filtered and concentrated. 5.80 g of crude ethyl-3-{[(2E)-1-phenylpyrrolidin-2-ylidene]amino}pyridine-4-carboxylate (Compound 1a) is retained which is used without further purification. $M+H^+=310.35$ Step b) Preparation of 1-Phenyl-1H,2H,3H, 4H,9H-pyrrolo[2,3-b]1,7-naphthyridin-4-one (Compound 1b)

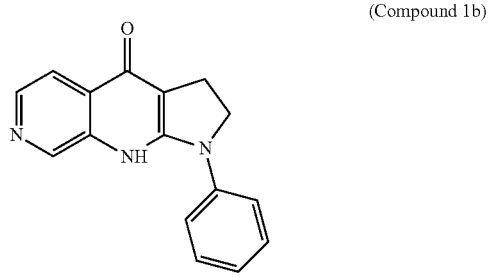 [SMILES: O=c1c2c([nH]c3cnccc13)N(c1ccccc1)CC2]

(Compound 1b)

The 5.80 g crude product (Compound 1a, 18.76 mmol) obtained in step a) was dissolved in dry tetrahydrofuran (140 ml). It was cooled with argon under dry ice-acetone cooling mixture, and a solution of 9.42 g of lithium hexamethyldisilazane (39.2 mL, 56.27 mmol, 3 eq.) in 20% tetrahydrofuran was added below −60° C. After one hour the reaction mixture was then allowed to warm to room temperature. After 3 hours, the reaction mixture was treated with 2 M hydrochloric acid to dissolve all precipitate (about 100 mL). The organic layer was then separated and the aqueous layer extracted with ethyl acetate (3×50 mL). The aqueous phase is concentrated on a vacuum evaporator until the organic solvent residues are removed. The solution is then neutralized by adding $NaHCO_3$ solution. The precipitate formed is filtered off and dried under vacuum. 3.61 g of crude product is obtained, which is recrystallized from 30 g of dimethylformamide. Yield: 1.74 g of pale yellow crystals (6.61 mmol, 24% based on 1-phenylpyrrolidin-2-one) 1-phenyl-1H,2H,3H,4H,9H-pyrrolo[2,3-b] 1 7-naphthyridin-4-one (Compound 1b). $M+H^+=264.30$ $^1H$ NMR (500 MHz, DMSO-$d_6$): δ=3.22 (t, J=8.8 Hz, 2H), 4.13 (t, J=8.0 Hz, 2H), 7.05 (t, J=7.3 Hz, 1H), 7.41 (dd, J=7.6, 8.1 Hz, 2H), 7.80 (d, J=5.3 Hz, 1H), 8.06 (d, J=8.1 Hz, 2H), 8.28 (d, J=5.3 Hz, 1H), 8.89 (br, 1H), 10.94 (br, 1H).

DEPTq (500 MHz, DMSO-$d_6$): δ=21.9, 48.2, 110.9, 114.3, 117.8, 121.6, 123.0, 128.6, 140.2, 141.6, 143.5, 149.2, 152.8, 160.9.

Step c) Preparation of 3a-Hydroxy-1-phenyl-1H,2H, 3H,3aH,4H-pyrrolo[2,3-b]1,7-naphthyridin-4-one (Compound 1)

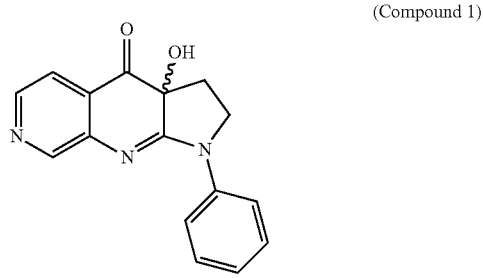 [SMILES: O=C1c2ccncc2N=C2N(c3ccccc3)CCC12O]

(Compound 1)

263 mg (1 mmol) of 1-phenyl-1H,2H,3H,4H,9H-pyrrolo[2,3-b]1,7-naphthyridin-4-one (Compound 1b) was suspended in dry tetrahydrofuran (40 ml) and under argon it is cooled with a dry ice-acetone mixture. A solution of 334 mg (1.8 ml, 2 mmol, 2 eq.) lithium hexamethyldisilazane in 20 weight % tetrahydrofuran was added below −60° C. 2-(Benzenesulfonyl)-3-phenyloxaziridine (522 mg, 2 mmol, 2 eq.) was then added, dissolved in dry tetrahydrofuran (15 mL). After half an hour, cooling was stopped and the mixture allowed to warm to room temperature, stirring overnight. To the reaction mixture 1 M HCl (40 mL) was added, and it was extracted with methyl-tert-butyl-ether (3×40 mL). The aqueous phase is concentrated under vacuum to ca. half of its volume, and then neutralized with $NaHCO_3$. The precipitated orange precipitate was filtered through a glass filter P4, washed with methyl-tert-butyl-ether and dried in vacuo. Yield: 131 mg (0.47 mmol, 47%) orange powder, 3α-hydroxy-1-phenyl-1H,2H,3H,3aH,4H-pyrrolo[2,3-b]1,7-naphthyridin-4-one (Compound 1). $M+H^+=280.30$ $^1H$ NMR (500 MHz, DMSO-$d_6$): δ=2.28 (dd, J=5.8, 13.3 Hz, 1H), 2.39 (ddd, J=9.2, 9.4, 13.3 Hz, 1H), 4.00 (dd, J=9.2, 10.3 Hz, 1H), 4.13 (ddd, J=5.8, 9.4, 10.3 Hz, 1H), 7.04 (s, 1H), 7.20 (t, J=7.5 Hz, 1H), 7.46 (t, J=7.9 Hz, 2H), 7.56 (d, J=4.5 Hz, 1H), 8.07 (d, J=8.0 Hz, 2H), 8.32 (br, 1H), 8.56 (br, 1H).

DEPTq (500 MHz, DMSO-$d_6$): δ=27.8, 47.8, 73.7, 118.2, 120.3, 124.2, 125.9, 128.7, 140.1, 143.8, 145.9, 148.1, 166.9, 193.9.

Preparation of 2-(benzenesulfonyl)-3-phenyloxaziridine: Org. Synth. 1988, 66, 203.

Example 2: Preparation of 9-Hydroxy-12-phenyl-4-thia-2,12-diazatricyclo[7.3.0.0$^{3,7}$]dodeca-1,3 (7), 5-trien-8-one (Compound 2)

Step a) Preparation of methyl 2-{[(2E)-1-phenylpyrrolidin-2-ylidene]amino}thiophene-3-carboxylate (Compound 2a)

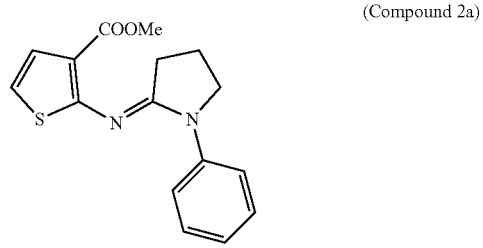 [SMILES: COC(=O)c1ccsc1/N=C1\CCCN1c1ccccc1]

(Compound 2a)

9.23 g (57.26 mmol, 1 eq.) of 1-phenylpyrrolidin-2-one was dissolved in 70 ml of dry dichloromethane and 8.78 g (5.3 ml, 57.26 mmol, 1 eq.) $POCl_3$ is added under argon. After stirring for three hours at room temperature, a suspension of methyl-2-aminothiophene-3-carboxylate (10 g, 63.61 mmol) in dichloromethane (150 mL) was added via a funnel. The reaction mixture was refluxed for 16 hours, cooled to room temperature, and extracted with 1M hydrochloric acid (5×100 mL). The combined aqueous phases were adjusted to pH 9-10 with saturated $Na_2CO_3$ solution. The mixture was extracted with dichloromethane (3×200 mL) and the combined organic layers were dried over $Na_2SO_4$. After filtering off the desiccant, after evaporation, 8.39 g of crude product remained. This was purified on a silica gel column with hexane-ethyl acetate. The appropriate fractions were combined and the residue was recrystallized from heptane:ethyl-acetate 1:1 mixture. Yield: 5.27 g (17.53 mmol, 31%) of methyl 2-{[(2E)-1-phenylpyrrolidin-2-ylidene]amino}thiophene-3-carboxylate (Compound 2a), pale yellow crystals.

$^1$H NMR (500 MHz, DMSO-$d_6$): δ=2.05 (m, 2H), 2.68 (t, J=7.8 Hz, 2H), 3.70 (s, 3H), 3.92 (t, J=7.0 Hz, 2H), 6.91 (d, J=6.0 Hz, 1H), 7.12 (tt, J=1.1, 7.5 Hz, 1H), 7.13 (d, J=6.0 Hz, 1H), 7.37 (dd, J=7, 5, 8.8 Hz, 2H), 7.83 (d, J=8.8 Hz, 2H).

DEPTq (500 MHz, DMSO-$d_6$): δ=19.1, 29.3, 50.8, 50.9, 115.3, 115.7, 121.0, 123.7, 127.0, 128.3, 140.4, 162.3, 163.0, 163.5.

Step b) Preparation of 12-Phenyl-4-thia-2,12-diazatricyclo[7.3.0.0$^{3,7}$]dodeca-1(9),3(7),5-trien-8-one (Compound 2b)

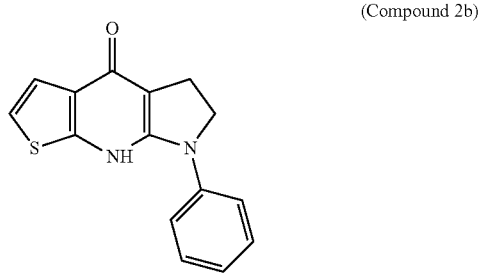 [SMILES: O=c1c2c([nH]c3sccc13)N(c1ccccc1)CC2]

(Compound 2b)

Methyl 2-{[(2E)-1-phenylpyrrolidin-2-ylidene]amino}thiophene-3-carboxylate (Compound 2a) (3.38 g, 12.75 mmol) was dissolved in dry tetrahydrofuran (50 mL). To this was added a solution of 2.86 g of potassium-tert-butylate (14 ml, 25.51 mmol, 2 eq.) in tetrahydrofuran, and then the reaction mixture was refluxed under argon. After the addition of the base, the solution becomes red and after a few minutes precipitate out. The reaction was followed by LCMS. After refluxing for three hours, the mixture was cooled to room temperature and 5 ml of acetic acid was added with stirring to dissolve the precipitate. The mixture was concentrated in vacuo to leave a brown sticky material, which was triturated with a mixture of 30 mL of MeOH and 30 mL of toluene 3 times to leave a crystalline material. This was stirred with water (30 mL), filtered and washed with water. 3.25 g of crude product is obtained, which is crystallized from 14 g of acetonitrile and dried in vacuo at 40° C. Yield: 2.16 g (8.06 mmol, 63%) of 12-phenyl-4-thia-2,12-diazatricyclo[7.3.0.0$^{3,7}$]dodeca-1(9),3(7),5-trien-8-one (Compound 2b), which is a pale brown powder. M+H$^+$=269.00

$^1$H NMR (500 MHz, DMSO-$d_6$): δ=3.10 (t, J=8.4 Hz, 2H), 4.07 (t, J=8.4 Hz, 2H), 6.96 (t, J=7.4 Hz, 1H), 7.22 (d, J=6.0 Hz, 1H), 7.36 (d, J=6.0 Hz, 1H), 7.35 (t, J=7.5 Hz, 2H), 7.86 (d, J=8.2 Hz, 2H), 10.60 (br, 1H).

DEPTq (500 MHz, DMSO-$d_6$): δ=21.5, 48.8, 104.8, 116.8, 118.4, 118.6, 118.7, 120.5, 128.5, 142.1, 154.2, 159.6, 160.1.

Step c) 9-Hydroxy-12-phenyl-4-thia-2,12-diazatricyclo[7.3.0.0$^{3,7}$]dodeca-1,3(7),5-trien-8-one (Compound 2)

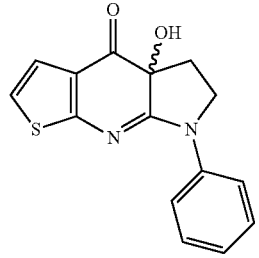

(Compound 2)

526 mg (1.96 mmol) of 12-phenyl-4-thia-2,12-diazatricyclo[7.3.0.0$^{3,7}$]dodeca-1(9),3(7),5-triene-8-one (Compound 2b) and 30 ml of dry tetrahydrofuran was weighed into a septum-filled round-bottomed flask and an argon balloon was placed on it. A thermometer and a plug were placed on the other two necks of the flask. The vessel was cooled with a dry ice-acetone mixture and a solution of 656 mg of lithium-hexamethyldisilazane (3.6 mL, 3.92 mmol, 2 eq.) in tetrahydrofuran was added via syringe below −60° C. A solution of 2-(benzenesulfonyl)phenyloxaziridine (563 mg, 2.15 mmol, 1.1 eq.) in dry tetrahydrofuran (5 mL) was then added below −60° C. Then it was let warm for 1 hour. After a few hours a yellow precipitate appears. The reaction mixture was stirred at room temperature overnight. Check the reaction by thin-layer chromatography. When the starting material was consumed, 40 ml of 2 M hydrochloric acid and 40 ml of methyl-tert-butyl-ether were added and shaken. The organic layer was extracted with 1M hydrochloric acid (3×40 mL) and the combined aqueous phases were extracted with 30 mL of methyl-tert-butyl-ether. The aqueous phase was extracted with dichloromethane (3×40 mL), the organic phases were combined, dried over $Na_2SO_4$, filtered and evaporated. The crude product was crystallized from acetonitrile. Yield: 207 mg (0.73 mmol, 37%) of 9-hydroxy-12-phenyl-4-thia-2,12-diazatricyclo[7.3.0.0$^{3,7}$]dodeca-1,3(7),5-triene-8-one (Compound 2), orange crystals. M+H$^+$=285.00

$^1$H NMR (500 MHz, DMSO-$d_6$): δ=2.25 (m, 2H), 4.04 (m, 1H), 4.17 (m, 1H), 6.93 (s, 1H), 6.96 (d, J=5.4 Hz, 11-1), 7.10 (d, J=5.4 Hz, 11-1), 7.21 (t, J=7.5 Hz, 11-1), 7.46 (t, J=7.5 Hz, 2H), 7.95 (d, J=8.0 Hz, 2H).

DEPTq (500 MHz, DMSO-$d_6$): δ=28.5, 49.0, 74.5, 117.2, 119.9, 120.4, 122.3, 124.7, 128.8, 139.6, 169.3, 170.6, 187.8.

Example 3: 7-Hydroxy-4-phenyl-10-thia-2,4-diazatricyclo[7.3.0.0$^{3,7}$]dodeca-1 (9),2.11-triene-8-one (Compound 3)

Step a) Preparation of methyl 3-{[(2E)-1-phenylpyrrolidin-2-ylidene]amino}thiophene-2-carboxylate (Compound 3a)

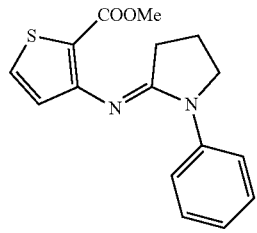

(Compound 3a)

5.00 g (31.02 mmol, 1 eq) of 1-phenylpyrrolidin-2-one was dissolved in 35 ml of dry dichloromethane and 4.76 g (2.83 ml, 31.02 mmol, 1 eq.) of POCl$_3$ was added. After stirring for 3 hours under argon, a solution of 5.42 g (34.46 mmol, 1.1 eq.) of methyl-3-aminothiophene-2-carboxylate in 35 ml of dichloromethane was added. The reaction mixture was then refluxed for 16 hours. 10% Na$_2$CO$_3$ solution was added so that the pH of the aqueous phase is about 8-9 after 5 minutes of stirring. The aqueous phase was extracted with dichloromethane (3×50 mL) and the organic phases were combined and then evaporated. The crude product thus obtained was dissolved in 50 ml of isopropyl-acetate and extracted with 5×40 ml of 1 M hydrochloric acid. The pH of the aqueous phases was adjusted to 8 with 10% Na$_2$CO$_3$ and extracted with dichloromethane (3×50 mL). After drying over Na$_2$SO$_4$, the solution was filtered and concentrated to ca. 2 ml. 20 ml of heptane is then added and evaporation is continued until a colorless plate crystals appear in the cloudy solution. These were filtered off, washed with heptane and dried in vacuo. Yield: 2.78 g (9.24 mmol, 30%), methyl 3-{[(2E)-1-phenylpyrrolidin-2-ylidene]amino}thiophene-2-carboxylate (Compound 3a). M+H$^+$=301.10

$^1$H NMR (500 MHz, DMSO-d$_6$): δ=1.99 (m, 2H), 2.50 (m, 2H), 3.71 (s, 3H), 3.86 (t, J=6.8 Hz, 2H), 6.70 (d, J=5.2 Hz, 1H), 7.07 (tt, J=1.1, 7.5 Hz, 1H), 7.35 (dd, J=7, 5, 8.5 Hz, 2H), 7.72 (d, J=5.2 Hz, 1H), 7.86 (d, J=8.5 Hz, 2H).

DEPTq (500 MHz, DMSO-d$_6$): δ=19.1, 29.3, 50.2, 51.2, 111.9, 120.4, 122.9, 125.5, 128.2, 131.3, 141.0, 157.1, 160.4, 162.0.

Step b) 4-Phenyl-10-thia-2,4-diazatricyclo[7.3.0.0$^{3,7}$]dodeca-1(9),3(7),11-triene-8-one (Compound 3b)

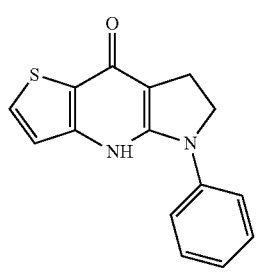

(Compound 3b)

To methyl-3-{[(2E)-1-phenylpyrrolidin-2-ylidene]amino}thiophene-2-carboxylate (2.51 g, 8.35 mmol), 32 ml of dry tetrahydrofuran, followed by 1.87 g (10.3 ml, 16.69 mmol, 2 eq) of a solution of potassium-tert-butylate in tetrahydrofuran were added. The reaction mixture was refluxed under argon for 3 hours (monitored using TLC). After cooling, 20 ml of 1 M hydrochloric acid was added and the tetrahydrofuran was evaporated in vacuo. Saturated NaHCO$_3$ solution was added to the aqueous residue until neutral pH and stirred for half an hour, then filtered, washed with water (2×10 mL) and dried in vacuo. Yield: 2.05 g (7.65 mmol, 92%) 4-phenyl-10-thia-2,4-diazatricyclo[7.3.0.0$^{3,7}$]dodeca-1(9),3(7),11-triene-8 (Compound 3b).

$^1$H NMR (500 MHz, DMSO-d$_6$): δ=3.15 (dd, J=7.9, 8.2 Hz, 2H), 4.07 (t, J=8.4 Hz, 2H), 6.96 (t, J=7.3 Hz, 1H), 7.27 (d, J=5.4 Hz, 1H), 7.35 (dd, J=7.7, 8.5 Hz, 2H), 7.76 (d, J=5.4 Hz, 1H), 7.92 (d, J=8.5 Hz, 2H), 11.0 (w, 1H).

DEPTq (500 MHz, DMSO-d$_6$): δ=22.0, 48.9, 104.8, 115.9, 117.0, 120.5, 124.1, 128.0, 128.5, 142.3, 154.1, 160.2.

Step c) 7-Hydroxy-4-phenyl-10-thia-2,4-diazatricyclo[7.3.0.0$^{3,7}$]dodeca-1(9),2,11-triene-8-one (Compound 3)

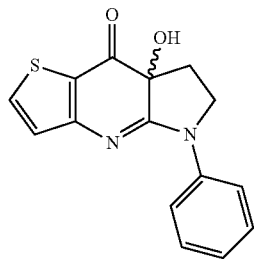

(Compound 3)

537 mg (2 mmol, 1 eq.) of 4-Phenyl-10-thia-2,4-diazatricyclo[7.3.0.0$^{3,7}$]dodeca-1(9),3(7),11-triene-8-one (Compound 3b) and 784 mg (3 mmol, 1.5 eq.) of 2-(benzenesulfonyl)-3-phenyloxaziridine and 20 mL of dry tetrahydrofuran are poured into a septum-sealed vessel. The vessel was sealed and a balloon filled with argon was placed in the septum. The solution was cooled with ice water and via syringe a solution of 669 mg (3.6 mL, 4 mmol, 2 eq.) of lithium-hexamethyldisilazane in 20% tetrahydrofuran was added to the solution in 1 minute. The solution was allowed to warm to room temperature and stirred overnight. The solution had a bright yellow precipitate after 1 hour. 40 ml of methyl-tert-butyl-ether and 40 ml of 2M hydrochloric acid are then added and shaken. The organic phase was extracted twice more with 20 ml of 2 M hydrochloric acid and the combined aqueous phases were adjusted to pH=8 with 40% NaOH. The mixture was extracted with 2-methyl-tetrahydrofuran (3×40 mL) and the organic layer was dried over Na$_2$SO$_4$, filtered and evaporated. The crude product was crystallized from acetonitrile. Yield: 333 mg (1.17 mmol, 59%) of 7-hydroxy-4-phenyl-10-thia-2,4-diazatricyclo[7.3.0.0$^{3,7}$]dodeca-1(9),2,11-triene-8-one (Compound 3), bright yellow crystals. M+H$^+$=285.00

$^1$H NMR (500 MHz, DMSO-d$_6$): δ=2.23 (dd, J=5.8, 12.9 Hz, 1H), 2.29 (ddd, J=8.0, 9.8, 12.9 Hz, 1H), 4.02 (dd, J=8.0, 9.5 Hz, 1H), 4.15 (ddd, J=5.8, 9.5, 9.8 Hz, 1H), 6.94 (s, 1H), 7.05 (d, J=5.1 Hz, 1H), 7.19 (tt, J=1.1, 7.4 Hz, 1H), 7.44 (tdd, J=2.1, 7.4, 8.8 Hz, 2H), 8.01 (td, J=1.1, 8.8 Hz, 2H), 8.03 (d, J=5.1 Hz, 1H).

DEPTq (500 MHz, DMSO-d$_6$): δ=28.2, 48.7, 75.2, 117.2, 120.3, 124.3, 126.2, 128.7, 136.8, 140.0, 161.4, 170.7, 186.9.

Example 4A: Synthesis of pyrrolotienopyridine and pyrrolonaphthyridine derivatives 4A.1 Preparation of 1-[(4-methoxyphenyl)methyl] pyrrolidin-2-one 4-Chloro-N-[(4-methoxyphenyl) methyl]-butanamide

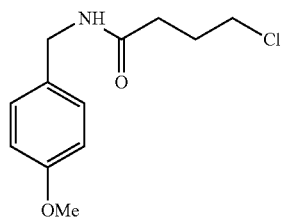 [SMILES: COc1ccc(CNC(=O)CCCCl)cc1]

To 768 g (554 mmol, 1 eq.) of 4-methoxybenzylamine in 370 ml of dry dichloromethane in an inert flask under argon, 93 ml (67.34 g, 665 mmol, 1.2 eq.) of triethylamine and 39 g (28 mmol, 5 mol %) of N,N-dimethylaminopyridine were added and the reaction mixture was cooled to 5° C. A solution of 4-chlorobutyryl-chloride (68.5 mL, 86.02 g, 610 mmol, 1.1 eq.) in 40 mL of dry dichloromethane was added dropwise to the reaction mixture at 5-15° C. The mixture was allowed to warm to room temperature and then stirred at room temperature for 24 hours. The mixture was washed with water (400 mL), 5% citric acid solution (2×400 mL) and saturated solution of NaHCO$_3$ (100 mL) and separated. The organic layer was dried over Na$_2$SO$_4$. The solution was then filtered, evaporated and the precipitated crystals were stirred with 200 ml of heptane overnight. It is then filtered through a glass filter, washed with cold heptane and then dried at 40° C. under vacuum. Yield: 107.27 g of white solid (443 mmol, 80%). Rf=0.66 dichloromethane:methanol 95:5.

$^1$H NMR (CDCl3, 500 MHz): δ 2.12 (m, 2H), 2.37 (t, J=7.2 Hz, 2H), 3.60 (t, J=6.2 Hz, 2H), 4.36 (d, J=5.6 Hz, 2H), 5.87 (bs, 1H), 6.86 (d, J=8.6 Hz, 2H), 7.19 (d, J=8.6 Hz, 2H).

13C DEPTq NMR (CDCl3, 500 MHz): δ 28.3, 33.4, 43.3, 44.7, 114.1, 114.3, 129.3, 130.4, 159.2, 171.5.

1-[(4-methoxyphenyl)methyl]pyrrolidin-2-one

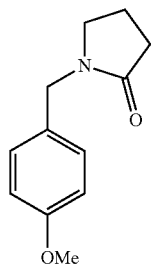 [SMILES: COc1ccc(CN2CCCC2=O)cc1]

In an inert flask under argon atmosphere, 105.00 g (434 mmol, 1 eq.) of 4-chloro-N-[(4-methoxyphenyl)methyl]butanamide was dissolved in 330 ml of dry tetrahydrofuran, and dropwise 321 ml of 20.1% by weight potassium-tert-butylate solution (58.49 g, 521 mmol, 1.2 eq.) in tetrahydrofuran was added, and the dropping funnel was washed with 40 ml of tetrahydrofuran into the flask. The reaction was exothermic and warmed up to boiling. The addition is controlled so that the reaction mixture remains in mild reflux. The mixture was then stirred at reflux for 2 hours. The reaction was monitored by thin layer chromatography. 15 ml (15.74 g, 262 mmol, 0.6 eq.) of acetic acid was added to the cooled reaction mixture. An exothermic reaction then occurred. Water (60 mL) is then added and the solution is decanted from the solid residue. The solid was washed with 50 ml of methyl-tert-butyl-ether and the combined organic phases were evaporated. The residue was dissolved in 200 ml of methyl-tert-butyl-ether and then extracted with saturated NaHCO$_3$ (100 ml) solution. The pH of the aqueous phase was adjusted to 8. The organic phase is then separated. The aqueous phase was further extracted with 100 ml of ethyl acetate and the combined organic layers were dried over 100 ml of NaCl and then with Na$_2$SO$_4$. The solvent was then evaporated in vacuo. The product can be purified by vacuum distillation, mp 151-158° C., 0.64 mbar. Yield: 77.03 g (375 mmol, 86%). Rf=0.24-0.56 patch, dichloromethane:methanol 95:5. Detection: alkaline KMnO$_4$ solution. ESI-MS (M+H$^+$)=206 $^1$H NMR (DMSO-d$_6$, 500 MHz): δ 1.97 (m, 2H), 2.42 (t, J=8.1 Hz, 2H), 3.24 (t, J=7.1 Hz, 2H), 3.79 (s, 3H), 4.38 (s, 2H), 6.85 (d, J=8.7 Hz, 2H), 7.17 (d, J=8.7 Hz, 2H).

$^{13}$C DEPTq NMR (DMSO-d$_6$, 500 MHz): δ 17.8, 31.2, 46.1, 46.6, 55.4, 114.2, 128.9, 129.6, 159.2, 174.9.

Preparation of 4A.2 1-[4-(morpholin-4-yl)phenyl] pyrrolidin-2-one 4-chloro-N-[4-(morpholin-4-yl) phenyl]butanamide

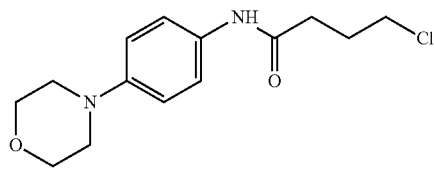 [SMILES: O=C(CCCCl)Nc1ccc(N2CCOCC2)cc1]

To a three-necked one-liter round-bottomed flask was charged 26.72 g (150 mmol, 1 eq.) of 4-(aminophenyl)-morpholine, 25 mL (18.20 g, 180 mmol, 1.2 eq.) of triethylamine and 260 mL dry dichloromethane. A flask was equipped with a dripping top, a CaCl$_2$ tube and a thermometer and then the flask was cooled to 5-10° C. with ice water. Then, 5-chloro-butyric-acid-chloride (18.5 mL, 23.27 g, 165 mmol, 1.1 eq.) was added at 5-10° C. over 1 hour 25 minutes. A precipitate forms at the end of the addition. The reaction was monitored by thin layer chromatography. After consuming the starting material (1 hour and 15 minutes after the end of the addition), saturated NaHCO$_3$ solution (170 ml) was added slowly (foaming!). After stirring for 10 minutes, the organic phase was separated with the precipitate and evaporated. The crude product was recrystallized from 300 ml of ethanol by adding 5 spoons of charcoal. Yield: 20.53 g (72.60 mmol, 48%). ESI-MS (M+H$^+$)=283. Rf=0.47 dichloromethane:methanol 10:2.

$^1$H NMR (DMSO-d$_6$, 500 MHz): δ 2.01 (m, 2H), 2.43 (t, J=7.3 Hz, 2H), 3.02 (m, 4H), 3.69 (t, J=6.6 Hz, 2H), 3.72 (m, 4H), 6.87 (d, J=9.1 Hz, 2H), 7.44 (d, J=9.1 Hz, 2H), 9.72 (s, 1H).

$^{13}$C DEPTq NMR (DMSO-d$_6$, 500 MHz): δ 28.0, 33.2, 45.0, 49.0, 66.1, 115.4, 120.2, 131.5, 147.0, 169.4.

1-[4-(morpholin-4-yl)phenyl]pyrrolidin-2-one

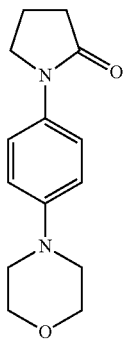 [SMILES: O=C1CCCN1c1ccc(N2CCOCC2)cc1]

18.64 g (65.92 mmol, 1 eq.) of 4-chloro-N-[4-(morpholin-4-yl)phenyl]butanamide was dissolved in 140 ml of dry tetrahydrofuran in a 250 ml three-necked round-bottomed flask. The flask was equipped with a thermometer, dripping top and reflux condenser, the cooler was equipped with a septum and a balloon filled with argon. To this solution was slowly added potassium-tert-butylate (49 ml, 20.1%) (8.88 g KOtBu, 79.10 mmol, 1.2 eq.) in tetrahydrofurane. The solution is then boiled until the starting material is consumed. The reaction was monitored by thin layer chromatography. Water (50 ml) and saturated NaCl (50 ml) were then added, and the mixture was shaken and separated. The aqueous phase was extracted with 2-methyl-tetrahydrofuran (3×50 mL). The combined organic phases are dried over $Na_2SO_4$, filtered and concentrated. The material, together with the crystals precipitated during the extraction were recrystallized from 80 g of ethanol. Yield: 12.76 g (51.82 mmol, 79%) of white crystals. ESI-MS (M+H$^+$)=247. Rf=0.30 isopropyl-acetate:methanol 10:1+1% TEA.

$^1$H NMR (DMSO-d$_6$, 500 MHz): δ 2.03 (m, 2H), 2.44 (t, J=8.0 Hz, 2H), 3.06 (m, 4H), 3.73 (m, 4H), 3.77 (t, J=7.0 Hz, 2H), 6.93 (d, J=9.1 Hz, 2H), 7.48 (d, J=9.1 Hz, 2H).

$^{13}$C DEPTq NMR (DMSO-d$_6$, 500 MHz): δ 17.4, 32.0, 48.2, 48.7, 66.0, 115.1, 120.6, 131.8, 147.6, 173.0.

4A.3 Preparation of 4-(4-iodophenyl)morpholine

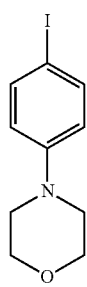 [SMILES: Ic1ccc(N2CCOCC2)cc1]

25 g (140 mmol, 1 eq.) of 4-(4-aminophenyl)morpholine were dissolved in 300 ml of dry acetonitrile in a 500 ml three-necked round-bottomed flask. A thermometer, drip top and reflux condenser were placed on the flask, and a silicone oil scrubber was placed on the cooler. To the solution diiodomethane (34 mL, 112.7 g, 420 mmol, 3 eq) was added. Argon was slowly passed through the apparatus and 28 ml (26.19 g, 210 mmol, 1.5 eq.) of 90% tert-butyl-nitrite was added under stirring at room temperature. After stirring for 1 hour at room temperature, the mixture was stirred at 60° C. for 2 hours and 40 minutes. At this point, the thin layer chromatography no longer shows the starting material. The reflux condenser is then replaced by a 20 cm Vigreux column and distillation column and the volatiles are distilled off under vacuum. The residue was dissolved in 200 ml of dichloromethane and extracted with 20 ml of saturated NaHCO$_3$ and 20 ml of 10% Na$_2$S$_2$O$_3$. The organic layer was separated, evaporated to 100 mL and filtered through silica gel with (150 g) dichloromethane. Wash with dichloromethane until the product is detected in the filtrate by TLC. After evaporation, 24.12 g of crude product was obtained, which is recrystallized from 280 g of acetone. Yield: 18.28 g (63 mmol, 45%) of pale yellow crystals. Rf=0.53 ethyl-acetate:cyclohexane 2:1.

$^1$H NMR (DMSO-d$_6$, 500 MHz): δ 3.08 (t, J=5.0 Hz, 4H), 3.71 (t, J=5.0 Hz, 4H), 6.77 (d, J=9.0 Hz, 2H), 7.50 (d, J=9.0 Hz, 2H).

$^{13}$C DEPTq NMR (DMSO-d$_6$, 500 MHz): δ 47.8, 65.9, 80.9, 117.4, 137.2, 150.6.

4A.4 Preparation of 9-Hydroxy-12-[4-(morpholin-4-yl)phenyl]-4-thia-2,12-diazatricyclo[7.3.0.0$^{3,7}$]dodeca-1,3 (7),5-triene-8-on Methyl-2-{[(2E)-1-[4-(morpholin-4-yl)phenyl]pyrrolidin-2-ylidene]amino}thiophene carboxylate

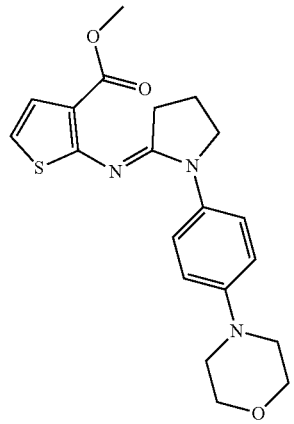 [SMILES: COC(=O)c1ccsc1/N=C1\CCCN1c1ccc(N2CCOCC2)cc1]

In an inert three-necked flask under argon, 7.11 g (28.89 mmol, 1 eq.) of 1-[4-(morpholin-4-yl)phenyl]pyrrolidin-2-one was dissolved in 40 ml of dry dichloromethane. The flask was equipped with a dripping top, a reflux condenser, and a CaCl$_2$) tube was placed on the top of the flask. A solution of 4.9 ml (8.15 g, 28.89 mmol, 1 eq.) of trifluoromethanesulfonic acid-anhydride in 5 ml of dry dichloromethane was added dropwise at room temperature over 5 minutes. The temperature rose to 35° C. and the mixture was then allowed to cool to room temperature. In a few minutes, black tar was released, then a solution of 4.99 g (31.78 mmol, 1.1 eq.) of 2-aminothiophene-3-carboxylic-acid-methyl-ester in 40 ml of dry dichloromethane was added over 5 minutes. The reaction mixture was stirred at reflux for 24 hours. To the cooled reaction mixture was slowly added 60 mL of saturated Na$_2$CO$_3$ solution and it was stirred for 10-15 minutes. After separation of the phases, the organic phase is concentrated. Dry over Na$_2$SO$_4$, filter and evaporate. The residue was used without further purification. Yield: 10.00 g of dark brown oil, crude product. LCMS (M+H$^+$)=386.

12[4-(morpholin-4-yl)phenyl]-4-thia-2,12-diazatricyclo[7.3.0.0³,⁷]dodeca-1(9),3(7),5-trien-8-one

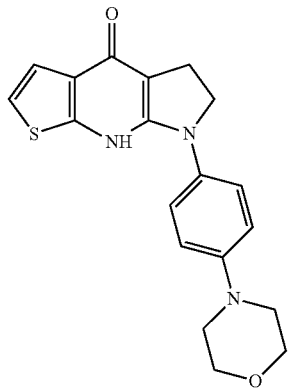 [SMILES: O=c1c2c([nH]c3sccc13)N(c1ccc(N3CCOCC3)cc1)CC2]

The crude methyl 2-{[(2E)-1-[4-(morpholin-4-yl)phenyl]pyrrolidin-2-ylidene]amino}thiophene-3-carboxylate obtained in the previous reaction was dissolved in 50 ml of dry tetrahydrofuran and poured in a three-necked round bottom flask. The flask was equipped with a dripping top and a reflux condenser, the latter with a $CaCl_2$ tube. The apparatus was made inert with argon and 32 ml of 20.1% by weight potassium-tert-butylate solution (5.82 g KOtBu, 51.88 mmol) was added dropwise from dripping top over 5 minutes. The solution was then boiled for six hours. It is then cooled and neutralized and evaporated. The residue was purified by column chromatography on 80x weight silica gel with ethyl acetate containing 1% pyridine-acetic acid-water 20:6:1 mixture. Yield 976 mg (2.76 mmol, 9.6%). ESI-MS (M+H⁺)=354.

¹H-NMR δ (500 MHz DMSO-d₆ T=300K): 3.04 (m, 4H), 3.07 (t, J=8.3 Hz, 2H), 3.74 (m, 4H), 4.01 (t, J=8.3 Hz, 2H), 6.96 (d, J=9.1 Hz, 2H), 7.17 (d, J=6 Hz, 1H), 7.32 (d, J=6.0 Hz, 1H), 7.70 (d, J=9.1 Hz, 2H), 10.47 (s, 1H).

¹³C DEPTq NMR δ (126 MHz DMSO-d₆): 21.6, 49.1, 49.3, 66.1, 104.3, 115.7, 117.7, 117.9, 118.1, 118.7, 134.9, 145.5, 149.5, 153.8, 159.9, 160.3.

9-hydroxy-12-[4-(morpholin-4-yl)phenyl]-4-thia-2,12-diazatricyclo[7.3.0.0³,⁷]dodeca-1,3(7),5-trien-8-one (188)

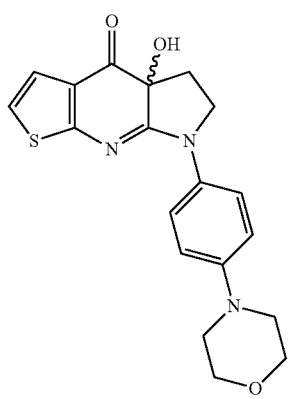 [SMILES: O=C1c2ccsc2N=C2N(c3ccc(N4CCOCC4)cc3)CCC12O]

600 mg (1.69 mmol, 1 eq.) of 12-[4-(morpholin-4-yl)phenyl]-4-thia-2,12-diazatricyclo[7.3.0.0³,⁷]dodeca-1(9),3(7),5-triene-8-one and 665 mg (2.55 mmol, 1.5 eq.) of 2-(benzenesulfonyl)-3-phenyloxaziridine were weighed into a screw glass jar. Dry tetrahydrofuran (30 ml) was added, it was made inert with argon and sealed with a septum cap. A balloon filled with argon was placed in the septum. The vessel is then cooled with ice water. 3.1 g of a 20.7% LiHMDS solution (568 mg LiHMDS, 3.39 mmol, 2 eq.) in tetrahydrofuran was added via syringe through the septum. Stir for 24 hours at room temperature. 40 ml of methyl-tert-butyl-ether and 40 ml of 2M hydrochloric acid were then added and shaken and separated. The organic layer was extracted twice with 20 ml of 2M hydrochloric acid and the combined aqueous phases were extracted with 40 ml of methyl tert-butyl-ether. The aqueous phase was neutralized with 10% $Na_2CO_3$ (foaming!). Meanwhile, an orange precipitate forms. This was filtered, washed with water and dried under vacuum at 40° C. Yield: 230 mg (0.62 mmol, 37%). A further 250 mg product can be extracted from the aqueous phase with 3×40 ml of 2-methyl-tetrahydrofuran. The combined yield was 488 mg (1.32 mmol, 49%). ESI-MS (M+H+)=370.

¹H-NMR δ (500 MHz DMSO-d₆ T=300K): 2.22 (m, 2H), 3.12 (m, 4H), 3.75 (m, 4H), 3.99 (m, 1H), 4.13 (m, 1H), 6.85 (s, 1H), 6.88 (d, J=5.7 Hz, 1H), 7.02 (d, J=9.1 Hz, 2H), 7.06 (d, J=5.7 Hz, 1H), 7.77 (d, J=9.1 Hz, 2H).

¹³C DEPTq NMR δ (126 MHz DMSO-d₆): 28.7, 48.3, 49.3, 66.0, 74.6, 114.9, 116.4, 119.4, 121.7, 122.3, 131.4, 148.3, 168.7, 171.5, 187.7.

4A.5 Preparation of 5 9-Hydroxy-5-methyl-12-phenyl-4-thia-2,12-diazatricyclo [7.3.0.0³,⁷]dodeca-1,3(7),5-trien-8-one Methyl 5-methyl-2-{[(2E)-1-phenylpyrrolidin-2-ylidene]amino}thiophene-3-carboxylate

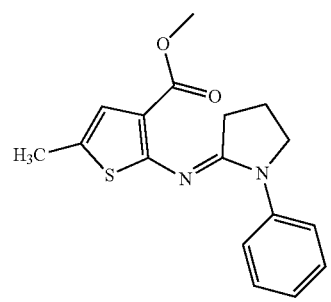 [SMILES: COC(=O)c1cc(C)sc1/N=C1\CCCN1c1ccccc1]

In an inert three-necked flask under argon, 5.00 g (31.02 mmol, 1 eq.) of 1-phenylpyrrolidin-2-one was dissolved in 35 ml of dry dichloromethane. A dripping top, a reflux condenser and a $CaCl_2$ tube were placed on the flask. A solution of trifluoromethanesulfonic anhydride (5.2 mL, 8.75 g, 31.02 mmol, 1 eq) in 5 mL of dry dichloromethane was added dropwise at room temperature over 5 minutes. The temperature rises to boiling, then allowed to cool to room temperature and stirred for 15 minutes. A solution of 4.99 g (31.78 mmol, 1.1 eq.) of 2-amino-5-methylthiophene-3-carboxylic acid-methyl-ester in 35 ml of dry dichloromethane was added dropwise over 5 minutes. The reaction mixture was stirred at reflux for 24 hours. To the cooled reaction mixture 100 mL of saturated $NaHCO_3$ solution was slowly added and stirred for 10-15 minutes (foaming!). After separation of the phases, the aqueous phase was extracted with 30 ml of dichloromethane. The combined organic layers were dried over Na$_2$SO$_4$, filtered and concentrated. The residue was used without further purification. Yield: 4.59 g of dark brown oil. ESI-MS (M+H$^+$)=315. Rf=0.52, cyclohexane:ethyl acetate 1:1.

5-methyl-12-phenyl-4-thia-2,12-diazatricyclo[7.3.0.0$^{3,7}$]dodeca-1 (9),2,5,7-tetraene-8-ol

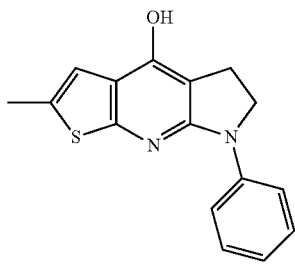 [SMILES: Cc1cc2c(O)c3c(nc2s1)N(c1ccccc1)CC3]

4.21 g (13.39 mmol, 1 eq.) of methyl-5-methyl-2-{[(2E)-1-phenylpyrrolidin ylidene]amino}thiophene-3-carboxylate was dissolved in 40 ml of dry tetrahydrofuran and poured into a three-necked round-bottomed flask. The flask was fitted with a dripping top and a reflux condenser, the latter with a CaCl$_2$) tube. The apparatus was made inert with argon and 15 ml of 20.1 weight % potassium-tert-butylate solution (2.73 g KOtBu, 24.34 mmol, 1.8 eq.) was added dropwise over 5 minutes. To calculate the base, the product of the previous step is considered pure. After refluxing for 5 hours, the mixture was cooled to room temperature and 60 ml of saturated NH$_4$Cl solution was added. The organic phase was then extracted with a saturated solution of NaCl (2×30 mL), separated and dried over Na$_2$SO$_4$. After filtration and evaporation, 3.87 g of brown solid remained, which was used without further purification. ESI-MS (M+H$^+$)=283. Rf=0.40 cyclohexane:ethyl acetate 1:1.

9-Hydroxy-5-methyl-12-phenyl-4-thia-2,12-diazatricyclo[7.3.0.0$^{3,7}$]dodeca-1,3 (7),5-triene-8-one (198)

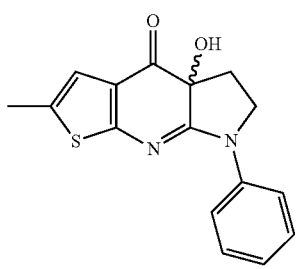

1.00 g (3.55 mmol, 1 eq.) of crude 5-methyl-12-phenyl-4-thia-2,12-diazatricyclo[7.3.0.0$^{3,7}$]dodeca-1(9),2,5,7-tetraen-8-ol and 1.39 g (5.32 mmol, 1.5 eq.) of 2-(benzenesulfonyl)-3-phenyloxaziridine were weighed into a 100 mL round bottom flask. Dry tetrahydrofuran (30 ml) was added, it was made inert with argon and sealed with septum. An argon filled balloon was placed in the septum. The vessel is then cooled with ice water. 6.5 ml of a 20.7% LiHMDS solution (1.19 g LiHMDS, 7.09 mmol, 2 eq.) in tetrahydrofuran was added via syringe. Yellow precipitate was formed. The reaction mixture was stirred at room temperature for 24 hours. 40 ml of methyl-tert-butyl-ether and 40 ml of 2M hydrochloric acid were then added. The organic layer was extracted twice with 20 ml of 2 M hydrochloric acid and the combined aqueous phases were concentrated in vacuo to leave the organic solvents. The aqueous phase was neutralized with saturated Na$_2$CO$_3$ solution (foaming!) and then adjusted to 8 with saturated NaHCO$_3$ solution. Meanwhile, a yellow precipitate forms. This was filtered, washed with water and dried under vacuum at 40° C. Yield: 574 mg (1.92 mmol, 54%). ESI-MS (M+H$^+$)=299. Rf=0.54 cyclohexane:ethyl acetate 1:1.

$^1$H NMR (500 MHz, DMSO-d6): δ=2.22 (m, 2H), 2.34 (s, 3H), 4.03 (m, 1H), 4.15 (m, 1H), 6.79 (d, J=1.0 Hz, 1H), 6.88 (s, 1H), 7.20 (t, J=7.4 Hz, 1H), 7.45 (dd, J$_1$=7.4, J$_2$=8.0 Hz, 2H), 7.93 (d, J=7.4 Hz, 2H).

$^{13}$C DEPTq (500 MHz, DMSO-d6): δ=15.1, 28.6, 48.9, 74.4, 119.6, 119.8, 120.3, 124.6, 128.8, 130.1, 139.6, 169.0, 169.2, 187.5.

4A.6 Preparation of 9-hydroxy-5-methyl-4-thia-2,12-diazatricyclo[7.3.0.0$^{3,7}$]dodeca-1,3(7),5-triene-8-one Methyl.2-{[(2E)-1-[(4-methoxyphenyl)methyl]pyrrolidin-2-ylidene]amino}-5-methylthiophene-3-carboxylate

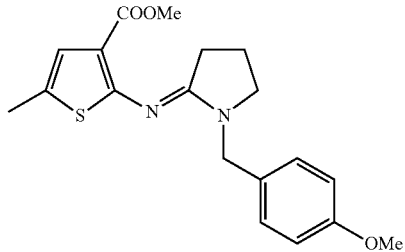 [SMILES: COC(=O)c1cc(C)sc1/N=C1\CCCN1Cc1ccc(OC)cc1]

In an inert flask under argon atmosphere, 1-[(4-methoxyphenyl)methyl]pyrrolidin-2-one (24.95 g, 121.54 mmol, 1 eq.) was dissolved in 100 ml of dry dichloromethane and cooled to 5-10° C. A solution of trifluoromethanesulfonic anhydride (20.45 ml, 34.29 g, 121.54 mmol, 1 eq.) in 20 ml of dry dichloromethane was added dropwise ca. in 20 minutes. Allow to warm to room temperature and stir for 1 hour. The reaction mixture was cooled to 5-15° C. and a solution of 22.89 g (133.7 mmol, 1.1 eq.) of 2-amino-5-methylthiophene-3-carboxylic acid-methyl-ester in 160 mL of dry dichloromethane was added dropwise to the mixture in 15 minutes. The reaction mixture was stirred at reflux for 24 hours. The reaction was monitored by thin layer chromatography (hexane:ethyl acetate 7:3). To the cooled reaction mixture was slowly added 140 ml of saturated Na$_2$CO$_3$ solution and stirred for 10-15 minutes (foaming!). After separation of the phases, the organic layer was washed with water (2×100 mL) and evaporated. The residue was dissolved in 100 ml of isopropyl-acetate and extracted with 10% citric acid (10×60 ml). The combined aqueous extract was washed with 60 mL of isopropyl-acetate. The aqueous phase was basified to pH-9 with saturated Na$_2$CO$_3$ (100 mL) and 50% NaOH (50 mL) and extracted with isopropyl-acetate (3×100 mL). The organic layer was dried over Na$_2$SO$_4$, filtered and concentrated. Yield: 20.1 g of yellow oil (56.07 mmol, 46%). ESI-MS (M+H$^+$)=359.

$^1$H-NMR (500 MHz DMSO-d$_6$ T=300K): δ 1.90 (m, 2H), 2.27 (d, J=1.2 Hz, 3H), 2.49 (t, J=7.3 Hz, 2H), 3.27 (t, J=7.3 Hz, 2H), 3.65 (s, 3H), 3.74 (s, 3H), 4.51 (s, 2H), 6.77 (q, J$_1$=1.2 Hz, 1H), 6.91 (m, J$_1$=8.6 Hz, 2H), 7.30 (m, J$_1$=8.6 Hz, 2H).

$^{13}$C DEPTq NMR δ (126 MHz DMSO-d$_6$): 15.0, 19.0, 27.9, 46.2, 48.1, 50.7, 55.0, 113.8, 114.7, 124.4, 126.8, 129.0, 129.2, 158.5, 163.0, 163.6

12-[(4-Methoxyphenyl)methyl]-5-methyl-4-thia-2,12-diazatricyclo[7.3.0.0$^{3,7}$]dodeca-1(9),2,5,7-tetraene-8-ol

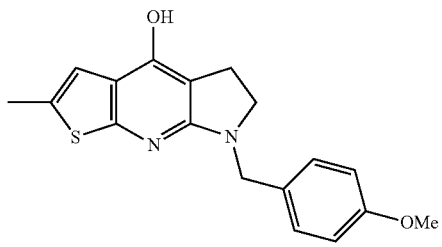 [SMILES: COc1ccc(CN2CCc3c2nc2sc(C)cc2c3O)cc1]

30.28 g (84.47 mmol, 1 eq.) of methyl-2-{[(2E)-1-[(4-methoxyphenyl)methyl]pyrrolidin-2-ylidene]amino}-5-methylthiophene-3-carboxylate was dissolved in 750 ml toluene and 500 ml of toluene was distilled off using a water separator. The residual solvent was evaporated in vacuo. In an inert flask under argon, the evaporation residue was dissolved in 340 ml of dry tetrahydrofuran, followed by addition of 94.31 g (18.96 g of KOtBu, 168.9 mmol, 2 eq.) a 20.1 m/m % solution of potassium-tert-butylate in tetrahydrofuran. The reaction mixture was stirred at reflux and the reaction was monitored by thin layer chromatography (hexane:ethyl acetate 7:3). After the starting material was consumed, 38 ml (39.9 g of 664.4 mmol, 7.8 eq.) of acetic acid were added to the cooled reaction mixture and the reaction mixture was concentrated in vacuo. The evaporation residue was suspended in 200 ml of toluene and the solvent was evaporated in vacuo and the residue was suspended in 300 ml of water. Subsequently, the pH of the mixture was adjusted to approx. 8 with saturated NaHCO$_3$ solution (600 mL) and stirred for at least 30 minutes. Filter on a glass filter, wash with 3×150 mL water, 3×150 mL methyl-tert-butyl-ether. The filtered material was dried in vacuo at room temperature. Yield: 18.83 g (57.69 mmol, 68.29%). ESI-MS (M+H$^+$)=327.

$^1$H-NMR δ (500 MHz DMSO-d$_6$ T=300K): 2.42 (s, 3H), 2.87 (t, J=8.3 Hz, 2H), 3.32 (t, J=8.3 Hz, 2H), 3.72 (s, 3H), 4.41 (s, 2H), 6.88 (d, p 8.4 Hz, 2H), 6.94 (s, 1H), 7.20 (d, J=8.4 Hz, 2H), 10.17(s, br, 1H).

$^{13}$C DEPTq NMR δ (126 MHz DMSO-d$_6$): 15.8, 22.5, 48.2, 48.9, 54.9, 102.2, 113.7, 116.4, 117.4, 129.2, 129.4, 129.8, 153.3, 158.3, 159.9, 163.0.

5-Methyl-4-thia-2,12-diazatricyclo[7.3.0.0$^{3,7}$]dodeca-1(9),2,5,7-tetraene-8-ol

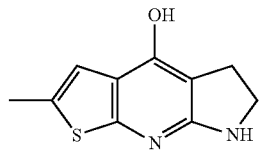

18.82 g (57.66 mmol, 1 eq.) of 12-[(4-methoxyphenyl)methyl]-5-methyl-4-thia-2,12-diazatricyclo[7.3.0.0$^{3,7}$]-dodeca-1(9),2,5,7-tetraen-8-ol and 62 ml (61.69 g, 570.46 mmol, 9.89 eq) of anisole were weighed in an inert flask under argon. Trifluoroacetic acid (35.5 mL, 52.56 g, 461.26 mmol, 8 eq.) was added dropwise at room temperature and the solution was stirred at 70° C. for 19 h. The reaction was monitored by thin layer chromatography (toluene:dioxane:acetic acid 10:3:1). After the starting material is consumed, the reaction mixture is cooled to 0-5° C. By the addition of 340 ml of cc. hydrochloric acid the hydrochloride salt of the product is precipitated. The suspension was stirred for 10-15 minutes and then filtered through a glass filter (from this first filtrate by alkalizing to pH-9, filtering, washing with aqueous and cold acetonitrile 4.65 g of product can be obtained), washed with 50 ml of cold acetonitrile and 50 ml of cold diethyl ether, and dried under vacuum at 30° C. The 7.76 g HCl salt thus obtained is suspended in 90 ml of saturated NaHCO$_3$ solution and stirred for 30 minutes. It was filtered, washed on a glass filter with 2×40 ml of water and 20 ml of methyl-tert-butyl-ether and then dried under vacuum. Yield: 11.33 g of white solid (54.93 mmol, 95.29%).

$^1$H-NMR δ (500 MHz DMSO-d$_6$ T=300K): 2.38 (s, 3H), 2.91 (t, J=6.2 Hz, 2H), 3.44 (t, J=6.2 Hz, 2H), 6.0-3.5 (s, br, 1H), 6.05 (s, br, 1H), 6.93 (s, 1H).

$^{13}$C DEPTq NMR δ (126 MHz DMSO-d$_6$): 15.8, 24.5, 44.0 101.8, 116.8, 117.8, 128.6, 154.7, 159.9, 165.3.

9-Hydroxy-5-methyl-4-thia-2,12-diazatricyclo[7.3.0.0$^{3,7}$]dodeca-1,3 (7),5-triene-8-one (231)

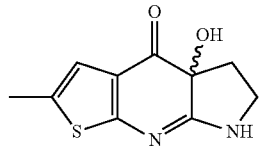

In an inert flask under argon, 3.0 g (14.55 mmol, 1 eq.) of 5-methyl-4-thia-2,12-diazatricyclo[7.3.0.0$^{3,7}$]dodeca-1(9),2,5,7-tetraen-8-ol and 5.70 g (21.81 mmol, 1.5 eq.) of 2-(benzenesulfonyl)-3-phenyloxaziridine was dissolved in 30 ml of dry tetrahydrofuran and cooled to 0-5° C. with stirring. A solution of 26.5 ml (23.51 g, 4.87 g, 29.09 mmol, 2 eq.) of LiHMDS in 20.7 m/m % tetrahydrofuran was added dropwise to the reaction mixture and allowed to warm to room temperature. The reaction was monitored by thin layer chromatography (toluene:dioxane:acetic acid 10:3:1). After completion of the reaction, 50 ml of saturated ammonium chloride solution was added to the reaction mixture. 150 ml of 2-methyl-tetrahydrofuran and 50 ml of water are added to remove the emulsion. After separation of the phases, the aqueous layer was extracted with methyl-tetrahydrofuran (4×50 mL). In the combined organic phase, the yellow powder precipitated was filtered through a glass filter and dried under vacuum (0.339 g). The organic filtrate was allowed to stand at room temperature overnight and separated from the aqueous phase. Dry over $Na_2SO_4$, filter, and evaporate under vacuum to ca. 100 ml. The precipitated product was filtered through a paper filter and washed with 2×0 mL 2-methyl-tetrahydrofuran, dried at 30° C. under vacuum (0.869 g). The filtrate was again concentrated to about 30 mL and the precipitated product was again filtered through a paper filter, dried under vacuum (1.265 g). Yield: 2.473 g (11.13 mmol, 76.56%). ESI-MS (M+H$^+$)=223.

$^1$H-NMR δ (500 MHz DMSO-d$_6$ T=300K): 2.02 (ddd, $J_1$=13.3 Hz, $J_2$=$J_3$=8.4 Hz, 1H), 2.12 (dd, $J_1$=13.3 Hz, $J_2$=5.2 Hz, 1H), 2.27 (d, J=0.9 Hz, 3H), 3.42 (dd, $J_1$=10.7 Hz, $J_2$=8.4 Hz, 1H), 3.57 (m, 1H), 6.57 (s, br, 1H), 6.64 (q, J=0.9 Hz, 1H), 8.96 (s, br, 1H).

$^{13}$C DEPTq NMR δ (126 MHz DMSO-d$_6$): 15.0, 31.6, 42.3, 72.9, 118.4, 119.3, 127.2, 174.1, 187.5.

4A.7 Preparation of 9-hydroxy-5-methyl-12-[4-(morpholin-4-yl)phenyl]-4-thia-2,12-diazatricyclo[7.3.0.0$^{3,7}$]dodeca-1,3(7)5-triene-8-one (220)

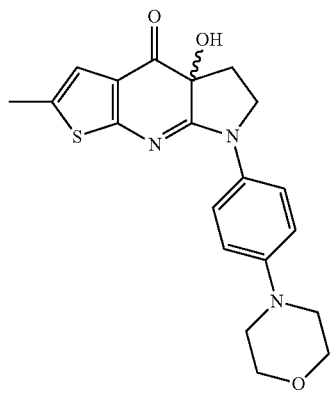 [SMILES: Cc1cc2c(s1)N=C1N(c3ccc(N4CCOCC4)cc3)CCC1(O)C2=O]

400 mg (1.80 mmol 1 eq.) of 9-hydroxy-5-methyl-4-thia-2,12-diazatricyclo[7.3.0.0$^{3.7}$]dodeca-1,3(7)5-triene-8-one were charged into a 100 ml round bottom flask, 412 mg (2.15 mmol, 1.2 eq) of copper(I)iodide, 304 mg (2.15 mmol, 1.2 eq.) of N,N'-dimethyl-cyclohexanediamine, 676 mg (3.60 mmol, 2 eq.) of 4-(4-iodophenyl)morpholine, 1.76 g (5.40 mmol, 3 eq.) of cesium-carbonate, 20 ml of dry N,N-dimethyl-formamide and 8 g dry molecular sieve. The cesium carbonate was previously dried at 120° C. with $P_2O_5$ under vacuum for 2 hours. The flask was made inert with nitrogen and sealed with septum. A balloon filled with nitrogen was placed in the septum. The reaction mixture was stirred at 60° C. until the starting material was consumed. The reaction was monitored by thin layer chromatography, eluting with ethyl acetate. After three days, the reaction no longer proceeds, the mixture is then cooled, filtered through Celite, washed with methanol until the filtrate is yellow. The methanol was evaporated in vacuo and the residue was poured into saturated NaCl (100 mL). This was extracted with 2-methyl-tetrahydrofuran (3×100 mL). When an emulsion is formed, another 100 ml of NaCl solution and 100 ml of 2-methyl-tetrahydrofuran were added. The combined organic phases were extracted with 50 ml of saturated NaCl solution, dried over $Na_2SO_4$, filtered and evaporated. 1.6 g of crude product was evaporated to 5 g of Celite and purified by column chromatography (silica gel, ethyl-acetate). The appropriate fractions were evaporated, triturated with diethyl ether, and the orange precipitate was filtered off. Yield: 308 mg. It is then purified, if necessary, by preparative HPLC. ESI-MS (M+H$^+$)=384.

$^1$H NMR (DMSO-d$_6$, 500 MHz): δ 2.20 (m, 2H), 2.32 (s, 3H), 3.11 (m, 4H), 3.74 (m, 4H), 3.97 (m, 1H), 4.10 (m, 1H), 6.75 (s, 1H), 6.80 (s, 1H), 7.02 (d, J=9.0 Hz, 2H), 7.76 (d, J=9.0 Hz, 2H).

$^{13}$C DEPTq NMR (DMSO-d$_6$, 500 MHz): δ 15.1, 28.8, 48.3, 49.1, 74.4, 114.9, 119.3, 119.5, 121.6, 129.2, 131.4, 148.2, 168.5, 170.2, 187.3.

4A.8 Preparation of 9-hydroxy-4-thia-2,12-diazatricyclo[7.3.0.0$^{3,7}$]dodeca-1,3(7),5-triene-8-one Methyl-2-{[(2E)-1-[(4-methoxyphenyl)methyl]pyrrolidin-2-ylidene]amino}thiophene-3-carboxylate

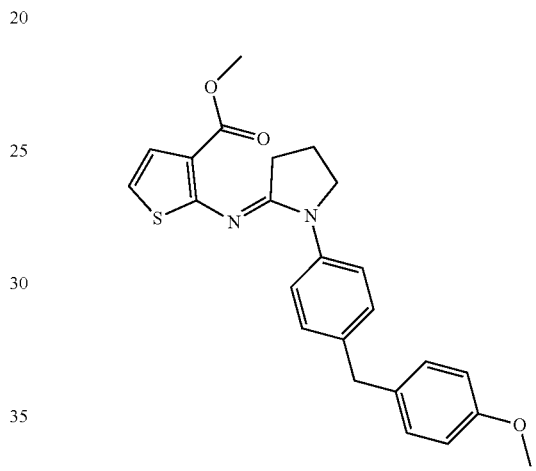

A dry 4-necked 500 ml round-bottomed flask was fitted with a magnetic stirring rod, equipped with a thermometer, dripping top, reflux condenser and gas inlet. On top of the reflux cooler, a gas washer filled with silicone oil and a $CaCl_2$ tube were placed. 25.02 g (122 mmol, 1 eq.) of 1-[(4-methoxyphenyl)methyl]pyrrolidin-2-one are added to the flask and dissolved in 150 ml of dry dichloromethane. Argon gas is slowly introduced into the device. The solution was cooled to 5-10° C. and a solution of trifluoromethanesulfonic anhydride (20.5 mL, 34.39 g, 122 mmol, 1 eq) in 20 mL of dry dichloromethane was added dropwise over 20 minutes. The reaction was exothermic and maintained at a temperature of 5-15° C. The solution was then stirred at room temperature for two hours and then cooled again with ice-water. A solution of methyl-2-aminothiophene-3-carboxylate (21.08 g, 134 mmol, 1.1 eq.) in 100 ml of dry dichloromethane was added over a period of 15 minutes at 5-15° C. The reaction is exothermic, the mixture was refluxed for 24 hours after addition. Meanwhile, the introduction of argon is no longer necessary.

Then, 140 ml of saturated $Na_2CO_3$ solution was slowly added to the cooled solution to room temperature taking care of foaming. The organic layer was separated, washed twice with water (100 mL) and concentrated in vacuo. The residue was dissolved in isopropyl-acetate and extracted seven times with 70 ml of 10% citric acid solution. The organic phase was discarded for further processing. The combined aqueous phases were extracted with 60 ml of isopropyl-acetate and adjusted to pH 9 with saturated $Na_2CO_3$ solution, observing the foaming. The mixture was then extracted 3 times with 100 ml of isopropyl-acetate. The combined organic phases are dried over Na$_2$SO$_4$, filtered and concentrated in vacuo. The residue was purified by column chromatography on silica gel with a gradient of dichloromethane/isopropyl-acetate. Yield: 10.70 g.

After the extraction with citric acid, the separated organic phase was evaporated after drying and purified by the same chromatographic method. 6.84 g of pure product can be recovered, and the combined yield is 17.54 g (51 mmol, 41.7%) of a yellow oil. Rf=0.49 cyclohexane-ethyl acetate 1:1. ESI-MS (M+H$^+$)=345.

$^1$H-NMR (500 MHz DMSO-d$_6$ T=300K): δ 1.90 (m, 2H), 2.48 (m, 2H), 3.29 (m, 2H), 3.67 (s, 3H), 3.74 (s, 3H), 4.53 (s, 2H), 6.81 (d, J=5.9 Hz, 1H), 6.90 (d, J=8.6 Hz, 2H), 7.09 (d, J=5.9 Hz, 1H), 7.32 (d, J=8.6 Hz, 2H).

$^{13}$C DEPTq NMR (126 MHz DMSO-d$_6$): δ 19.0, 27.9, 46.3, 48.1, 50.8, 55.0, 113.8, 114.5, 115.1, 127.1, 128.9, 129.2, 158.5, 163.2, 163.7, 165.4.

12-[(4-methoxyphenyl)methyl]-4-thia-2,12-diazatricyclo[7.3.0.0$^{3,7}$]dodeca-1(9),2,5,7-tetraene-8-ol

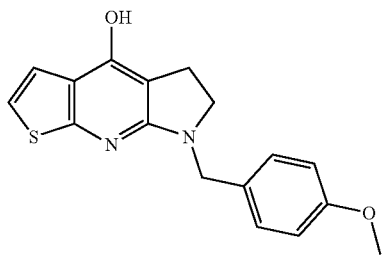 [SMILES: COc1ccc(CN2CCc3c2nc2sccc2c3O)cc1]

Methyl-2-{[(2E)-1-[(4-methoxyphenyl)methyl]pyrrolidin-2-ylidene]amino}thiophene carboxylate and 150 ml of toluene was added to a 250 mL round bottom flask. A water separator and a reflux condenser are placed on the flask and refluxed until no water is removed. After refluxing for 5 hours, the water content is measured and, if it is below 0.04%, is cooled and the toluene is evaporated in vacuo. The residue was then dissolved in 75 ml of dry tetrahydrofuran and transferred to a flask with a 3 neck, equipped with reflux condenser, dripping top and gas inlet. Potassium-tert-butylate (30 mL) in 20.1% tetrahydrofuran (5.35 g KOtBu, 47.7 mmol, 1.7 eq.) was then slowly added at room temperature. Yellow precipitate forms during the addition. The solution was then refluxed under argon until the starting material was consumed and the reaction was monitored by thin layer chromatography. After completion of the reaction, the contents of the flask were cooled to room temperature and 10 ml of acetic acid was added dropwise. The reaction mixture was then poured into a single-necked round-bottomed flask and the solvent was evaporated in vacuo. The residue was suspended in 50 ml of toluene and the solvent was again evaporated in vacuo. The residue was suspended in 50 ml of water and the pH was adjusted to 8 with 160 ml of saturated NaHCO$_3$ (foaming!). The suspension was stirred for 30 minutes and then filtered. The precipitate was washed three times with 100 ml of water and then with 50 ml of methyl-tert-butyl-ether and dried in vacuo. Yield: 7.19 g (23.0 mmol, 82%) of light brown powder. Rf=0.56 toluene:dioxane:acetic acid 10:3:1. ESI-MS (M+H$^+$)=313.

$^1$H-NMR (500 MHz DMSO-d$_6$T=300K): δ 2.90 (t, J=8.4 Hz, 2H), 3.35 (t, J=8.4 Hz, 2H), 3.72 (s, 3H), 4.45 (s, 2H), 6.88 (d, J=8.6 Hz, 2H), 7.05 (d, J=5.9 Hz, 1H), 7.22 (d, J=8.6 Hz, 2H), 7.26 (d, J=5.9 Hz, 1H), 10.36 (bs, 1H).

$^{13}$C DEPTq NMR (126 MHz DMSO-d$_6$): δ 22.4, 48.0, 48.8, 55.0, 102.3, 113.8, 116.4, 117.3, 118.9, 129.2, 129.7, 153.9, 158.3, 160.9, 163.7.

4-thia-2,12-diazatricyclo[7.3.0.0$^{3,7}$]dodeca-1 (9),2,5,7-tetraene-8-ol

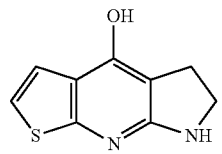 [SMILES: Oc1c2c(nc3sccc13)NCC2]

4.95 g (15.9 mmol, 1 eq) of 12-[(4-methoxyphenyl)methyl]-4-thia-2,12-diazatricyclo[7.3.0.0$^{3,7}$]dodeca-1(9),2,5,7-tetraen-8-ol was weighed into a round-bottomed flask. The solid was suspended in 15.5 ml (15.43 g of 143 mmol, 9 eq) anisole. A dripping top and a reflux condenser were placed on the flask. A CaCl$_2$) tube is placed on top of the cooler. The steam room was rinsed with argon and 10 mL (14.90 g, 130 mmol, 8.2 eq.) of trifluoroacetic acid was added over 5 min. Meanwhile, the solids dissolve. The solution was stirred at 70° C. for 72 hours and the reaction was monitored by thin layer chromatography. The flask was cooled with ice water after the starting material was consumed and 10 ml of concentrated hydrochloric acid was added at 0-5° C. The mixture was stirred cold for 10 minutes to give the hydrochloride salt of the product. It is then filtered, washed with cold acetonitrile and diethyl-ether. The hydrochloride salt was suspended in 20 ml of saturated NaHCO$_3$ solution, stirred for 30 minutes, and then the precipitate was filtered off. This was washed with water (20 mL) and methyl-tert-butyl-ether (10 mL). Yield: 1.61 g (8.4 mmol, 53%) of light brown powder. Rf=0.19 toluene:dioxane:acetic acid 10:3:1. ESI-MS (M+H$^+$)=193.

$^1$H-NMR (500 MHz DMSO-d$_6$T=300K): δ 2.94 (t, J=8.3 Hz, 2H), 3.49 (t, J=8.3 Hz, 2H), 6.32 (bs, 1H), 7.00 (d, J=5.9 Hz, 1H), 7.23 (d, J=5.9 Hz, 1H), 10.21 (bs, 1H).

$^{13}$C DEPTq NMR (126 MHz DMSO-d$_6$): δ 24.2, 43.9, 101.8, 116.1, 116.9, 118.8, 153.8, 160.6, 166.0.

9-hydroxy-4-thia-2,12-diazatricyclo[7.3.0.0$^{3,1}$]dodeca-1,3(7),5-trien-8-one

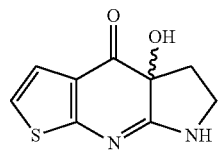 [SMILES: O=C1c2ccsc2N=C2NCCC12O]

An argon-filled balloon was placed in the septum. The vessel is then cooled with ice water. With a syringe, 2.6 ml of a 20.7% LiHMDS solution (437 mg LiHMDS, 2.83 mmol, 2 eq.) in tetrahydrofuran are added via the septum. The reaction mixture then turns brown and solids dissolve. The reaction was monitored by thin layer chromatography and stirred until the starting material was consumed at room temperature. Saturated NH$_4$Cl (15 mL) was then added and the mixture was extracted with 2-methyl-tetrahydrofuran (3×15 mL). The organic phases are combined, dried over Na$_2$SO$_4$, filtered and evaporated. The crude product was purified by column chromatography. Yield: 74 mg (0.36 mmol, 25%) of a red solid. It was then purified by preparative HPLC. Rf=0.32 Toluene:dioxane:acetic acid 10:3:1. Rf=0.38 ethyl acetate. ESI-MS (M+H$^+$)=209.

4A.9 Preparation of 8a-hydroxy-6-phenyl-6H,7H, 8H,8aH,9H-pyrrolo[2,3-b]1,5-naphthyridin-9-one Methyl-3-{[(2E)-1-phenylpyrrolidin-2-ylidene]amino}pyridine-2-carboxylate

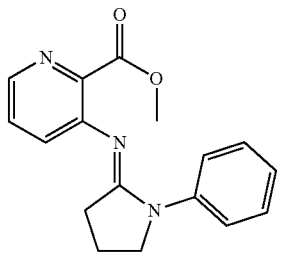 [SMILES: COC(=O)c1ncccc1/N=C1\CCCN1c1ccccc1]

In an inert three-necked flask under argon, 5.00 g (31.02 mmol, 1 eq.) of 1-phenylpyrrolidin-2-one was dissolved in 35 ml of dry dichloromethane. A dripping top, a reflux condenser and a CaCl$_2$) tube were placed on the flask. A solution of trifluoromethanesulfonic anhydride (5.2 mL, 8.75 g, 31.02 mmol, 1 eq) in 10 mL of dry dichloromethane was added dropwise over 2 min. The temperature rises until the solution boils slightly. Allow to cool to room temperature and stir for three hours. Then, a suspension of 5.19 g (34.12 mmol, 1.1 eq.) of 3-aminopyridine-2-carboxylic acid-methyl ester in 35 ml of dry dichloromethane is carefully added through a large diameter funnel. The apparatus was re-inerted with argon and the reaction mixture was stirred at reflux temperature for 24 hours. To the cooled reaction mixture was slowly added 60 mL of saturated Na$_2$CO$_3$ solution while stirring. After separation of the phases, the aqueous phase was extracted with dichloromethane (2×40 mL). The combined organic layers were dried over Na$_2$SO$_4$, filtered and concentrated. The residue was used without further purification. Yield: 10.12 g of black oil, solidified on standing.

6-phenyl-6H,7H,8H-pyrrolo[2,3-b]1,5-naphthyridin-9-ol

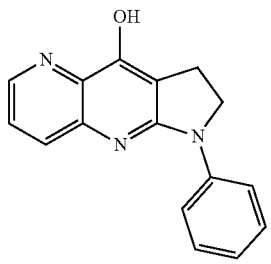 [SMILES: Oc1c2c(nc3cccnc13)N(c1ccccc1)CC2]

The crude methyl 3-{[(2E)-1-phenylpyrrolidin-2-ylidene]amino}pyridine-2-carboxylate obtained in the previous step was dissolved in 80 ml of dry tetrahydrofuran and poured into a three-necked round bottom flask. The flask was fitted with a dripping top and a reflux condenser, the latter with a CaCl$_2$) tube. The apparatus was made inert with argon and 42.5 ml of 20.1 m/m % potassium-tert-butylate solution (7.68 g KOtBu, 68.53 mmol, 2 eq.) was added dropwise over 5 minutes. To calculate the base, the previous step is considered to be 100%. The reaction mixture precipitated and the precipitate dissolved during warming. After 24 hours reflux, the mixture was cooled to room temperature and 5 ml of acetic acid was added. The reaction mixture was diluted with water (300 mL) and the precipitate was filtered off, washed with water and dried in vacuo at 50° C. The crude product was used without further purification. Yield: 4.11 g brown powder. ESI-MS (M+H$^+$)=264.

8a-hydroxy-6-phenyl-6H,7H,8H,8aH,9H-pyrrolo[2,3-b]1,5-naphthyridin-9-one (190)

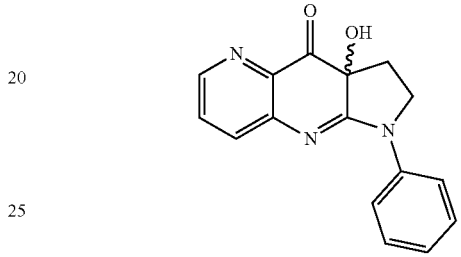

1.06 g (4.00 mmol, 1 eq.) of crude 6-phenyl-6H,7H,8H-pyrrolo[2,3-b]1,5-naphthyridin-9-ol and 1.57 g (6,00 mmol, 1.5 eq.) 2-(benzenesulfonyl)-3-phenyl-oxaziridine is weighed into a 100 ml round-bottom flask. Dry tetrahydrofuran (50 ml) was added, it was made inert with argon and sealed with septum. An argon filled balloon was placed in the septum. The vessel is then cooled with ice water. 7.5 ml of a 20.7% LiHMDS solution (1.34 g LiHMDS, 8.00 mmol, 2 eq.) in tetrahydrofuran is added via syringe. Stir for 5 days at room temperature. 40 ml of methyl-tert-butyl-ether and 40 ml of 2M hydrochloric acid were then added. A brown precipitate is formed which was removed by filtration. The filtrate was separated and the organic phase was extracted twice with 20 ml of 2 M hydrochloric acid and the combined aqueous phases were concentrated in vacuo to leave the organic solvents. The aqueous phase was neutralized with 10% Na$_2$CO$_3$ (foaming!). Meanwhile, a dark orange precipitate forms. This was filtered, washed with water and dried under vacuum at 40° C. Yield: 185 mg of crude product, which was purified by preparative HPLC. ESI-MS (M+H$^+$)=280.

4A.10 Preparation of 3α-hydroxy-1-phenyl-1H,2H, 3H,3aH,4H-pyrrolo[2,3-b]1,8-naphthyridin-4-one Methyl-2-{[(2E)-1-phenylpyrrolidin-2-ylidene]amino}pyridine-3-carboxylate

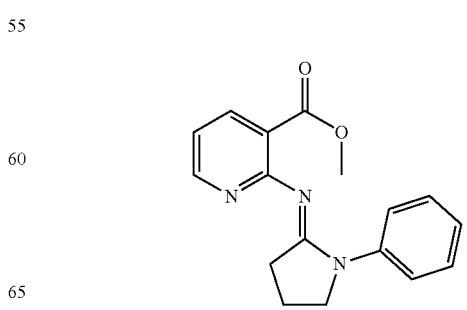

In an inert three-necked flask under argon, 5.00 g (31.02 mmol, 1 eq.) of 1-phenylpyrrolidin one was dissolved in 35 ml of dry dichloromethane. A dripping top, a reflux condenser and a CaCl₂ tube were placed on the flask. A solution of trifluoromethanesulfonic anhydride (5.2 mL, 8.75 g, 31.02 mmol, 1 eq) in 10 mL of dry dichloromethane was added dropwise over 2 min. The temperature rises until the solution boils slightly. Allow then to cool to room temperature and stir for three hours. A solution of 2-aminopyridine-3-carboxylic acid-methyl-ester (5.19 g, 34.12 mmol, 1.1 eq.) in dry dichloromethane (35 mL) was then added and the reaction mixture was stirred at reflux for 48 h. To the cooled reaction mixture 60 mL of saturated Na₂CO₃ solution was slowly added while stirring. After separation of the phases, the organic phase was extracted with 40 ml of dichloromethane. The combined organic layers were dried over Na₂SO₄, filtered and concentrated. The residue was used without further purification. Yield: 3.31 g brown oil, partially solidified on standing. ESI-MS (M+H⁺)=296.

1-phenyl-1H,2H,3H-pyrrolo[2,3-b]-1,8-naphthyridin-4-ol

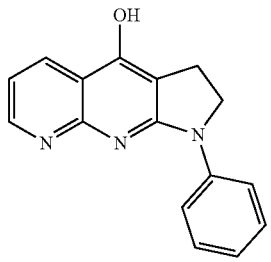 [SMILES: Oc1c2c(nc3ncccc13)N(c1ccccc1)CC2]

The crude methyl-2-{[(2E)-1-phenylpyrrolidin-2-ylidene]amino}pyridine-3-carboxylate obtained in the previous step was dissolved in dry tetrahydrofuran (40 ml) and poured into a three-necked round-bottomed flask. The flask was fitted with a dripping top and a reflux condenser, the latter with a CaCl₂ tube. The apparatus was made inert with argon and 13.9 ml of 20.1 m/m % potassium-tert-butylate solution (2.51 g KOtBu, 22.38 mmol, 2 eq.) was added dropwise over 5 minutes. To calculate the base, the previous step was considered to be 100%. The brown precipitate is coming out. After refluxing for 3 hours, the mixture was cooled to room temperature and 5 ml of 2M hydrochloric acid was added. The pH was then adjusted to 8 with saturated NaHCO₃. A yellow precipitate is formed which is filtered off, washed with water and then dried under vacuum. The crude product was used without further purification. Yield: 1.35 g yellow powder. ESI-MS (M+H⁺)=264.

¹H-NMR δ (500 MHz DMSO-d₆ T=300K): 3.25 (t, J=8.0 Hz, 2H), 4.27 (t, J=8.0 Hz, 2H), 7.21 (t, J=7.5 Hz, 1H), 7.45 (dd, J₁=7.5, J₂=8.5 Hz, 2H), 7.56 (dd, J₁=5.7 Hz, J₂=7.9 Hz, 1H), 7.95 (d, J=8.5 Hz, 2H), 8.68 (dd, J₁=1.5 Hz, J₂=5.6 Hz, 1H), 8.81 (dd, J₁=1.5 Hz, J₂=7.9 Hz, 1H), 10.91 (s, 1H).

¹³C DEPTq NMR δ (126 MHz DMSO-d₆ T=300K): 21.8 50.0, 110.4, 117.0, 117.3, 120.1, 124.3, 128.8, 138.6, 139.7, 141.8, 150.6, 153.6, 163.7.

3α-hydroxy-1-phenyl-1H,2H,3H,3aH,4H-pyrrolo[2,3-b]1,8-naphthyridin-4-one (189)

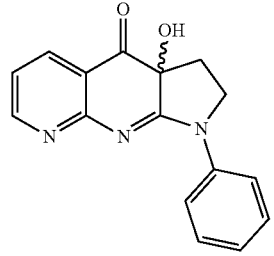 [SMILES: O=C1c2cccnc2N=C2N(c3ccccc3)CCC12O]

0.79 g (3.00 mmol, 1 eq.) of crude 1-phenyl-1H,2H,3H-pyrrolo[2,3-b]1,8-naphthyridin-4-ol and 1.18 g (4.50 mmol, 1.5 eq.) 2-(benzenesulfonyl)-3-phenyloxaziridine was weighed into a 50 mL round bottom flask. Dry tetrahydrofuran (30 ml) was added, it was made inert with argon and sealed with septum. An argon filled balloon was placed in the septum. The vessel is then cooled with ice water. 5.5 ml of a 20.7% LiHMDS solution (1.00 g LiHMDS, 6.00 mmol, 2 eq) in tetrahydrofuran was added via syringe. Stir for 8 days at room temperature. 40 ml of methyl-tert-butyl-ether and 40 ml of 2M hydrochloric acid were then added. The filtrate was separated and the organic phase was extracted twice with 20 ml of 2 M hydrochloric acid. The combined aqueous phases were adjusted to pH=8 with saturated NaHCO₃ solution (foaming!). Meanwhile, a yellow precipitate forms. This was filtered, washed with water and dried under vacuum at 40° C. Yield: 414 mg (1.48 mmol, 49%). ESI-MS (M+H⁺)=280.

¹H-NMR δ (500 MHz DMSO-d₆ T=300K): 2.27 (dd, J₁=5.7 Hz, J₂=13.2 Hz, 1H), 2.37 (ddd, J₁=9.0 Hz, J₂=9.3 Hz, J₁=13.2 Hz, 1H), 4.02 (dd, J₁=9.1 Hz, J₂=9.3 Hz, 1H), 4.17 (ddd, J₁=6.0 Hz, J₂=9.0 Hz, J₃=9.4 Hz, 1H), 7.04 (s, 1H), 7.10 (dd, J₁=5.0 Hz, J₂=7.4 Hz, 1H), 7.22 (t, J=7.3 Hz, 1H), 7.46 (t, J=7.7 Hz, 2H), 8.06 (dd, J₁=1.6 Hz, J₂=7.1 Hz, 1H), 8.08 (d, J=8.4 Hz, 2H), 8.54 (dd, J₁=1.6 Hz, J₂=5.0 Hz, 1H).

¹³C-NMR DEPTq δ (126 MHz DMSO-d₆ T=300K): 27.9, 48.1, 73.1, 116.4, 118.5, 120.6, 124.5, 128.6, 135.0, 139.9, 154.7, 162.7, 168.0, 193.7.

4A.11 Preparation of 3α-hydroxy-1H,2H,3H,3aH, 4H-pyrrolo[2,3-b]1,7-naphthyridin-4-one Ethyl-3-{[(2E)-1-[(4-methoxyphenyl)methyl]pyrrolidin-2-ylidene]amino}pyridine-4-carboxylate

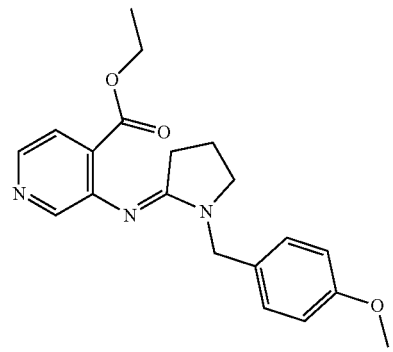 [SMILES: CCOC(=O)c1ccncc1/N=C1\CCCN1Cc1ccc(OC)cc1]

A dry 4-neck 500-ml round-bottomed flask was equipped with reflux cooler, thermometer, dripping top and gas inlet. 28.53 g (139 mmol, 1.05 eq.) of 1-[(4-methoxyphenyl)methyl]pyrrolidin-2-one and 50 ml of dry chloroform are weighed in the flask. Slowly argon was introduced and phosphorus oxychloride (13 mL, 21.31 g, 139 mmol, 1.05 eq.) was added over 5 min from the dripping top. The reaction is slightly exothermic. Allow then to cool to room temperature and stir for three hours. Then, a solution of ethyl 3-amino-isonicotinate (22.00 g, 132 mmol, 1 eq.) in 50 mL of dry chloroform was added over 5 minutes. If the solution boils, the addition is slowed down to achieve slight boiling. After addition, the reaction mixture was further refluxed for 48 hours under an argon atmosphere. The reaction was monitored by thin layer chromatography. After 48 hours, the reaction mixture was cooled to room temperature and 220 ml of saturated $Na_2CO_3$ 3 solution (foaming!) was added slowly with stirring. Then, another 150 ml of water was added and the phases were separated. The aqueous phase was washed twice with 100 ml of chloroform and the combined organic phases were extracted with water (100 ml) and dried over $Na_2SO_4$. After filtration, it is concentrated and dissolved in 50 ml of ethyl-acetate. On a glass filter, 200 g of silica gel was wetted with ethyl acetate and through this a solution of the product was filtered. Wash with ethyl acetate until the product is detected in the filtrate by thin-layer chromatography. The combined solutions were then concentrated and the residue was dissolved in isopropyl acetate and dried over $Na_2SO_4$. After filtration, it is concentrated in vacuo. Yield: 40.99 g (115 mmol, 88%). ESI-MS (M+H+)=354. Rf=0.55 running the same plate three times in ethyl acetate.

$^1$H-NMR δ (500 MHz DMSO-$d_6$ T=300K): 1.20 (t, J=7.0 Hz, 3H), 1.87 (m, 2H), 2.30 (t, J=6.8 Hz, 2H), 3.26 (t, J=6.8 Hz, 2H), 3.74 (s, 3H), 4.21 (q, J=7.0 Hz, 2H), 4.50 (s, 2H), 6.90 (m, $J_1$=8.5 Hz, 2H), 7.28 (m, $J_1$=8.5 Hz, 2H), 7.45 (d, J=5.0 Hz, 1H), 8.16 (s, br, 1H), 8.21 (d, J=5.0 Hz, 1H).

$^{13}$C-NMR δ (126 MHz DMSO-$d_6$ T=300K): 13.9, 19.1, 27.7, 46.2, 48.0, 55.0, 60.8, 113.7, 122.0, 129.2, 129.3, 130.1, 141.9, 145.9, 147.0, 157.5, 158.4, 162.1, 166.1.

1-[(4-methoxyphenyl)methyl]-1H, 2H,3H-pyrrolo[2,3-b]1,7-naphthyridin-4-ol

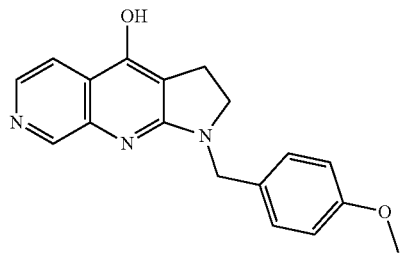 [SMILES: COc1ccc(CN2CCc3c2nc2cnccc2c3O)cc1]

39.41 g (112 mmol, 1 eq.) of ethyl-3-{[(2E)-1-[(4-methoxyphenyl)methyl]pyrrolidin-2-ylidene]amino}pyridine-4-carboxylate was added to a 500 mL round bottom flask and dissolved in 300 ml of toluene. A water separator was placed on the flask, and a reflux condenser was fitted on the water separator, and it was boiled until a water separation is observed. After two hours, the water contert of the solution reaches 0.01 m/m %. The mixture was then cooled to room temperature and the toluene was evaporated in vacuo. The residue was dissolved in 300 ml of dry tetrahydrofuran and poured into a three-necked round-bottomed flask. A reflux condenser, a drip tray and a thermometer were placed on the flask. In an argon atmosphere, 105 ml of a 20.1 m/m % solution of potassium tert-butylate in tetrahydrofuran (18.76 g KOtBu, 167 mmol, 1.5 eq.) was added dropwise over 10 minutes with stirring. The solution warmed to 35° C. during this time and a light brown precipitate formed. The reaction was monitored by thin layer chromatography and refluxed until the starting material was consumed (consumption of the starting material was described in the previous intermediate in the eluent). After cooling to room temperature, 20 ml of acetic acid was added. The reaction mixture was poured into a single-necked round-bottomed flask and the solvents were evaporated in vacuo. The residue was suspended in 500 ml of water and adjusted to pH=9 with saturated $Na_2CO_3$ solution (foaming!). The solid was filtered off, washed with water (2×250 mL) and dried in vacuo. Yield: 33.01 g (107 mmol, 96%) of light brown powder. ESI-MS (M+H+)=308. Rf=0.78 dichloromethane:methanol 10:1, neutral E2 $Al_2O_3$.

$^1$H-NMR δ (500 MHz DMSO-$d_6$ T=300K): 3.01 (t, br, J=8.0 Hz, 2H), 3.45 (t, J=8.0 Hz, 2H), 3.72 (s, 3H), 4.59 (s, 2H), 6.88 (d, J=8.6 Hz, 2H), 7.24 (d, J=8.6 Hz, 2H), 7.70 (d, J=5.2 Hz, 1H), 8.18 (d, J=5.2 Hz, 1H), 8.75 (s, 1H), 11.3-10.1 (br, 1H).

$^{13}$C-HMBC NMR δ (126 MHz DMSO-$d_6$ T=300K): 22.7 47.1, 47.6, 55.0, 108.0, 113.9, 114.7, 123.7, 129.2, 139.3, 143.4, 147.0, 153.4, 158.4, 162.7.

1H,2H,3H-pyrrolo[2,3-b] 1,7-naphthyridin-4-ol

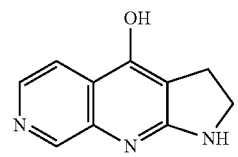 [SMILES: Oc1c2c(nc3cnccc13)NCC2]

26.00 g (85 mmol, 1 eq.) of 1-[(4-methoxyphenyl)methyl]-1H,2H,3H-pyrrolo[2,3-b]1,7-naphthyridin-4-ol was weighed in a 3-neck 250 ml round bottom flask. A dripping top and a reflux condenser were fitted to the flask, and a $CaCl_2$) tube was equipped thereon. The steam room was flushed with argon. The starting material was suspended in anisole (83 mL, 82.33 g, 761 mmol, 9 eq.), and 52 mL (77.16 g, 677 mmol, 8 eq.) of trifluoroacetic acid was added slowly while stirring. Meanwhile, the solids dissolve. The reaction mixture was stirred at 70° C. until the starting material was consumed, followed by thin layer chromatography. The reaction takes place in about 10 days. The solution was cooled to room temperature and ethyl-acetate (100 mL) and hexane (40 mL) were added and the mixture was extracted with 80 mL of 2 M hydrochloric acid. The precipitate formed is filtered off, dissolved in water and added to the hydrochloric acid extract. The organic phase was extracted four more times with 40 mL of 2 M hydrochloric acid. The combined aqueous phases were extracted with 1:1 hexane-ethyl-acetate (80 mL) and separated. The pH was adjusted to 8 with 10% NaOH, the precipitate was filtered off, washed with cold water (100 mL) and dried under vacuum. Yield: 13.97 g (75 mmol, 88%) of yellow powder. Rf=0.17 dichloromethane:methanol 10:1, neutral E-type $Al_2O_3$.

¹H NMR δ (500 MHz DMSO-d₆ T=300K): 2.96 (t, br J=8.4 Hz, 2H), 3.57 (t, J=8.4 Hz, 2H), 7.06 (s, br, 1H), 7.74 (d, J=4.9 Hz, 1H), 8.22 (d, J=4.9 Hz, 1H), 8.67 (s, br, 1H), 12.5-10.0 (br, 1H).

¹³C (DEPTq, HMBC) NMR δ (126 MHz DMSO-d₆ T=300K): 24.3, 43.6, 105.1, 115.9, 126.1, 139.1, 140.4, 143.8, 160.2, 161.4.

3α-hydroxy-1H,2H,3H,3aH,4H-pyrrolo[2,3-b]1,7-naphthyridin-4-one (255)

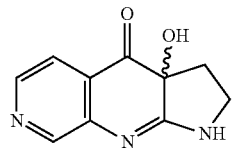 [SMILES: O=C1c2ccncc2N=C2NCCC12O]

2.00 g (10.7 mmol, 1 eq.) of 1H,2H,3H-pyrrolo[2,3-b]1,7-naphthyridin-4-ol and 5.18 g (19.8 mmol, 1, 9 eq. of 2-(benzenesulfonyl)-3-phenyloxaziridine was weighed into a three-necked 100 ml round-bottomed flask and 20 ml of dry tetrahydrofuran was added. Then the flask was made inert with argon, and a balloon filled with argon, a thermometer and a plug were placed on the flask. The mixture was cooled in ice water to 0-5° C., and 19.3 ml of 20.7 m % LiHMDS solution (4.87 g LiHMDS, 29.1 mmol, 2 eq.) in tetahydrofurane was added via syringe. The reaction mixture is then stirred at room temperature until the starting material is consumed. The reaction was monitored by thin-layer chromatography (chloroform-methanol in 10:1, run twice). Water (2 mL) was added after 41 h and the mixture was stirred for 10 min, then Celite (6 g) was added and the residue was purified by column chromatography. (dichloromethane, 0-25% MeOH) The appropriate fractions were evaporated and the residue was taken up in 10 mL methanol. The precipitate was filtered off (660 mg). The filtrate was evaporated and the operation was repeated with the residue in 5 ml of methanol. The solids were combined. Yield: 807 mg (3.97 mmol, 37%). ESI-MS (M+H⁺)=204.

¹H NMR (DMSO-d₆, 500 MHz): δ 2.11 (dd, J=5.4, 13.5 Hz, 1H), 2.21 (m, 1H), 3.51 (m, 1H), 3.58 (m, 1H), 6.75 (s, 1H), 7.45 (d, J=4.7 Hz, 1H), 8.14 (d, J=4.7 Hz, 1H), 8.37 (s, 1H), 9.22 (bs, 1H).

¹³C DEPTq NMR (DMSO-d₆, 500 MHz): δ 30.8, 44.5, 118.5, 124.7, 141.4, 145.1, 194.0.

Example 4: Demonstration of the Effectiveness of the Compounds of the Invention

To demonstrate effectiveness, the following methodology was used: actomyosin steady state ATPase measurement on the following myosin 2 isoforms:

a) recombinant human non-muscle myosin 2 on all three isoforms (NM2A, NM2B, NM2C),
b) isolated porcine cardiac ventricular myocardium (cardiac),
c) isolated rabbit skeletal muscle myosin (skeletal),
d) isolated chamois smooth muscle myosin
e) recombinant Dictyostelium miozin (Dictyostelium).

We determined (i) the maximum value of inhibition of ATPase activity for all myosin isoforms and for all compounds where the degree of inhibition was at least 20% at 50 micromolar concentration; (ii) the concentration required for semi-maximal inhibition. The results are summarized in the tables below.

The following table gives the name, structure, and reference number of compounds in the following efficacy examples

TABLE 3A

| No. of compound | Structural formula of the compound | Chemical name of the compound |
| --- | --- | --- |
| 174 | | 3a-Hydroxy-1-phenyl-1H,2H,3H,3aH,4H-pyrrolo[2,3-b]1,7-naphthyridine-4-one (Compound 1) |
| 180 | | 9-Hydroxy-12-phenyl-4-thia-2,12-diazatricyclo[7.3.0.0³,⁷]dodeca-1,3(7),5-trien-8-one (Compound 2) |

TABLE 3A-continued

| No. of compound | Structural formula of the compound | Chemical name of the compound |
| --- | --- | --- |
| 183 | | 7-Hydroxy-4-phenyl-10-thia-2,4-diazatricyclo[7.3.0.0$^{3,7}$]dodeca-1(9),2,11-trien-8-one<br>(Compound 3) |
| 188 | | 9-Hydroxy-12-[4-(morpholin-4-yl)phenyl]-4-thia-2,12-diazatricyclo[7.3.0.0$^{3,7}$]dodeca-1,3(7),5-trien-8-one |
| 189 | | 3a-Hydroxy-1-phenyl-1H,2H,3H,3aH,4H-pyrrolo[2,3-b]1,8-naphthyridine-4-one |
| 190 | | 8a-Hydroxy-6-phenyl-6H,7H,8H,8aH,9H-pyrrolo[2,3-b]1,5-naphthyridine-9-one |
| 198 | | 9-Hydroxy-5-methyl-12-phenyl-4-thia-2,12-diazatricyclo[7.3.0.0$^{3,7}$]dodeca-1,3(7),5-trien-8-one |

TABLE 3A-continued

| No. of compound | Structural formula of the compound | Chemical name of the compound |
|---|---|---|
| 206 | | 12-phenyl-9-Hydroxy-6-methyl-4-thia-2,5,12-triazatricyclo[7.3.0.0$^{3,7}$]dodeca-1,3(7),5-trien-8-one |
| 207 | | (9S)-9-Hydroxy-4-thia-2,12-diazatricyclo[7.3.0.0$^{3,7}$]dodeca-1,3(7),5-trien-8-one |
| 208 | | (9S)-9-Hydroxy-5-methyl-12-(thiophen-2-yl)-4-thia-2,12-diazatricyclo[7.3.0.0$^{3,7}$]dodeca-1,3(7),5-trien-8-one |
| 210 | | (9S)-12-(4-aminophenyl)-9-hydroxy-4-thia-2,12-diazatricyclo[7.3.0.0$^{3,7}$]dodeca-1,3(7),5-trien-8-one |
| 211 | | (9S)-9-hydroxy-12-(4-methoxyphenyl)-4-thia-2,12-diazatricyclo[7.3.0.0$^{3,7}$]dodeca-1,3(7),5-trien-8-one |

TABLE 3A-continued

| No. of compound | Structural formula of the compound | Chemical name of the compound |
|---|---|---|
| 212 | 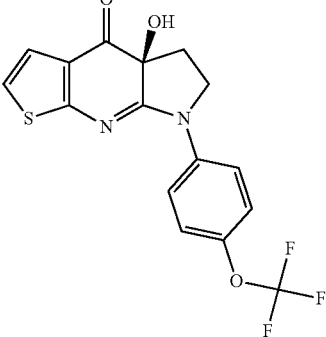 | (9S)-9-hydroxy-12-[4-(trifluoromethoxy)phenyl]-4-thia-2,12-diazatricyclo[7.3.0.0$^{3,7}$]dodeca-1,3(7),5-trien-8-one |
| 213 | 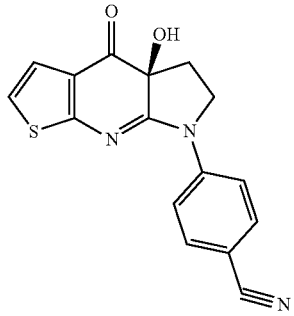 [SMILES: N#Cc1ccc(N2CC[C@@]3(O)C(=O)c4ccsc4N=C23)cc1] | (9S)-4-{9-Hydroxy-8-oxo-4-thia-2,12-diazatricyclo[7.3.0.0$^{3,7}$]dodeca-1,3(7),5-trien-12-yl}benzonitrile |
| 214 | 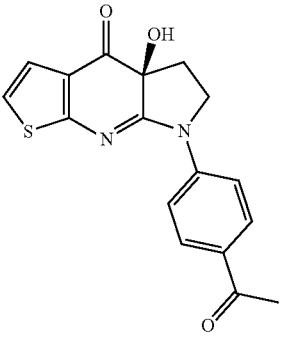 [SMILES: CC(=O)c1ccc(N2CC[C@@]3(O)C(=O)c4ccsc4N=C23)cc1] | (9S)-12-(4-acetylphenyl)-9-hydroxy-4-thia-2,12-diazatricyclo[7.3.0.0$^{3,7}$]dodeca-1,3(7),5-trien-8-one |
| 215 | 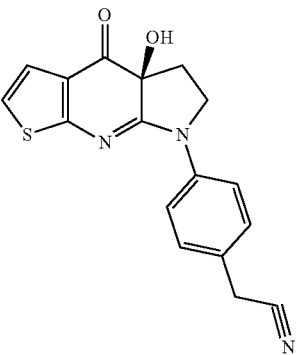 [SMILES: N#CCc1ccc(N2CC[C@@]3(O)C(=O)c4ccsc4N=C23)cc1] | (9S)-2-(4-{9-Hydroxy-8-oxo-4-thia-2,12-diazatricyclo[7.3.0.0$^{3,7}$]dodeca-1,3(7),5-trien-12-yl}phenyl)acetonitrile |

TABLE 3A-continued

| No. of compound | Structural formula of the compound | Chemical name of the compound |
| --- | --- | --- |
| 216 | | (9S)-9-Hydroxy-12-[4-(hydroxymethyl)phenyl]-4-thia-2,12-diazatricyclo[7.3.0.0$^{3,7}$]dodeca-1,3(7),5-trien-8-one |
| 218 | | (9S)-9-Hydroxy-12-(thiophen-2-yl)-4-thia-2,12-diazatricyclo[7.3.0.0$^{3,7}$]dodeca-1,3(7),5-trien-8-one |
| 219 | | (9S)-9-Hydroxy-12-(6-methoxypiridin-3-yl)-4-thia-2,12-diazatricyclo[7.3.0.0$^{3,7}$]dodeca-1,3(7),5-trien-8-one |
| 220 | | 9-Hydroxy-5-methyl-12-[4-(morpholin-4-yl)phenyl]-4-thia-2,12-diazatricyclo[7.3.0.0$^{3,7}$]dodeca-1,3(7),5-trien-8-one |
| 221 | | 12-(4-Aminophenyl)-9-hydroxy-5-methyl-4-thia-2,12-diazatricyclo[7.3.0.0$^{3,7}$]dodeca-1,3(7),5-trien-8-one |

TABLE 3A-continued

| No. of compound | Structural formula of the compound | Chemical name of the compound |
| --- | --- | --- |
| 222 | | 9-Hydroxy-12-(4-methoxyphenyl)-5-methyl-4-thia-2,12-diazatricyclo[7.3.0.0$^{3,7}$]dodeca-1,3(7),5-trien-8-one |
| 223 | | 9-Hydroxy-5-methyl-12-[4-(trifluoromethoxy)phenyl]-4-thia-2,12-diazatricyclo[7.3.0.0$^{3,7}$]dodeca-1,3(7),5-trien-8-one |
| 224 | | 4-{9-Hydroxy-5-methyl-8-oxo-4-thia-2,12-diazatricyclo[7.3.0.0$^{3,7}$]dodeca-1,3(7),5-trien-12-yl}benzonitrile |
| 225 | | 12-(4-Acetylphenyl)-9-hydroxy-5-methyl-4-thia-2,12-diazatricyclo[7.3.0.0$^{3,7}$]dodeca-1,3(7),5-trien-8-one |

TABLE 3A-continued

| No. of compound | Structural formula of the compound | Chemical name of the compound |
|---|---|---|
| 226 | | 2-(4-{9-Hydroxy-5-methyl-8-oxo-4-thia-2,12-diazatricyclo[7.3.0.0³,⁷]dodeca-1,3(7),5-trien-12-yl}phenyl)acetonitrile |
| 227 | | 9-Hydroxy-12-[4-(hydroxymethyl)phenyl]-5-methyl-4-thia-2,12-diazatricyclo[7.3.0.0³,⁷]dodeca-1,3(7),5-trien-8-one |
| 229 | | 9-Hydroxy-5-methyl-12-(thiophen-2-yl)-4-thia-2,12-diazatricyclo[7.3.0.0³,⁷]dodeca-1,3(7),5-trien-8-one |
| 230 | | 9-Hydroxy-12-(6-methoxypyridin-3-yl)-5-methyl-4-thia-2,12-diazatricyclo[7.3.0.0³,⁷]dodeca-1,3(7),5-trien-8-one |
| 231 | | 9-Hydroxy-5-methyl-4-thia-2,12-diazatricyclo[7.3.0.0³,⁷]dodeca-1,3(7),5-trien-8-one |

TABLE 3A-continued

| No. of compound | Structural formula of the compound | Chemical name of the compound |
|---|---|---|
| 233 | | (9S)-9-Hydroxy-12-(4-methylphenyl)-4-thia-2,12-diazatricyclo[7.3.0.0$^{3,7}$]dodeca-1,3(7),5-trien-8-one |
| 235 | | 12-[4-(Methyl)phenyl]-9-hydroxy-5-methyl-4-thia-2,12-diazatricyclo[7.3.0.0$^{3,7}$]dodeca-1,3(7),5-trien-8-one |
| 238 | | 3a-Hydroxy-1-[4-(trifluoromethoxy)phenyl]-1H,2H,3H,3aH,4H-pyrrolo[2,3-b]1,7-naphthyridine-4-one |
| 240 | | 1-(4-Acetylphenyl)-3a-hydroxy-1H,2H,3H,3aH,4H-pyrrolo[2,3-b]1,7-naphthyridine-4-one |

TABLE 3A-continued

| No. of compound | Structural formula of the compound | Chemical name of the compound |
| --- | --- | --- |
| 247 | 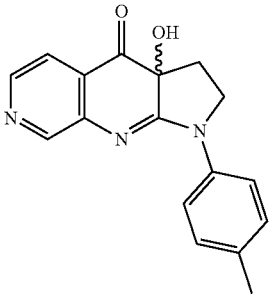 [SMILES: Cc1ccc(N2CCC3(O)C(=O)c4ccncc4N=C23)cc1] | 1-[4-(Methyl)phenyl]-3a-hydroxy-1H,2H,3H,3aH,4H-pyrrolo[2,3-b]1,7-naphthyridine-4-one |
| 248 | 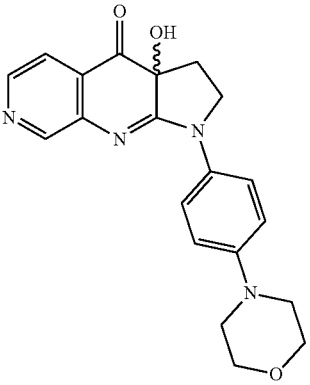 [SMILES: O=C1c2ccncc2N=C2N(c3ccc(N4CCOCC4)cc3)CCC12O] | 3a-Hydroxy-1-[4-(morpholin-4-yl)phenyl]-1H,2H,3H,3aH,4H-pyrrolo[2,3-b]1,7-naphthyridine-4-one |
| 249 | 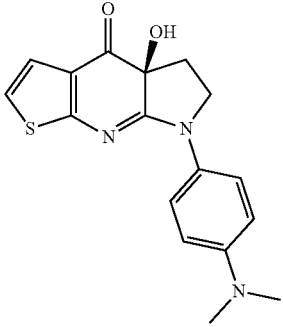 [SMILES: CN(C)c1ccc(N2CC[C@@]3(O)C(=O)c4ccsc4N=C23)cc1] | (9S)-12-[4-(dimethylamino)phenyl]-9-hydroxy-4-thia-2,12-diazatricyclo[7.3.0.0$^{3,7}$]dodeca-1,3(7),5-trien-8-one |
| 250 | 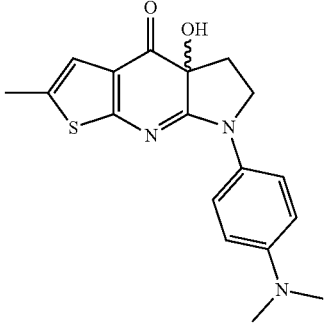 | 12-[4-(Dimethylamino)phenyl]-9-hydroxy-5-methyl-4-thia-2,12-diazatricyclo[7.3.0.0$^{3,7}$]dodeca-1,3(7),5-trien-8-one |

TABLE 3A-continued

| No. of compound | Structural formula of the compound | Chemical name of the compound |
|---|---|---|
| 251 | | 1-[4-(Dimethylamino)phenyl]-3a-hydroxy-1H,2H,3H,3aH,4H-pyrrolo[2,3-b]1,7-naphthyridine-4-one |
| 255 | | 3a-Hydroxy-1H,2H,3H,3aH,4H-pyrrolo[2,3-b]1,7-naphthyridine-4-one |

TABLE 3

Data for % inhibition of some compounds of the invention

| Number of compound | % inhibition at 5 µM (or 10 µM if racemate) | | | | | |
|---|---|---|---|---|---|---|
| | Dicty | NM2A | NM2B | NM2C | cardiac | Skeletal | Smooth |
| 174 | 7 | 12 | 2 | 7 | 2 | 25 | 1 |
| 180 | 22 | 15 | 14 | 20 | 42 | 87 | 16 |
| 183 | 26 | 4 | 16 | 6 | 33 | 80 | 17 |
| 188 | 5 | 0 | 8 | 8 | 0 | 50 | 0 |
| 189 | 0 | 4 | 0 | 11 | 11 | 37 | 8 |
| 198 | 51 | 26 | 24 | 51 | 64 | 90 | 44 |
| 206 | | 9 | | | 16 | 26 | 9 |
| 207 | 0 | | | | 4 | 7 | 7 |
| 208 | 55 | 37 | | 54 | | 87 | 26 |
| 210 | 3 | 0 | | 18 | 36 | 44 | 9 |
| 211 | 33 | 17 | | 46 | 67 | 93 | 34 |
| 212 | 26 | | | 19 | 43 | 94 | 24 |
| 213 | 50 | 13 | | 22 | 61 | 89 | 16 |
| 214 | 8 | 25 | | 21 | 30 | 80 | 6 |
| 215 | 23 | | | 16 | 42 | 80 | 31 |
| 216 | 20 | | | 13 | 58 | 74 | 17 |
| 218 | 4 | | | 2 | 49 | 50 | 10 |
| 219 | 6 | | | 8 | 44 | 69 | 15 |
| 220 | 0 | 16 | | 19 | 17 | 86 | 34 |
| 221 | 27 | | | 32 | 65 | 65 | 43 |
| 222 | 49 | | | 77 | 82 | 92 | 83 |
| 223 | 21 | | | 52 | 68 | 95 | 79 |
| 224 | 64 | | | 72 | 72 | 94 | 72 |
| 225 | 64 | | | 47 | 68 | 93 | 68 |
| 226 | 43 | | | 69 | 72 | 91 | 72 |
| 227 | 47 | | | 52 | 77 | 82 | 54 |
| 229 | 74 | | | 78 | 54 | 87 | 54 |
| 230 | 36 | | | 61 | 68 | 85 | 56 |
| 231 | 4 | | | | 6 | 5 | 7 |
| 233 | 21 | | | 48 | 74 | 92 | 29 |
| 235 | 44 | | | | 72 | 98 | 82 |
| 238 | 24 | | | 27 | 2 | 80 | 13 |
| 240 | 24 | | | | 13 | 49 | 18 |
| 247 | 4 | | | | 9 | 74 | 3 |
| 248 | 0 | | | | 4 | 21 | 1 |
| 249 | 15 | | | | 11 | 80 | 19 |
| 250 | 15 | | | | 26 | 93 | 81 |
| 251 | 1 | | | | 6 | 47 | 0 |
| 255 | 4 | | | | 7 | 6 | 3 |

TABLE 4

Further data for % inhibition of some compounds of the invention

| Number of compound | % inhibition at 50 µM (or 100 µM if racemate) | | | | | |
|---|---|---|---|---|---|---|
| | Dicty | NM2A | NM2B | NM2C | cardiac | Skeletal | Smooth |
| 174 | 17 | 9 | 9 | 9 | 15 | 77 | 6 |
| 180 | 67 | 44 | 44 | 55 | 81 | 96 | 38 |
| 183 | 80 | 37 | 45 | 37 | 73 | 93 | 51 |
| 188 | 15 | 9 | 18 | 14 | 8 | 95 | 11 |
| 189 | 0 | 7 | −5 | 13 | 47 | 80 | 7 |
| 198 | 96 | 79 | 80 | 84 | 89 | 99 | 88 |
| 206 | | | | | 39 | 78 | 21 |
| 207 | 5 | | | | 7 | 14 | 6 |
| 208 | 89 | 78 | | 65 | | 93 | 60 |
| 210 | 34 | 14 | | 38 | 73 | 84 | 28 |
| 211 | 85 | 69 | | 67 | 85 | 98 | 74 |
| 212 | 69 | | | 56 | 93 | 97 | 61 |
| 213 | 81 | 51 | | 54 | 84 | 98 | 57 |
| 214 | 59 | 31 | | 34 | 73 | 97 | 52 |
| 215 | 63 | | | 56 | 84 | 96 | 45 |
| 216 | 58 | | | 51 | 85 | 95 | 39 |
| 218 | 39 | | | 11 | 75 | 85 | 24 |
| 219 | 56 | | | 18 | 78 | 91 | 32 |
| 220 | 0 | 22 | | 21 | 37 | 94 | 54 |
| 221 | 85 | | | 56 | 78 | 91 | 87 |
| 222 | 99 | | | 89 | 92 | 95 | 97 |
| 223 | 96 | | | 82 | 93 | 95 | 99 |
| 224 | 86 | | | 91 | 96 | 98 | 96 |
| 225 | 97 | | | 74 | 96 | 95 | 96 |
| 226 | 83 | | | 90 | 83 | 92 | 79 |
| 227 | 96 | | | 80 | 89 | 96 | 92 |
| 229 | 95 | | | 98 | 87 | 96 | 87 |
| 230 | 90 | | | 89 | 93 | 92 | 96 |
| 231 | 0 | | | | 5 | 7 | 2 |
| 233 | 76 | | | 69 | 87 | 98 | 70 |
| 235 | 45 | | | | 70 | 100 | 79 |
| 238 | 38 | | | 38 | 47 | 93 | 28 |
| 240 | 26 | | | | 31 | 83 | 23 |
| 247 | 22 | | | | 43 | 96 | 15 |
| 248 | 7 | | | | 1 | 56 | 0 |
| 249 | 39 | | | | 52 | 97 | 55 |
| 250 | 50 | | | | 64 | 98 | 99 |
| 251 | 1 | | | | 13 | 85 | 25 |
| 255 | 18 | | | | 7 | 7 | 3 |

TABLE 5

Further data for % inhibition of some compounds of the invention

| Number of compound | % inhibition, complete | | | | | |
|---|---|---|---|---|---|---|
| | Dicty | NM2A | NM2B | NM2C | cardiac | Skeletal | Smooth |
| 174 | 20 | 12 | 12 | 9 | 100 | 100 | 51 |
| 180 | 85 | 48 | 60 | 60 | 89 | 99 | 58 |
| 183 | 100 | 100 | 56 | 83 | 84 | 95 | 66 |
| 188 | 19 | 31 | 19 | 15 | 32 | 100 | 100 |
| 189 | 0 | 8 | 0 | 13 | 72 | 92 | 8 |
| 198 | 100 | 100 | 100 | 100 | 100 | 100 | 100 |
| 206 | | | | | 47 | 100 | 24 |
| 207 | 0 | | | | 8 | 15 | 7 |
| 208 | 95 | 89 | | 69 | | 95 | 66 |
| 210 | 100 | 100 | | 41 | 82 | 94 | 37 |
| 211 | 100 | 99 | | 70 | 87 | 98 | 85 |
| 212 | 84 | | | 61 | 100 | 98 | 74 |
| 213 | 87 | 74 | | 63 | 87 | 99 | 78 |
| 214 | 100 | 32 | | 36 | 86 | 100 | 100 |
| 215 | 78 | | | 77 | 94 | 98 | 47 |
| 216 | 74 | | | 75 | 89 | 98 | 46 |
| 218 | 100 | | | 20 | 79 | 92 | 28 |
| 219 | 100 | | | 21 | 84 | 94 | 36 |
| 220 | 0 | 20 | | 24 | 39 | 96 | 51 |
| 221 | 100 | | | 61 | 79 | 92 | 97 |
| 222 | 100 | | | 91 | 93 | 95 | 98 |
| 223 | 100 | | | 88 | 98 | 95 | 100 |
| 224 | 89 | | | 93 | 99 | 98 | 99 |
| 225 | 100 | | | 78 | 100 | 96 | 100 |
| 226 | 92 | | | 92 | 85 | 93 | 80 |
| 227 | 100 | | | 84 | 90 | 97 | 99 |
| 229 | 97 | | | 100 | 93 | 97 | 93 |
| 230 | 100 | | | 93 | 96 | 93 | 100 |
| 231 | 0 | | | | 6 | 7 | 5 |
| 233 | 100 | | | 72 | 88 | 98 | 83 |
| 235 | 46 | | | | 71 | 100 | 81 |
| 238 | 41 | | | 40 | 100 | 96 | 31 |
| 240 | 26 | | | | 37 | 91 | 24 |
| 247 | 54 | | | | 70 | 99 | 29 |
| 248 | 100 | | | | 2 | 70 | 0 |
| 249 | 47 | | | | 90 | 100 | 69 |
| 250 | 68 | | | | 76 | 99 | 100 |
| 251 | 1 | | | | 15 | 93 | 100 |
| 255 | 33 | | | | 7 | 7 | 3 |

TABLE 6

Further data for % inhibition of some compounds of the invention

| Number of compound | IC50 (µM) | | | | | | |
|---|---|---|---|---|---|---|---|
| | Dicty | NM2A | NM2B | NM2C | cardiac | Skeletal | Smooth |
| 174 | 10 | 1 | 15 | 2 | 100< | 17 | 100< |
| 180 | 13.1 | 9.8 | 18.7 | 9.3 | 5.1 | 0.81 | 14 |
| 183 | 13 | 87 | 12 | 60 | 8 | 1 | 15 |
| 188 | 13 | 82 | 5 | 4 | 100< | 5 | 100< |
| 189 | 100< | 6 | 100< | 1 | 26 | 7 | 1 |
| 198 | 5.0 | 15.0 | 15.1 | 6.8 | 4.0 | 1.0 | 7.6 |
| 206 | | | | | 10 | 14 | 9 |
| 207 | 100< | | | | 3.7 | 5.8 | 1 |
| 208 | 3.6 | 7.2 | | 1.7 | | 0.36 | 7.8 |
| 210 | 100< | 100< | | 5.2 | 6.0 | 5.6 | 12.5 |
| 211 | 9.4 | 22 | | 2.0 | 1.3 | 0.28 | 7 |
| 212 | 10.9 | | | 6.4 | 5.9 | 0.19 | 10.4 |
| 213 | 3.5 | 23 | | 8.0 | 1.8 | 0.58 | 18 |
| 214 | 36 | 1.0 | | 2.9 | 8.8 | 1.2 | 49 |
| 215 | 12.1 | | | 19 | 5.6 | 1.1 | 2.3 |
| 216 | 13.3 | | | 23 | 2.4 | 1.6 | 8.3 |
| 218 | 78 | | | 44 | 2.7 | 4.2 | 8.1 |
| 219 | 43 | | | 8.1 | 4.1 | 1.8 | 6.9 |
| 220 | 100< | 0.93 | | 1.8 | 5.6 | 0.49 | 2.3 |
| 221 | 11.6 | | | 4.1 | 0.90 | 1.8 | 6.0 |
| 222 | 4.7 | | | 0.76 | 0.52 | 0.11 | 0.86 |

TABLE 6-continued

Further data for % inhibition of some compounds of the invention

| Number of compound | IC50 (µM) | | | | | | |
|---|---|---|---|---|---|---|---|
| | Dicty | NM2A | NM2B | NM2C | cardiac | Skeletal | Smooth |
| 223 | 11.1 | | 3.0 | 2.2 | 0.012 | 1.1 |
| 224 | 2.8 | | | 1.2 | 1.7 | 0.21 | 1.7 |
| 225 | 4.1 | | | 2.8 | 2.4 | 0.17 | 2.2 |
| 226 | 5.5 | | | 1.5 | 0.73 | 0.17 | 0.50 |
| 227 | 5.1 | | | 2.8 | 0.76 | 0.83 | 4.0 |
| 229 | 1.4 | | | 1.1 | 1.4 | 0.61 | 3.4 |
| 230 | 8.1 | | | 2.3 | 1.9 | 0.43 | 3.6 |
| 231 | 100< | | | | 1 | 1.4 | 1 |
| 233 | 17 | | | 2.10 | 0.82 | 0.32 | 8.8 |
| 235 | 0.17 | | | | 0.01 | 0.08 | 0.01 |
| 238 | 3.5 | | | 2.1 | 59 | 0.95 | 6.3 |
| 240 | 0.39 | | | | 8.1 | 4.3 | 1.5 |
| 247 | 71 | | | | 31 | 1.7 | 44 |
| 248 | 100< | | | | 100< | 12 | 100< |
| 249 | 10 | | | | 35 | 1.2 | 13 |
| 250 | 18 | | | | 9 | 0.3 | 1.0 |
| 251 | 100< | | | | 6 | 4.8 | 100< |
| 255 | 42 | | | | 1 | 1.7 | 1 |

Example 6: Presentation of the Effectiveness of Compounds of the Invention

The demonstration of effectiveness was carried out according to the following methodology: actomyosin steady state ATPase measurement on the myosin 2 isoforms of Example 4.

We have shown that for each myosin-2 isoform, a narrow IC50 range can be determined in which maximum inhibitory values can be fine-tuned, which may be of great importance for drug treatments. The results are summarized in the table below.

TABLE 7

Data for refining the maximum inhibition values induced by some of the compounds of the invention in the narrow IC50 range

| Myosin isoform | IC50 range | Inhibition (%) | Number of compound |
|---|---|---|---|
| cardiac | 3-6 µM | 8 | 207 |
| | | 15 | 251 |
| | | 39 | 220 |
| | | 84 | 219 |
| | | 89 | 180 |
| | | 100 | 198 |
| skeletal | 1-2 µM | 7 | 231 |
| | | 7 | 255 |
| | | 92 | 221 |
| | | 94 | 219 |
| | | 98 | 216 |
| | | 100 | 249 |
| smooth | 1-5 µM | 5 | 231 |
| | | 8 | 189 |
| | | 24 | 240 |
| | | 47 | 215 |
| | | 93 | 229 |
| | | 100 | 230 |
| NM2A | 5-10 µM | 8 | 189 |
| | | 48 | 180 |
| | | 89 | 208 |

TABLE 7-continued

Data for refining the maximum inhibition values induced by some of the compounds of the invention in the narrow IC50 range

| Myosin isoform | IC50 range | Inhibition (%) | Number of compound |
|---|---|---|---|
| NM2C | 1-5 μM | 9 | 174 |
| | | 15 | 188 |
| | | 24 | 220 |
| | | 36 | 214 |
| | | 61 | 221 |
| | | 72 | 233 |
| | | 84 | 227 |
| | | 93 | 230 |
| Dicty | 1-11 μM | 20 | 174 |
| | | 41 | 238 |
| | | 84 | 212 |
| | | 87 | 213 |
| | | 92 | 226 |
| | | 95 | 208 |
| | | 100 | 225 |

Example 7: Demonstration of the Effectiveness of Compounds of the Invention

The demonstration of effectiveness was carried out according to the following methodology: isometric force measurement of live, anesthetized rat m. quadriceps femoris on the muscles due to electrical stimulation.

The maximum isometric force induced by the stimulation was determined after intraperitoneal injection of some of the compounds of the invention. During the measurement, the following parameters of live anesthetized rats were continuously monitored:

a) heart rate b) blood flow in the neck arteries c) respiratory frequency d) blood oxygen saturation ratio Results from live anesthetized rats are summarized in the table below.

TABLE 8

Data on the effectiveness of some of the compounds of the present invention in an in vivo measurement system

| Number of compound | i.p. injected amount (mg) to to 200-300 rat | Maximum change of vital parameters (%) | | | | Maximum change in isometric force at rear leg (%) |
|---|---|---|---|---|---|---|
| | | heart rate | blood flow | respiratory frequency | oxygen saturation | |
| Control | 0 | 7 | 14 | −12 | −10 | 14 |
| 174 | 6 | 3 | 4 | −20 | −19 | 25 |
| 188 | 1 | 3 | 15 | −18 | −16 | 23 |
| | 3 | −3 | −5 | 5 | −3 | 26 |
| | 6 | −9 | −1 | −1 | −1 | 28 |
| | 9 | −12 | 9 | −40 | −27 | |
| 220 | 1 | 1 | 8 | −13 | −1 | 19 |
| | 3 | 8 | 19 | −21 | −17 | 23 |
| | 6 | 22 | −1 | −22 | −28 | 42 |
| | 10 | 3 | −3 | −30 | −41 | |
| 223 | 0.2 | 5 | 8 | −13 | −10 | 23 |
| | 1 | 19 | 25 | −22 | −7 | 25 |
| 238 | 6 | 3 | −10 | −18 | −12 | 40 |

Example 8: Demonstration of the Effectiveness of Compounds of the Invention

To demonstrate effectiveness, the following methodology was used: 6 mg of 188 compound was injected intraperitoneally into a live rat and tissue concentrations determined in the following tissues at specific times:

a) blood b) brain c) lung d) myocardium e) liver f) kidney g) spleen h) skeletal muscle i) urine The results of the rat tissues are summarized in the following tables.

TABLE 9

Data for tissue distribution of some of the compounds of the invention in an in vivo measurement system

| time after i.p. injection (min) of 6 mg of compound 188 | Concentration of compound 188 in tissue samples (µM) | | | | | | | |
|---|---|---|---|---|---|---|---|---|
| | blood | brain | lung | myocardium | liver | kidney | spleen | muscle | urine |
| 5 | 12 | 25 | 25 | 36 | 30 | 29 | 37 | 22 | 58 |
| 15 | 16 | 45 | 36 | 48 | 18 | 56 | 28 | 48 | 77 |
| 30 | 12 | 36 | 22 | 26 | 12 | 20 | 11 | 69 | 72 |
| 45 | 10 | 17 | 9 | 18 | 9 | 12 | 5 | 78 | 63 |
| 60 | 8 | 5 | 4 | 9 | 3 | 3 | 3 | 74 | 21 |

Example 9: Demonstration of Solubility of the Compounds of the Invention

The solubility of the compounds in phosphate buffered saline (Dulbecco's Phosphate Buffered Saline, w/o Mg, Ca (PBS)) was tested in the presence of 1% DMSO. The specified solubility values are given in the table below.

TABLE 10

Data for maximum solubility in PBS-1% DMSO solution

| Number of compound | Maximum solubility in PBS-1% DMSO solution |
|---|---|
| 174 | ≥1000 µM |
| 180 | 2400 µM |
| 188 | 1450 µM |
| 210 | 1360 µM |
| 211 | 510 µM |
| 213 | 410 µM |
| 214 | 820 µM |
| 220 | 710 µM |

Example 10: Demonstration of Mutagenicity of the Compounds of the Invention

Mutagenicity of the compounds was determined in the Ames Reverse Mutagenicity Assay (Ames MPF Test, Xenometrix Inc.) approved by the OECD, EMA and FDA on *S. typhimurium* TA98 and TA100 strains without or in the presence of S9 rat liver fraction. Relative mutagenicity values were prepared using a table provided by the manufacturer. Relative mutagenicity values according to OECD, EMA, and FDA standards may not exceed 2 at any concentration because in such a case they are potertially mutagenic. The relative mutagenicity values are shown in the table and FIGURE below.

TABLE 11

Data for mutagenicity testing for S(−)-blebbistatin and compound 188

| Concentration of the inhibitor (µM) | Relative mutagenicity (as compared to the control value) | | | | | | | |
|---|---|---|---|---|---|---|---|---|
| | S(−)-blebbistatin (control) | | | | Compound 188 | | | |
| | TA98 | | TA100 | | TA98 | | TA100 | |
| | −S9 | +S9 | −S9 | +S9 | −S9 | +S9 | −S9 | +S9 |
| 3.125 | 1.3 | 0.8 | 1.1 | 0.9 | | | | |
| 6.25 | 1.2 | 0.7 | 1.2 | 1.0 | | | | |
| 12.5 | 1.7 | 0.7 | 1.5 | 1.4 | | | | |
| 25 | 1.9 | 1.2 | 1.2 | 1.1 | | | | |
| 31.25 | | | | | 1.2 | 0.2 | 0.8 | 0.4 |
| 50 | 2.7 | 1.4 | 1.7 | 1.9 | | | | |
| 62.5 | | | | | 0.3 | 0.2 | 0.5 | 0.3 |
| 100 | 4.9 | 3.9 | 2.5 | 2.6 | | | | |
| 125 | | | | | 0.7 | 0.4 | 0.6 | 0.6 |
| 250 | | | | | 0.3 | 0.4 | 0.5 | 0.6 |
| 500 | | | | | 0.7 | 0.4 | 0.6 | 0.6 |
| 1000 | | | | | 1.0 | 0.2 | 0.7 | 0.5 |

Example 11: Examples of the Compounds of the Invention Include the Following Compounds that are not to be Construed as Limiting the Invention

| Structure | IUPAC name | Q1 | Q2 | Q3 | Q4 | Q5 | Q6 | Q7 | R1 |
|---|---|---|---|---|---|---|---|---|---|
| 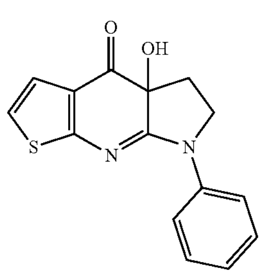 [SMILES: O=C1c2ccsc2N=C2N(c3ccccc3)CCC12O] | 9-hydroxy-12-phenyl-4-thia-2,12-diazatricyclo[7.3.0.0$^{3,7}$]dodeca-1,3(7),5-trien-8-one | — | — | — | — | S | CH | CH | phenyl |

| Structure | IUPAC name | Q1 | Q2 | Q3 | Q4 | Q5 | Q6 | Q7 | R1 |
|---|---|---|---|---|---|---|---|---|---|
| | 12-(4-aminophenyl)-9-hydroxy-4-thia-2,12-diazatricyclo[7.3.0.0³,⁷]dodeca-1,3(7),5-trien-8-one | — | — | — | — | S | CH | CH | 4-aminophenyl |
| | 9-hydroxy-12-(4-nitrophenyl)-4-thia-2,12-diazatricyclo[7.3.0.0³,⁷]dodeca-1,3(7),5-trien-8-one | — | — | — | — | S | CH | CH | 4-nitrophenyl |
| | 9-hydroxy-12-(piridin-4-yl)-4-thia-2,12-diazatricyclo[7.3.0.0³,⁷]dodeca-1,3(7),5-trien-8-one | — | — | — | — | S | CH | CH | pyridin-4-yl |
| | 4-{9-hydroxy-8-oxo-4-thia-2,12-diazatricyclo[7.3.0.0³,⁷]dodeca-1,3(7),5-trien-12-yl}benzamide | — | — | — | — | S | CH | CH | 4-(carboxamido)phenyl |
| | 4-{9-hydroxy-8-oxo-4-thia-2,12-diazatricyclo[7.3.0.0³,⁷]dodeca-1,3(7),5-trien-12-yl}benzonitrile | — | — | — | — | S | CH | CH | 4-cyanophenyl |

-continued

| Structure | IUPAC name | Q1 | Q2 | Q3 | Q4 | Q5 | Q6 | Q7 | R1 |
|---|---|---|---|---|---|---|---|---|---|
| 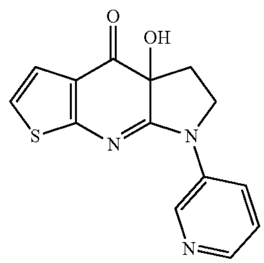 [SMILES: O=C1c2ccsc2N=C2N(c3cccnc3)CCC12O] | 9-hydroxy-12-(pyridin-3-yl)-4-thia-2,12-diazatricyclo[7.3.0.0$^{3,7}$]dodeca-1,3(7),5-trien-8-one | — | — | — | — | S | CH | CH | pyridin-3-yl |
| 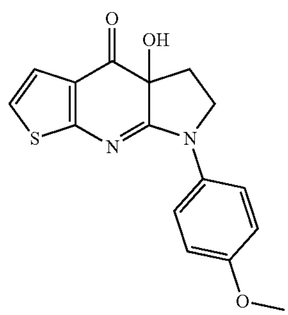 [SMILES: COc1ccc(N2CCC3(O)C(=O)c4ccsc4N=C23)cc1] | 9-hydroxy-12-(4-methoxyphenyl)-4-thia-2,12-diazatricyclo[7.3.0.0$^{3,7}$]dodeca-1,3(7),5-trien-8-one | — | — | — | — | S | CH | CH | 4-methoxyphenyl |
| 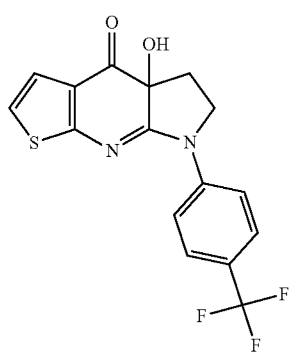 [SMILES: O=C1c2ccsc2N=C2N(c3ccc(C(F)(F)F)cc3)CCC12O] | 9-hydroxy-12-[4-(trifluoromethyl)phenyl]-4-thia-2,12-diazatricyclo[7.3.0.0$^{3,7}$]dodeca-1,3(7),5-trien-8-one | — | — | — | — | S | CH | CH | 4-(trifluoromethyl)phenyl |
| 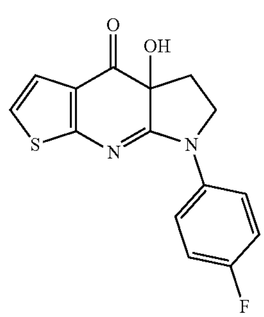 [SMILES: O=C1c2ccsc2N=C2N(c3ccc(F)cc3)CCC12O] | 12-(4-fluorphenyl)-9-hydroxy-4-thia-2,12-diazatricyclo[7.3.0.0$^{3,7}$]dodeca-1,3(7),5-trien-8-one | — | — | — | — | S | CH | CH | 4-fluorophenyl |

-continued

| Structure | IUPAC name | Q1 | Q2 | Q3 | Q4 | Q5 | Q6 | Q7 | R1 |
|---|---|---|---|---|---|---|---|---|---|
| | 9-hydroxy-12-[4-(trifluoromethoxy)phenyl]-4-thia-2,12-diazatricyclo[7.3.0.0³,⁷]dodeca-1,3(7),5-trien-8-one | — | — | — | — | S | CH | CH | 4-(trifluoromethoxy)-phenyl |
| | 12-[4-(dimethylamino)phenyl]-9-hydroxy-4-thia-2,12-diazatricyclo[7.3.0.0³,⁷]dodeca-1,3(7),5-trien-8-one | — | — | — | — | S | CH | CH | 4-(dimethylamino)-phenyl |
| | 12-(3-aminophenyl)-9-hydroxy-4-thia-2,12-diazatricyclo[7.3.0.0³,⁷]dodeca-1,3(7),5-trien-8-one | — | — | — | — | S | CH | CH | 3-aminophenyl |
| | 9-hydroxy-12-[4-(hydroxymethyl)phenyl]-4-thia-2,12-diazatricyclo[7.3.0.0³,⁷]dodeca-1,3(7),5-trien-8-one | — | — | — | — | S | CH | CH | 4-(hydroxymethyl)-phenyl |

| Structure | IUPAC name | Q1 | Q2 | Q3 | Q4 | Q5 | Q6 | Q7 | R1 |
|---|---|---|---|---|---|---|---|---|---|
| 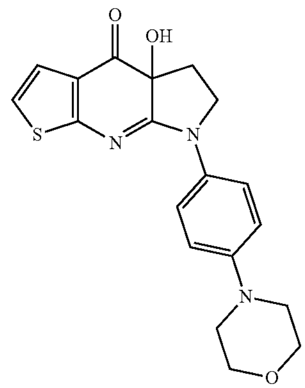 [SMILES: O=C1c2ccsc2N=C2N(c3ccc(N4CCOCC4)cc3)CCC12O] | 9-hydroxy-12-[4-(morpholin-4-yl)phenyl]-4-thia-2,12-diazatricyclo[7.3.0.0$^{3,7}$]dodeca-1,3(7),5-trien-8-one | — | — | — | — | S | CH | CH | 4-(morpholin-4-yl)phenyl |
| 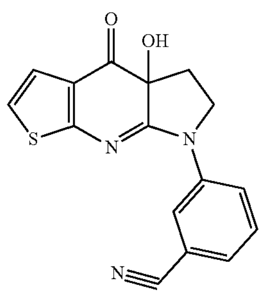 [SMILES: N#Cc1cccc(N2CCC3(O)C(=O)c4ccsc4N=C23)c1] | 3-{9-hydroxy-8-oxo-4-thia-2,12-diazatricyclo[7.3.0.0$^{3,7}$]dodeca-1,3(7),5-trien-12-yl}benzonitrile | — | — | — | — | S | CH | CH | 3-cyanophenyl |
| 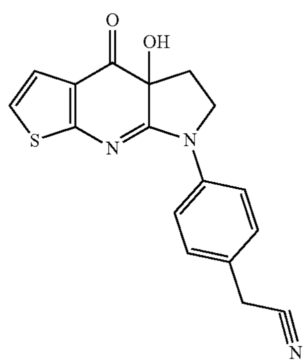 [SMILES: N#CCc1ccc(N2CCC3(O)C(=O)c4ccsc4N=C23)cc1] | 2-(4-{9-hydroxy-8-oxo-4-thia-2,12-diazatricyclo[7.3.0.0$^{3,7}$]dodeca-1,3(7),5-trien-12-yl}phenyl)acetonitrile | — | — | — | — | S | CH | CH | 4-(cyanomethyl)phenyl |
| 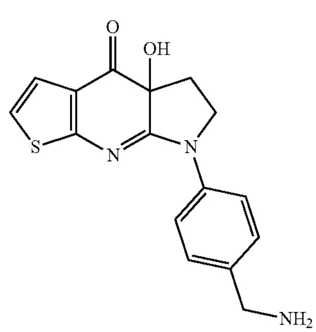 [SMILES: NCc1ccc(N2CCC3(O)C(=O)c4ccsc4N=C23)cc1] | 12-[4-(aminomethyl)phenyl]-9-hydroxy-4-thia-2,12-diazatricyclo[7.3.0.0$^{3,7}$]dodeca-1,3(7),5-trien-8-one | — | — | — | — | S | CH | CH | 4-(aminomethyl)phenyl |

-continued

| Structure | IUPAC name | Q1 | Q2 | Q3 | Q4 | Q5 | Q6 | Q7 | R1 |
|---|---|---|---|---|---|---|---|---|---|
| | N-[(4-{9-hydroxy-8-oxo-4-thia-2,12-diazatricyclo[7.3.0.0³,⁷]dodeca-1,3(7),5-trien-12-yl}phenyl)methyl]methanesulfonamid | — | — | — | — | S | CH | CH | 4-(methanesulfonamidomethyl)phenyl |
| | 9-hydroxy-12-(3-methoxyphenyl)-4-thia-2,12-diazatricyclo[7.3.0.0³,⁷]dodeca-1,3(7),5-trien-8-one | — | — | — | — | S | CH | CH | 3-methoxyphenyl |
| | 2-(4-{9-hydroxy-8-oxo-4-thia-2,12-diazatricyclo[7.3.0.0³,⁷]dodeca-1,3(7),5-trien-12-yl}phenyl)-N,N-dimethyl-acetamide | — | — | — | — | S | CH | CH | N,N-dimethylphenylacetamid-4-yl |
| | 1,1,1-trifluoro-N-(4-{9-hydroxy-8-oxo-4-thia-2,12-diazatricyclo[7.3.0.0³,⁷]dodeca-1,3(7),5-trien-12-yl}phenyl)methanesulfonamide | — | — | — | — | S | CH | CH | 4-(trifluoromethanesulfonylamino)phenyl |

-continued

| Structure | IUPAC name | Q1 | Q2 | Q3 | Q4 | Q5 | Q6 | Q7 | R1 |
|---|---|---|---|---|---|---|---|---|---|
| 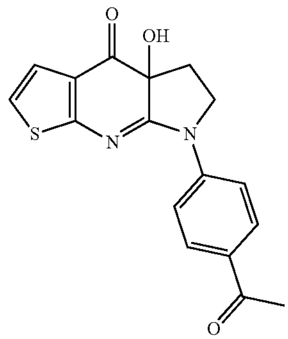 [SMILES: CC(=O)c1ccc(N2CCC3(O)C(=O)c4ccsc4N=C23)cc1] | 12-(4-acetylphenyl)-9-hydroxy-4-thia-2,12-diazatricyclo[7.3.0.0$^{3,7}$]dodeca-1,3(7),5-trien-8-one | — | — | — | — | S | CH | CH | 4-acetyl-phenyl |
| 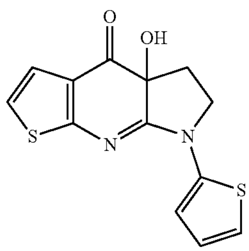 [SMILES: O=C1c2ccsc2N=C2N(c3cccs3)CCC12O] | 9-hydroxy-12-(thiophen-2-yl)-4-thia-2,12-diazatricyclo[7.3.0.0$^{3,7}$]dodeca-1,3(7),5-trien-8-one | — | — | — | — | S | CH | CH | thiophen-2-yl |
| 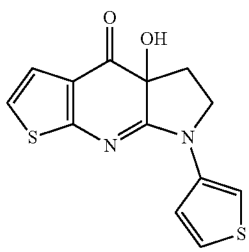 [SMILES: O=C1c2ccsc2N=C2N(c3ccsc3)CCC12O] | 9-hydroxy-12-(thiophen-3-yl)-4-thia-2,12-diazatricyclo[7.3.0.0$^{3,7}$]dodeca-1,3(7),5-trien-8-one | — | — | — | — | S | CH | CH | thiophen-3-yl |
| 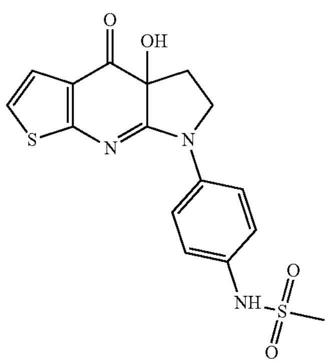 [SMILES: CS(=O)(=O)Nc1ccc(N2CCC3(O)C(=O)c4ccsc4N=C23)cc1] | N-(4-{9-hydroxy-8-oxo-4-thia-2,12-diazatricyclo[7.3.0.0$^{3,7}$]dodeca-1,3(7),5-trien-12-yl}phenyl)methane-sulfonamide | — | — | — | — | S | CH | CH | 4-(methane-sulfonyl-amino)phenyl |
| 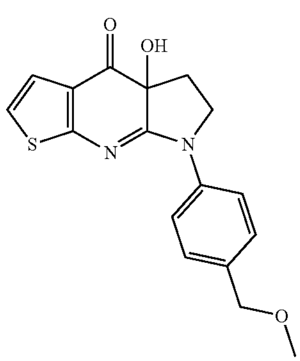 [SMILES: COCc1ccc(N2CCC3(O)C(=O)c4ccsc4N=C23)cc1] | 9-hydroxy-12-[4-(methoxymethyl)phenyl]-4-thia-2,12-diazatricyclo[7.3.0.0$^{3,7}$]dodeca-1,3(7),5-trien-8-one | — | — | — | — | S | CH | CH | 4-(methoxy-methyl)phenyl |

-continued

| Structure | IUPAC name | Q1 | Q2 | Q3 | Q4 | Q5 | Q6 | Q7 | R1 |
|---|---|---|---|---|---|---|---|---|---|
| | 9-hydroxy-12-(2-methoxypyridin-4-yl)-4-thia-2,12-diazatricyclo[7.3.0.0³,⁷]dodeca-1,3(7),5-trien-8-one | — | — | — | — | S | CH | CH | 2-methoxy-pyridin-4-yl |
| | 9-hydroxy-12-(6-methoxypyridin-3-yl)-4-thia-2,12-diazatricyclo[7.3.0.0³,⁷]dodeca-1,3(7),5-trien-8-one | — | — | — | — | S | CH | CH | 6-methoxy-pyridin-3-yl |
| | 9-hydroxy-5-methyl-12-phenyl-4-thia-2,12-diazatricyclo[7.3.0.0³,⁷]dodeca-1,3(7),5-trien-8-one | — | — | — | — | S | CMe | CH | phenyl |
| | 12-(4-aminophenyl)-9-hydroxy-5-methyl-4-thia-2,12-diazatricyclo[7.3.0.0³,⁷]dodeca-1,3(7),5-trien-8-one | — | — | — | — | S | CMe | CH | 4-amino-phenyl |
| | 9-hydroxy-5-methyl-12-(4-nitrophenyl)-4-thia-2,12-diazatricyclo[7.3.0.0³,⁷]dodeca-1,3(7),5-trien-8-one | — | — | — | — | S | CMe | CH | 4-nitro-phenyl |

-continued

| Structure | IUPAC name | Q1 | Q2 | Q3 | Q4 | Q5 | Q6 | Q7 | R1 |
|---|---|---|---|---|---|---|---|---|---|
| | 9-hydroxy-5-methyl-12-(pyridin-4-yl)-4-thia-2,12-diazatricyclo[7.3.0.0³,⁷]dodeca-1,3(7),5-trien-8-one | — | — | — | — | S | CMe | CH | pyridin-4-yl |
| | 4-{9-hydroxy-5-methyl-8-oxo-4-thia-2,12-diazatricyclo[7.3.0.0³,⁷]dodeca-1,3(7),5-trien-12-yl}benzamide | — | — | — | — | S | CMe | CH | 4-(carboxamido)phenyl |
| | 4-{9-hydroxy-5-methyl-8-oxo-4-thia-2,12-diazatricyclo[7.3.0.0³,⁷]dodeca-1,3(7),5-trien-12-yl}benzonitrile | — | — | — | — | S | CMe | CH | 4-cyanophenyl |
| | 9-hydroxy-5-methyl-12-(pyridin-3-yl)-4-thia-2,12-diazatricyclo[7.3.0.0³,⁷]dodeca-1,3(7),5-trien-8-one | — | — | — | — | S | CMe | CH | pyridin-3-yl |
| | 9-hydroxy-12-(4-methoxyphenyl)-5-methyl-4-thia-2,12-diazatricyclo[7.3.0.0³,⁷]dodeca-1,3(7),5-trien-8-one | — | — | — | — | S | CMe | CH | 4-methoxyphenyl |

| Structure | IUPAC name | Q1 | Q2 | Q3 | Q4 | Q5 | Q6 | Q7 | R1 |
|---|---|---|---|---|---|---|---|---|---|
| | 9-hydroxy-5-methyl-12-[4-(trifluoromethyl)phenyl]-4-thia-2,12-diazatricyclo[7.3.0.0³,⁷]dodeca-1,3(7),5-trien-8-one | — | — | — | — | S | CMe | CH | 4-(trifluoromethyl)phenyl |
| | 12-(4-fluorphenyl)-9-hydroxy-5-methyl-4-thia-2,12-diazatricyclo[7.3.0.0³,⁷]dodeca-1,3(7),5-trien-8-one | — | — | — | — | S | CMe | CH | 4-fluorophenyl |
| | 9-hydroxy-5-methyl-12-[4-(trifluoromethoxy)phenyl]-4-thia-2,12-diazatricyclo[7.3.0.0³,⁷]dodeca-1,3(7),5-trien-8-one | — | — | — | — | S | CMe | CH | 4-(trifluoromethoxy)phenyl |
| | 12-[4-(dimethylamino)phenyl]-9-hydroxy-5-methyl-4-thia-2,12-diazatricyclo[7.3.0.0³,⁷]dodeca-1,3(7),5-trien-8-one | — | — | — | — | S | CMe | CH | 4-(dimethylamino)phenyl |

-continued

| Structure | IUPAC name | Q1 | Q2 | Q3 | Q4 | Q5 | Q6 | Q7 | R1 |
|---|---|---|---|---|---|---|---|---|---|
| | 12-(3-aminophenyl)-9-hydroxy-5-methyl-4-thia-2,12-diazatricyclo[7.3.0.0³,⁷]dodeca-1,3(7),5-trien-8-one | — | — | — | — | S | CMe | CH | 3-aminophenyl |
| | 9-hydroxy-12-[4-(hydroxymethyl)phenyl]-5-methyl-4-thia-2,12-diazatricyclo[7.3.0.0³,⁷]dodeca-1,3(7),5-trien-8-one | — | — | — | — | S | CMe | CH | 4-(hydroxymethyl)phenyl |
| | 9-hydroxy-5-methyl-12-[4-(morpholin-4-yl)phenyl]-4-thia-2,12-diazatricyclo[7.3.0.0³,⁷]dodeca-1,3(7),5-trien-8-one | — | — | — | — | S | CMe | CH | 4-(morpholin-4-yl)phenyl |
| | 3-{9-hydroxy-5-methyl-8-oxo-4-thia-2,12-diazatricyclo[7.3.0.0³,⁷]dodeca-1,3(7),5-trien-12-yl}benzonitrile | — | — | — | — | S | CMe | CH | 3-cyanophenyl |

-continued

| Structure | IUPAC name | Q1 | Q2 | Q3 | Q4 | Q5 | Q6 | Q7 | R1 |
|---|---|---|---|---|---|---|---|---|---|
| 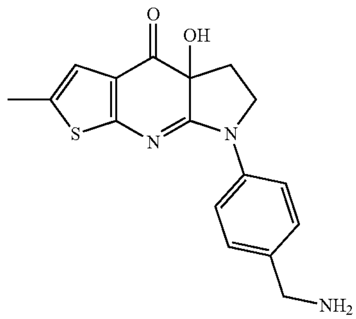 [SMILES: Cc1cc2c(s1)N=C1N(c3ccc(CN)cc3)CCC1(O)C2=O] | 12-[4-(aminomethyl)phenyl]-9-hydroxy-5-methyl-4-thia-2,12-diazatricyclo[7.3.0.0$^{3,7}$]dodeca-1,3(7),5-trien-8-one | — | — | — | — | S | CMe | CH | 4-(aminomethyl)phenyl |
| 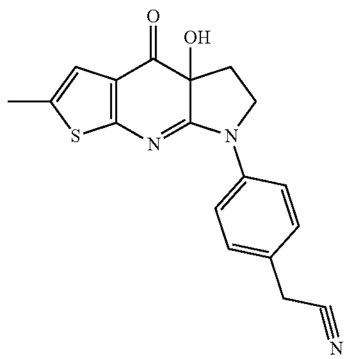 [SMILES: Cc1cc2c(s1)N=C1N(c3ccc(CC#N)cc3)CCC1(O)C2=O] | 2-(4-{9-hydroxy-5-methyl-8-oxo-4-thia-2,12-diazatricyclo[7.3.0.0$^{3,7}$]dodeca-1,3(7),5-trien-12-yl}phenyl)acetonitrile | — | — | — | — | S | CMe | CH | 4-(cyanomethyl)phenyl |
| 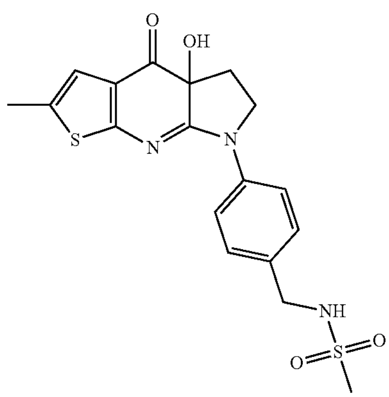 [SMILES: Cc1cc2c(s1)N=C1N(c3ccc(CNS(C)(=O)=O)cc3)CCC1(O)C2=O] | N-[(4-{9-hydroxy-5-methyl-8-oxo-4-thia-2,12-diazatricyclo[7.3.0.0$^{3,7}$]dodeca-1,3(7),5-trien-12-yl}phenyl)methyl]methanesulfonamide | — | — | — | — | S | CMe | CH | 4-(methanesulfonamidomethyl)phenyl |
| 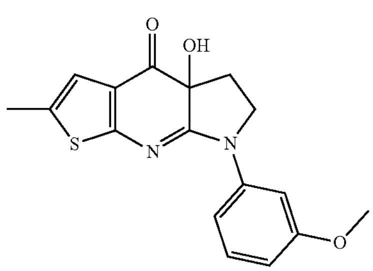 | 9-hydroxy-12-(3-methoxyphenyl)-5-methyl-4-thia-2,12-diazatricyclo[7.3.0.0$^{3,7}$]dodeca-1,3(7),5-trien-8-one | — | — | — | — | S | CMe | CH | 3-methoxyphenyl |

-continued

| Structure | IUPAC name | Q1 | Q2 | Q3 | Q4 | Q5 | Q6 | Q7 | R1 |
|---|---|---|---|---|---|---|---|---|---|
| | 1,1,1-trifluoro-N-(4-{9-hydroxy-5-methyl-8-oxo-4-thia-2,12-diazatricyclo[7.3.0.0³,⁷]dodeca-1,3(7),5-trien-12-yl}phenyl)methanesulfonamide | — | — | — | — | S | CMe | CH | 4-(trifluoromethansulfonilamino)phenyl |
| | 2-(4-{9-hydroxy-5-methyl-8-oxo-4-thia-2,12-diazatricyclo[7.3.0.0³,⁷]dodeca-1,3(7),5-trien-12-yl}phenyl)-N,N-dimethylacetamide | — | — | — | — | S | CMe | CH | N,N-dimethyl-phenylacetamid-4-yl |
| | 12-(4-acetylphenyl)-9-hydroxy-5-methyl-4-thia-2,12-diazatricyclo[7.3.0.0³,⁷]dodeca-1,3(7),5-trien-8-one | — | — | — | — | S | CMe | CH | 4-acetylphenyl |
| | 9-hydroxy-5-methyl-12-(thiophen-2-yl)-4-thia-2,12-diazatricyclo[7.3.0.0³,⁷]dodeca-1,3(7),5-trien-8-one | — | — | — | — | S | CMe | CH | thiophen-2-yl |
| | 9-hydroxy-5-methyl-12-(thiophen-3-yl)-4-thia-2,12-diazatricyclo[7.3.0.0³,⁷]dodeca-1,3(7),5-trien-8-one | — | — | — | — | S | CMe | CH | thiophen-3-yl |

-continued

| Structure | IUPAC name | Q1 | Q2 | Q3 | Q4 | Q5 | Q6 | Q7 | R1 |
|---|---|---|---|---|---|---|---|---|---|
| | N-(4-{9-hydroxy-5-methyl-8-oxo-4-thia-2,12-diazatricyclo[7.3.0.0³,⁷]dodeca-1,3(7),5-trien-12-yl}phenyl)methane-sulfonamide | — | — | — | — | S | CMe | CH | 4-(methane-sulfonyl-amino)phenyl |
| | 9-hydroxy-12-[4-(methoxymethyl)phenyl]-5-methyl-4-thia-2,12-diazatricyclo[7.3.0.0³,⁷]dodeca-1,3(7),5-trien-8-one | — | — | — | — | S | CMe | CH | 4-(methoxy-methyl)phenyl |
| | 9-hydroxy-12-(2-methoxy-pyridin-4-yl)-5-methyl-4-thia-2,12-diazatricyclo[7.3.0.0³,⁷]dodeca-1,3(7),5-trien-8-one | — | — | — | — | S | CMe | CH | 2-methoxy-pyridin-4-yl |
| | 9-hydroxy-12-(6-methoxypyridin-3-yl-5-methyl-4-thia-2,12-diazatricyclo[7.3.0.0³,⁷]dodeca-1,3(7),5-trien-8-one | — | — | — | — | S | CMe | CH | 6-methoxy-pyridin-3-yl |
| | 3a-hydroxy-1-phenyl-1H,2H,3H,3aH,4H-pyrrolo[2,3-b]1,7-naphthyridin-4-one | CH | N | CH | CH | — | — | — | phenyl |

-continued

| Structure | IUPAC name | Q1 | Q2 | Q3 | Q4 | Q5 | Q6 | Q7 | R1 |
|---|---|---|---|---|---|---|---|---|---|
| 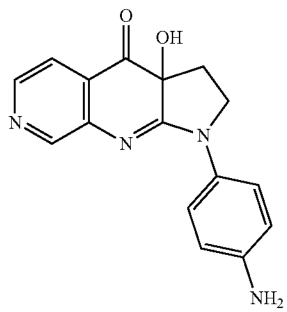 [SMILES: Nc1ccc(N2CCC3(O)C(=O)c4ccncc4N=C23)cc1] | 1(4-aminophenyl)-3a-hydroxy-1H,2H,3H,3aH,4H-pyrrolo[2,3-b]1,7-naphthyridin-4-one | CH | N | CH | CH | — | — | — | 4-aminophenyl |
| 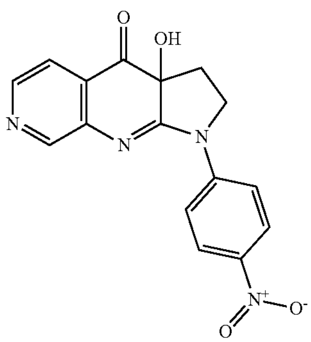 [SMILES: O=C1c2ccncc2N=C2N(c3ccc([N+](=O)[O-])cc3)CCC12O] | 3a-hydroxy-1-(4-nitrophenyl)-1H,2H,3H,3aH,4H-pyrrolo[2,3-b]1,7-naphthyridin-4-one | CH | N | CH | CH | — | — | — | 4-nitrophenyl |
| 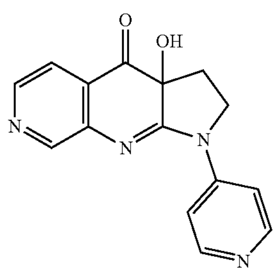 [SMILES: O=C1c2ccncc2N=C2N(c3ccncc3)CCC12O] | 3a-hydroxy-1-(pyridin-4-yl)-1H,2H,3H,3aH,4H-pyrrolo[2,3-b]1,7-naphthyridin-4-one | CH | N | CH | CH | — | — | — | pyridin-4-yl |
| 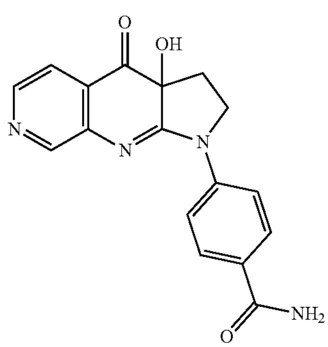 [SMILES: NC(=O)c1ccc(N2CCC3(O)C(=O)c4ccncc4N=C23)cc1] | 4-{3a-hydroxy-4-oxo-1H,2H,3H,3aH,4H-pyrrolo[2,3-b]1,7-naphthyridin-1-yl}benzamide | CH | N | CH | CH | — | — | — | 4-(carboxamido)phenyl |
| 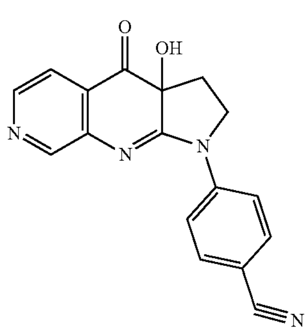 [SMILES: N#Cc1ccc(N2CCC3(O)C(=O)c4ccncc4N=C23)cc1] | 4-{3a-hydroxy-4-oxo-1H,2H,3H,3aH,4H-pyrrolo[2,3-b]1,7-naphthyridin-1-yl}benzonitrile | CH | N | CH | CH | — | — | — | 4-cyanophenyl |

| Structure | IUPAC name | Q1 | Q2 | Q3 | Q4 | Q5 | Q6 | Q7 | R1 |
|---|---|---|---|---|---|---|---|---|---|
| 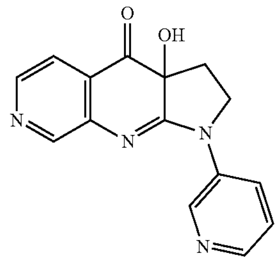 [SMILES: O=C1c2ccncc2N=C2N(c3cccnc3)CCC12O] | 3a-hydroxy-1-(pyridin-3-yl)-1H,2H,3H,3aH,4H-pyrrolo[2,3-b]1,7-naphthyridin-4-one | CH | N | CH | CH | — | — | — | pyridin-3-yl |
| 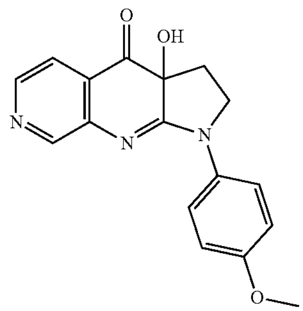 [SMILES: COc1ccc(N2CCC3(O)C(=O)c4ccncc4N=C23)cc1] | 3a-hydroxy-1-(4-methoxyphenyl)-1H,2H,3H,3aH,4H-pyrrolo[2,3-b]1,7-naphthyridin-4-one | CH | N | CH | CH | — | — | — | 4-methoxyphenyl |
| 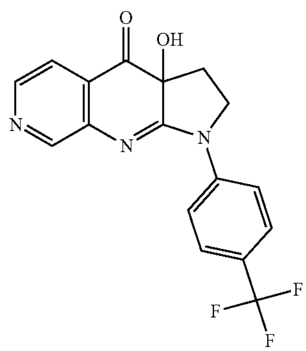 [SMILES: O=C1c2ccncc2N=C2N(c3ccc(C(F)(F)F)cc3)CCC12O] | 3a-hydroxy-1-[4-(trifluoromethyl)phenyl]-1H,2H,3H,3aH,4H-pyrrolo[2,3-b]1,7-naphthyridin-4-one | CH | N | CH | CH | — | — | — | 4-(trifluoromethyl)phenyl |
| 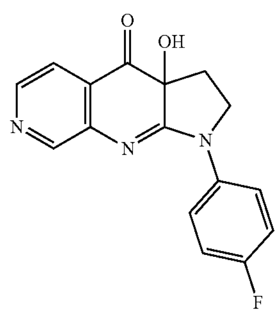 [SMILES: O=C1c2ccncc2N=C2N(c3ccc(F)cc3)CCC12O] | 1-(4-fluorphenyl)-3a-hydroxy-1H,2H,3H,3aH,4H-pyrrolo[2,3-b]1,7-naphthyridin-4-one | CH | N | CH | CH | — | — | — | 4-fluorophenyl |
| 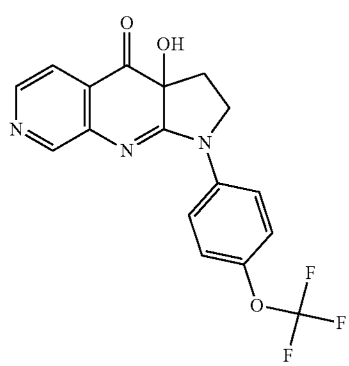 [SMILES: O=C1c2ccncc2N=C2N(c3ccc(OC(F)(F)F)cc3)CCC12O] | 3a-hydroxy-1-[4-(trifluoromethoxy)phenyl]-1H,2H,3H,3aH,4H-pyrrolo[2,3-b]1,7-naphthyridin-4-one | CH | N | CH | CH | — | — | — | 4-(trifluoromethoxy)phenyl |

-continued

| Structure | IUPAC name | Q1 | Q2 | Q3 | Q4 | Q5 | Q6 | Q7 | R1 |
|---|---|---|---|---|---|---|---|---|---|
| 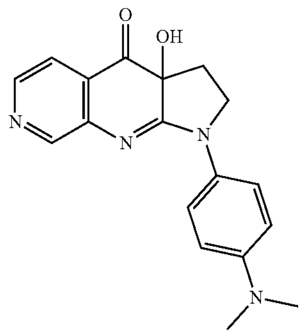 [SMILES: CN(C)c1ccc(N2CCC3(O)C(=O)c4ccncc4N=C23)cc1] | 1-[4-(dimethylamino)phenyl]-3a-hydroxy-1H,2H,3H,3aH4H-pyrrolo[2,3-b]1,7-naphthyridin-4-one | CH | N | CH | CH | — | — | — | 4-(dimethyl-amino)phenyl |
| 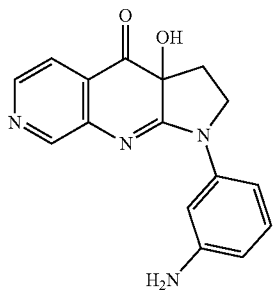 [SMILES: Nc1cccc(N2CCC3(O)C(=O)c4ccncc4N=C23)c1] | 1-(3-aminophenyl)-3a-hydroxy-1H,2H,3H,3aH,4H-pyrrolo[2,3-b]1,7-naphthyridin-4-one | CH | N | CH | CH | — | — | — | 3-amino-phenyl |
| 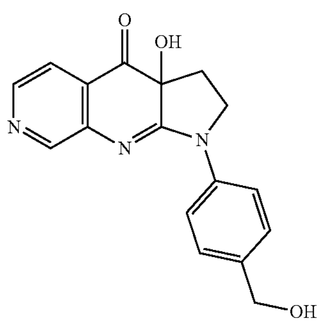 [SMILES: O=C1c2ccncc2N=C2N(c3ccc(CO)cc3)CCC12O] | 3a-hydroxy-1-[4-(hydroxymethyl)phenyl]-1H,2H,3H,3aH,4H-pyrrolo[2,3-b]1,7-naphthyridin-4-one | CH | N | CH | CH | — | — | — | 4-(hydroxy-methyl)phenyl |
| 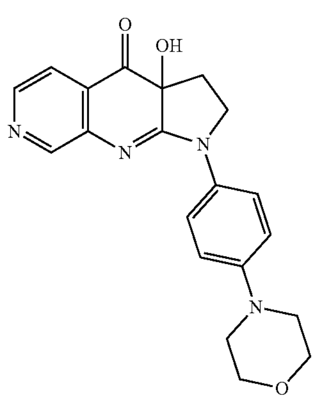 [SMILES: O=C1c2ccncc2N=C2N(c3ccc(N4CCOCC4)cc3)CCC12O] | 3a-hydroxy-1-[4-(morpholin-4-yl)phenyl]-1H,2H,3H,3aH,4H-pyrrolo[2,3-b]1,7-naphthyridin-4-one | CH | N | CH | CH | — | — | — | 4-(morpholin-4-yl)phenyl |

-continued

| Structure | IUPAC name | Q1 | Q2 | Q3 | Q4 | Q5 | Q6 | Q7 | R1 |
|---|---|---|---|---|---|---|---|---|---|
| 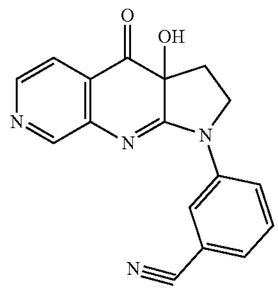 [SMILES: N#Cc1cccc(N2CCC3(O)C(=O)c4ccncc4N=C23)c1] | 3-{3a-hydroxy-4-oxo-1H,2H,3H,3aH,4H-pyrrolo[2,3-b]1,7-naphthyridin-1-yl}benzonitrile | CH | N | CH | CH | — | — | — | 3-cyanophenyl |
| 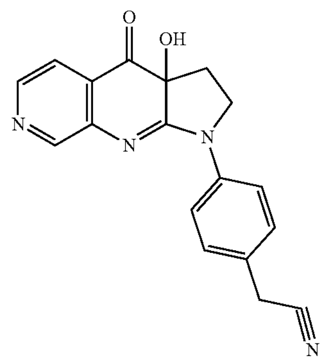 [SMILES: N#CCc1ccc(N2CCC3(O)C(=O)c4ccncc4N=C23)cc1] | 2-(4-{3a-hydroxy-4-oxo-1H,2H,3H,3aH,4H-pyrrolo[2,3-b]1,7-naphthyridin-1-yl}phenyl)acetonitrile | CH | N | CH | CH | — | — | — | 4-(cyanomethyl)phenyl |
| 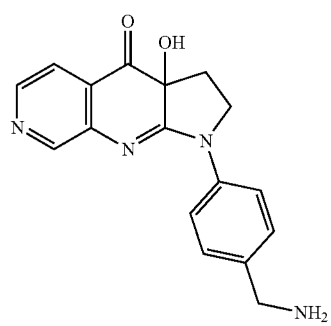 [SMILES: NCc1ccc(N2CCC3(O)C(=O)c4ccncc4N=C23)cc1] | 1-[4-(aminomethyl)phenyl]-3a-hydroxy-1H,2H,3H,3aH,4H-pyrrolo[2,3-b]1,7-naphthyridin-4-one | CH | N | CH | CH | — | — | — | 4-(aminomethyl)phenyl |
| 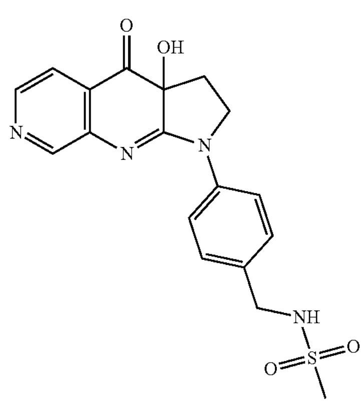 [SMILES: CS(=O)(=O)NCc1ccc(N2CCC3(O)C(=O)c4ccncc4N=C23)cc1] | N-[(4-{3a-hydroxy-4-oxo-1H,2H,3H,3aH,4H-pyrrolo[2,3-b]1,7-naphthyridin-1-yl}phenyl)methyl]methanesulfonamide | CH | N | CH | CH | — | — | — | 4-(methanesulfonamidomethyl)phenyl |

-continued

| Structure | IUPAC name | Q1 | Q2 | Q3 | Q4 | Q5 | Q6 | Q7 | R1 |
|---|---|---|---|---|---|---|---|---|---|
| 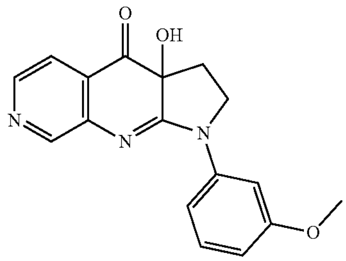 [SMILES: COc1cccc(N2CCC3(O)C(=O)c4ccncc4N=C23)c1] | 3a-hydroxy-1-(3-methoxyphenyl)-1H,2H,3H,3aH,4H-pyrrolo[2,3-b]1,7-naphthyridin-4-one | CH | N | CH | CH | — | — | — | 3-methoxy-phenyl |
| 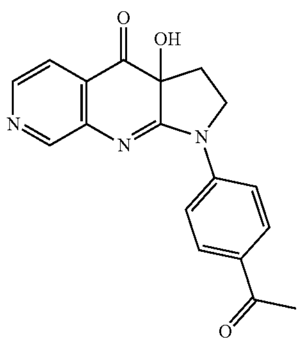 [SMILES: CC(=O)c1ccc(N2CCC3(O)C(=O)c4ccncc4N=C23)cc1] | 1-(4-acetylphenyl)-3a-hydroxy-1H,2H,3H,3aH,4H-pyrrolo[2,3-b]1,7-naphthyridin-4-one | CH | N | CH | CH | — | — | — | 4-acetyl-phenyl |
| 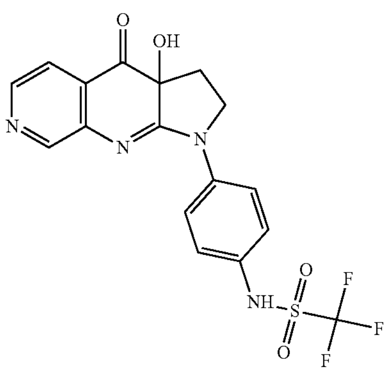 [SMILES: O=C1c2ccncc2N=C2N(c3ccc(NS(=O)(=O)C(F)(F)F)cc3)CCC12O] | N-(4-{3a-hydroxy-4-oxo-1H,2H,3H,3aH,4H-pyrrolo[2,3-b]1,7-naphthyridin-1-yl}phenyl)-1,1,1-trifluoromethanesulfonamide | CH | N | CH | CH | — | — | — | 4-(trifluoro-methan-sulfonyl-amino)phenyl |
| 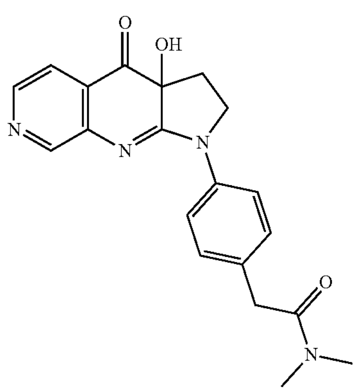 [SMILES: CN(C)C(=O)Cc1ccc(N2CCC3(O)C(=O)c4ccncc4N=C23)cc1] | 2-(4-{3a-hydroxy-4-oxo-1H,2H,3H,3aH,4H-pyrrolo[2,3-b]1,7-naphthyridin-1-yl}phenyl)-N,N-dimethylacetamide | CH | N | CH | CH | — | — | — | N,N-dimethyl-phenyl-acetamid-4-yl |
| 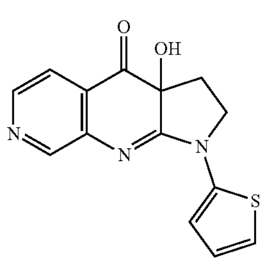 [SMILES: O=C1c2ccncc2N=C2N(c3cccs3)CCC12O] | 3a-hydroxy-1-(thiophen-2-yl)-1H,2H,3H,3aH,4H-pyrrolo[2,3-b]1,7-naphthyridin-4-one | CH | N | CH | CH | — | — | — | thiophen-2-yl |

-continued

| Structure | IUPAC name | Q1 | Q2 | Q3 | Q4 | Q5 | Q6 | Q7 | R1 |
|---|---|---|---|---|---|---|---|---|---|
| 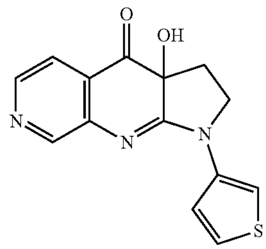 [SMILES: O=C1c2ccncc2N=C2N(c3ccsc3)CCC12O] | 3a-hydroxy-1-(thiophen-3-yl)-1H,2H,3H,3aH,4H-pyrrolo[2,3-b]1,7-naphthyridin-4-one | CH | N | CH | CH | — | — | — | thiophen-3-yl |
| | N-(4-{3a-hydroxy-4-oxo-1H,2H,3H,3aH,4H-pyrrolo[2,3-b]1,7-naphthyridin-1-yl}phenyl)methanesulfonamide | CH | N | CH | CH | — | — | — | 4-(methanesulfonylamino)phenyl |
| 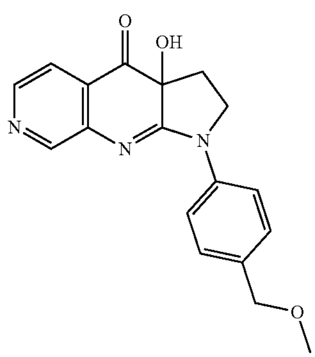 [SMILES: COCc1ccc(N2CCC3(O)C(=O)c4ccncc4N=C23)cc1] | 3a-hydroxy-1-[4-(methoxymethyl)phenyl]-1H,2H,3H,3aH,4H-pyrrolo[2,3-b]1,7-naphthyridin-4-one | CH | N | CH | CH | — | — | — | 4-(methoxymethyl)phenyl |
| 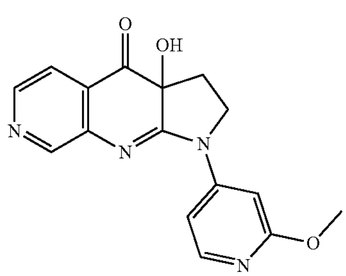 [SMILES: COc1cc(N2CCC3(O)C(=O)c4ccncc4N=C23)ccn1] | 3a-hydroxy-1-(2-methoxypyridin-4-yl)-1H,2H,3H,3aH,4H-pyrrolo[2,3-b]1,7-naphthyridin-4-one | CH | N | CH | CH | — | — | — | 2-methoxypyridin-4-yl |
| 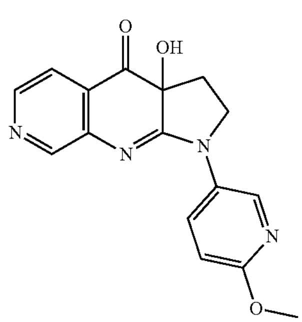 [SMILES: COc1ccc(N2CCC3(O)C(=O)c4ccncc4N=C23)cn1] | 3a-hydroxy-1-(6-methoxypyridin-3-yl)-1H,2H,3H,3aH,4H-pyrrolo[2,3-b]1,7-naphthyridin-4-one | CH | N | CH | CH | — | — | — | 6-methoxypyridin-3-yl |

-continued

| Structure | IUPAC name | Q1 | Q2 | Q3 | Q4 | Q5 | Q6 | Q7 | R1 |
|---|---|---|---|---|---|---|---|---|---|
| | 9-hydroxy-12-[4-(1,4-oxazepan-4-yl)phenyl]-4-thia-2,12-diazatricyclo[7.3.0.0³,⁷]dodeca-1,3(7),5-trien-8-one | — | — | — | — | S | CH | CH | 4-(1,4-oxazepan-4-yl)phenyl |
| | 9-hydroxy-12-[4-(oxan-4-yl)phenyl]-4-thia-2,12-diazatricyclo[7.3.0.0³,⁷]dodeca-1,3(7),5-trien-8-one | — | — | — | — | S | CH | CH | 4-(oxan-4-yl)phenyl |
| | 9-hydroxy-12-[4-(tiomorpholin-4-yl)phenyl]-4-thia-2,12-diazatricyclo[7.3.0.0³,⁷]dodeca-1,3(7),5-trien-8-one | — | — | — | — | S | CH | CH | 4-(thiomorpholin-4-yl)phenyl |
| | 4-(4-{9-hydroxy-8-oxo-4-thia-2,12-diazatricyclo[7.3.0.0³,⁷]dodeca-1,3(7),5-trien-12-yl}phenyl)-1λ⁶-thiomorpholin-1,1-dione | — | — | — | — | S | CH | CH | 4-(thiomorpholin-1,1-dione-4-yl)phenyl |

-continued

| Structure | IUPAC name | Q1 | Q2 | Q3 | Q4 | Q5 | Q6 | Q7 | R1 |
|---|---|---|---|---|---|---|---|---|---|
| | 4-(4-{9-hydroxy-8-oxo-4-thia-2,12-diazatricyclo[7.3.0.0³,⁷]dodeca-1,3(7),5-trien-12-yl}phenyl)-1λ⁶-thian-1,1-dione | — | — | — | — | S | CH | CH | 4-(thian-1,1-dione-4-yl)phenyl |
| | 9-hydroxy-12-[4-(1-methylpiperidin-4-yl)phenyl]-4-thia-2,12-diazatricyclo[7.3.0.0³,⁷]dodeca-1,3(7),5-trien-8-one | — | — | — | — | S | CH | CH | 4-(1-methyl-piperidin-4-yl)phenyl |
| | 9-hydroxy-12-[4-(thian-4-yl)phenyl]-4-thia-2,12-diaza-tricyclo[7.3.0.03,7]dodeca-1,3(7),5-trien-8-one | — | — | — | — | S | CH | CH | 4-(thian-4-yl)phenyl |

-continued

| Structure | IUPAC name | Q1 | Q2 | Q3 | Q4 | Q5 | Q6 | Q7 | R1 |
|---|---|---|---|---|---|---|---|---|---|
| | 9-hydroxy-12-[4-(oxepan-4-yl)phenyl]-4-thia-2,12-diazatricyclo[7.3.0.0³,⁷]dodeca-1,3(7),5-trien-8-one | — | — | — | — | S | CH | CH | 4-(oxepan-4-yl)phenyl |
| 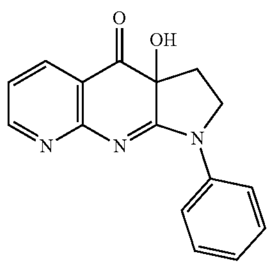 [SMILES: O=C1c2cccnc2N=C2N(c3ccccc3)CCC12O] | 3a-hydroxy-1-phenyl-1H,2H,3H,3aH,4H-pyrrolo[2,3-b]1,8-naphthyridin-4-one | N | CH | CH | CH | — | — | — | phenyl |
| 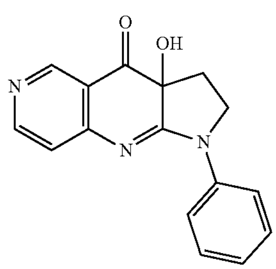 [SMILES: O=C1c2cnccc2N=C2N(c3ccccc3)CCC12O] | 3a-hydroxy-1-phenyl-1H,2H,3H,3aH,4H-pyrrolo[2,3-b]1,6-naftiridin-4-one | CH | CH | N | CH | — | — | — | phenyl |
| 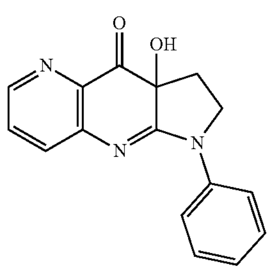 [SMILES: O=C1c2ncccc2N=C2N(c3ccccc3)CCC12O] | 8a-hydroxy-6-phenyl-6H,7H,8H,8aH,9H-pyrrolo[2,3-b]1,5-naphthyridin-9-on | CH | CH | CH | N | — | — | — | phenyl |
| | 9-hydroxy-4-methyl-12-phenyl-2,4,5,12-tetraazatricyclo[7.3.0.0³,⁷]dodeka-1,3(7),5-trien-8-on | — | — | — | — | NMe | N | CH | phenyl |

-continued

| Structure | IUPAC name | Q1 | Q2 | Q3 | Q4 | Q5 | Q6 | Q7 | R1 |
|---|---|---|---|---|---|---|---|---|---|
| (structure) | 7-hydroxy-4-phenyl-11-thia-2,4-diazatricyclo[7.3.0.0³,⁷]dodeka-1(12),2,9-trien-8-on | — | — | — | — | CH | S | CH | phenyl |

INDUSTRIAL APPLICABILITY

The compounds of the invention may be used as medicaments for the indications described above.

What is claimed is:

1. A compound of formula (I) or (II), or a pharmaceutically acceptable salt, tautomer, or stereoisomer thereof:

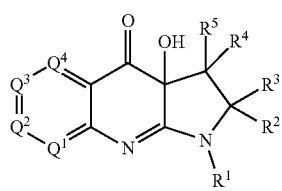
(I)

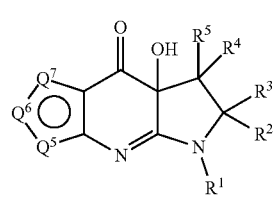
(II)

wherein:

$Q^1$, $Q^2$, $Q^3$ and $Q^4$ are each independently selected from the group consisting of N and CH, wherein at least one of $Q^1$, $Q^2$, $Q^3$ and $Q^4$ is N;

$Q^5$, $Q^6$, and $Q^7$ are each independently selected from the group consisting of S, O, N, $NR^{20}$, and $CR^{20}$, provided that the aromatic nature of the ring is retained and wherein at least one of $Q^5$, $Q^6$ and $Q^7$ is S, O, N, or $NR^{20}$, $R^{20}$ is H, C1-C6 alkyl, or haloalkyl;

$R^2$, $R^3$, $R^4$, and $R^5$ are individually selected from the group consisting of H, halogen, and C1-C6 alkyl;

$R^1$ is H or a 5-, 6-, or 7-membered, saturated, partially saturated, unsaturated, or aromatic heterocyclic group containing one or more N, O, S atoms, and which may be substituted by one or more groups selected from:

C1-C12 straight chain alkyl;
C3-C12 branched chain alkyl;
C3-C12 cycloalkyl;
C2-12 straight chain alkenyl;
C3-C12 branched chain alkenyl;
C2-C12 straight chain alkynyl;
C3-C12 branched chain alkynyl;
—OH;
C1-C12 hydroxyalkyl;
C3-C12 hydroxycycloalkyl;
$NH_2$;
C1-C12 alkylamino, C3-C12 cycloalkylamino, C1-C12 dialkylamino, wherein the amino group may be acylated with a C1-C6 straight chain carboxylic acid, a cyclic carboxylic acid, or an aromatic carboxylic acid, or sulfonylated with C1-C6 straight chain sulfonic acid, a cyclic sulfonic acid, or an aromatic sulfonic acid;
—$NO_2$;
—CN;
C1-C12 alkylcyano;
C3-C12 cycloalkylcyano;
C1-C12 saturated carboxylic acid;
C1-C12 unsaturated carboxylic acid;
aromatic carboxylic acid;
C1-12 carboxylic acid amide formed with a saturated amine, unsaturated amine, or arylamine, wherein the carboxylic acid amide is a group according to formula —C(O)$NH_2$, —C(O)$NHR^{11}$ or —C(O)$NR^{11}R^{12}$;
C1-C12 alkoxy, C2-C12 alkenyloxy, C3-C12 alkynyloxy or C1-C12 alkoxyalkyl, wherein the alkyl, alkenyl, alkynyl, and alkoxy groups may be substituted by one or more halogen atoms;
F, Cl, Br, or I;
C1-C12 carboxylic acid ester formed with a saturated alcohol, unsaturated alcohol, or aryl alcohol;
C1-C12 alkylthio, C3-C12 cycloalkylthio, C2-C12 alkenylthio, C2-C12 alkynylthio or alkylthioalkyl, wherein the alkyl, cycloalkyl, alkenyl and alkynyl groups may be substituted with one or more halogen;
methanesulfonylaminomethyl;
trifluoromethanesulfonylamino;
N,N-dimethylaminocarbonylmethyl[$CH_2$—CO—N($CH_3$)$_2$];
acetyl; and
methanesulfonylamino;

$R^{11}$ and $R^{12}$ are each independently C1-C6 straight chain alkyl, C1-C6 branched chain alkyl, C3-C12 cycloalkyl, C2-$C_6$ alkenyl, or C6-C12 aryl, or R¹ is:

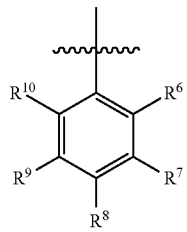

R⁶ and R¹⁰ are H:
R⁷, R⁸, and R⁹ are each independently:
  H;
  a 5-, 6-, or 7-membered, saturated, partially saturated, unsaturated or aromatic heterocyclic group containing one or more N, O, S atoms, and which may be substituted by one or more groups selected from the group consisting of:
    C1-C12 straight chain alkyl;
    C3-C12 branched chain alkyl;
    C3-C12 cycloalkyl;
    C2-12 straight chain alkenyl;
    C3-C12 branched chain alkenyl;
    C2-C12 straight chain alkynyl;
    C3-C12 branched chain alkynyl;
    —OH;
    C1-C12 hydroxyalkyl;
    C3-C12 hydroxycycloalkyl;
    NH₂;
    C1-C12 alkylamino, C3-C12 cycloalkylamino or C1-C12 dialkylamino, wherein the amino group may be acylated with a C1-C6 straight chain carboxylic acid, a cyclic carboxylic acid, or an aromatic carboxylic acid, or sulfonylated with C1-C6 straight chain sulfonic acid, a cyclic sulfonic acid, or an aromatic sulfonic acid;
    —NO₂;
    —CN;
    C1-C12 alkylcyano;
    C3-C12 cycloalkylcyano;
    C1-C12 saturated carboxylic acid;
    C1-C12 unsaturated carboxylic acid;
    aromatic carboxylic acid;
    C1-12 carboxylic acid amide formed with a saturated amine, unsaturated amine, or arylamine, wherein the carboxylic acid amide is a group according to formula —C(O)NH₂, —C(O)NHR¹¹, or —C(O)NR¹¹R¹²;
    C1-C12 alkoxy, C2-C12 alkenyloxy, C3-C12 alkynyloxy or C1-C12 alkoxyalkyl, wherein the alkyl, alkenyl, alkynyl, and alkoxy groups may be substituted by one or more halogen atoms;
    F, Cl, Br, or I;
    C1-C12 carboxylic acid ester formed with a saturated alcohol, unsaturated alcohol, or aryl alcohol;
    C1-C12 alkylthio, C3-C12 cycloalkylthio, C2-C12 alkenylthio, C2-C12 alkynylthio or alkylthioalkyl, wherein the alkyl, cycloalkyl, alkenyl and alkynyl groups may be substituted with one or more halogen;
    methanesulfonylaminomethyl;
    trifluoromethanesulfonylamino;
    N,N-dimethylaminocarbonylmethyl [CH₂—CO—N(CH₃)₂];
    acetyl; and
    methanesulfonylamino; or
  any group selected from the group consisting of:
    C1-C12 straight chain alkyl;
    C3-C12 branched chain alkyl;
    C3-C12 cycloalkyl;
    C2-12 straight chain alkenyl;
    C3-C12 branched chain alkenyl;
    C2-C12 straight chain alkynyl;
    C3-C12 branched chain alkynyl;
    C1-C12 hydroxyalkyl;
    C3-C12 hydroxycycloalkyl;
    C3-C12 cycloalkylamino or C1-C12 dialkylamino;
    —NO₂;
    —CN;
    C1-C12 alkylcyano;
    C3-C12 cycloalkylcyano;
    aromatic carboxylic acid;
    C1-12 carboxylic acid amide formed with a saturated amine, unsaturated amine, or arylamine, wherein the carboxylic acid amide is a group according to formula —C(O)NH₂, —C(O)NHR¹¹, or —C(O)NR¹¹R¹²;
    C1-C12 alkoxy, C2-C12 alkenyloxy, C3-C12 alkynyloxy or C1-C12 alkoxyalkyl, wherein the alkyl, alkenyl, alkynyl, and alkoxy groups may be substituted by one or more halogen atoms;
    F, Cl, Br, or I;
    C1-C12 carboxylic acid ester formed with a saturated alcohol, unsaturated alcohol, or aryl alcohol;
    C1-C12 alkylthio, C3-C12 cycloalkylthio, C2-C12 alkenylthio, C2-C12 alkynylthio or alkylthioalkyl, wherein the alkyl, cycloalkyl, alkenyl and alkynyl groups may be substituted with one or more halogen;
    methanesulfonylaminomethyl;
    trifluoromethanesulfonylamino;
    N,N-dimethylaminocarbonylmethyl [CH₂—CO—N(CH₃)₂];
    acetyl; and
    methanesulfonylamino.

2. The compound of claim 1, or a pharmaceutically acceptable salt, tautomer, or stereoisomer thereof, wherein:
R¹ is H, 3-pyridyl, 4-pyridyl, 2-thienyl, 3-thienyl, 2-methoxy-4-pyridyl, 6-methoxy pyridyl, or

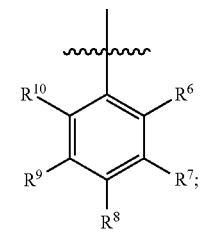

R², R³, R⁴, and R⁵ are H;
R⁷, R⁸, and R⁹ are independently H, morpholinyl, —NO₂, —CN, —CONH₂, —OCH₃, trifluoromethyl, F, trifluoromethoxy, dimethylamino, hydroxymethyl, cyanomethyl, aminomethyl, methanesulfonylaminomethyl, trifluoromethanesulfonylamino, —CH₂—CO—N(CH₃)₂, acetyl, methanesulfonylamino, methoxymethyl, 1,4-oxazepan-4-yl, oxan-4-yl, tetrahydrothiopyran-4-yl, 1,1-dioxo-tetrahydrothiopyran-4-yl, thiomorpholin-4-yl, 1,1-dioxothiomorpholin-4-yl, tetrahydropyran-4-yl, or 1-methyl piperidin-4-yl;

one of $Q^1$, $Q^2$, $Q^3$, and $Q^4$ is N and the others are CH; and $Q^5$ is S and $Q^6$ and $Q^7$ are CH; or $Q^7$ is S and $Q^5$ and $Q^6$ is CH; or $Q^5$ is N—$CH_3$ and $Q^6$ is N and $Q^7$ is CH; or $Q^5$ is S and $Q^6$ is C—$CH_3$ and $Q^7$ is CH.

3. The compound of claim 1, or a pharmaceutically acceptable salt, tautomer, or stereoisomer thereof, wherein:
$R^1$ is H, 3-pyridyl, 4-pyridyl, 2-thienyl, 3-thienyl, 2-methoxy-4-pyridyl, 6-methoxy-3-pyridyl, or

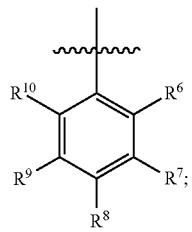

$R^2$, $R^3$, $R^4$, and $R^5$ are H;
$R^7$ and $R^9$ are selected from the group consisting of H, —CN, and —$OCH_3$;
$R^8$ is selected from the group consisting of H, morpholinyl, —$NO_2$, —CN, —$CONH_2$, —$OCH_3$, trifluoromethyl, F, trifluoromethoxy, dimethylamino, hydroxymethyl, cyanomethyl, aminomethyl, methanesulfonylaminomethyl, trifluoromethanesulfonylamino, —$CH_2$—CO—$N(CH_3)_2$, acetyl, methanesulfonylamino, methoxymethyl, 1,4-oxazepan-4-yl, oxan-4-yl, tetrahydrothiopyran-4-yl, 1,1-dioxo-tetrahydrothiopyran-4-yl, thiomorpholin-4-yl, 1,1-dioxothiomorpholin-4-yl, tetrahydropyran-4-yl, and 1-methylpiperidin-4-yl;
one of $Q^1$, $Q^2$, $Q^3$, and $Q^4$ is N and the others are CH; and $Q^5$ is S and $Q^6$ and $Q^7$ are CH; or $Q^7$ is S and $Q^5$ and $Q^6$ are CH; or $Q^5$ is N—$CH_3$ and $Q^6$ is N and $Q^7$ is CH; or $Q^5$ is S and $Q^6$ is C—$CH_3$ and $Q^7$ is CH.

4. The compound of claim 1, or a pharmaceutically acceptable salt, tautomer, or stereoisomer thereof, wherein: $R^2$, $R^3$, $R^4$, $R^5$, $R^7$, and $R^9$ are H; and $R^8$ is morpholinyl;
one of $Q^1$, $Q^2$, $Q^3$, and $Q^4$ is N and the others are CH; and wherein $Q^5$ is S and $Q^6$ and $Q^7$ are CH; or $Q^7$ is S and $Q^5$ and $Q^6$ are CH; or $Q^5$ is N—$CH_3$ and $Q^6$ is N and $Q^7$ is CH.

5. A compound which is:
3a-hydroxy-1-phenyl-1H,2H,3H,3aH,4H-pyrrolo[2,3-b]1,7-naphthyridin-4-one,
9-hydroxy-12-phenyl-4-thia-2,12-diazatricyclo[7.3.0.0$^{3,7}$]dodeca-1,3(7),5-trien-8-one,
7-hydroxy-4-phenyl-10-thia-2,4-diazatricyclo[7.3.0.0$^{3,7}$]dodeca-1(9),-2,11-trien-8-one,
9-hydroxy-12-[4-(morpholin-4-yl)phenyl]-4-thia-2,12-diazatricyclo[7.3.0.0$^{3,7}$]dodeca-1,3(7),5-trien-8-one,
3α-hydroxy-1-phenyl-1H,2H,3H,3aH,4H-pyrrolo[2,3-b]1,8-naphthyridin-4-one,
8a-hydroxy-6-phenyl-6H,7H,8H,8aH,9H-pyrrolo[2,3-b]1,5-naphthyridin-9-one,
9-hydroxy-5-methyl-12-phenyl-4-thia-2,12-diazatricyclo[7.3.0.0$^{3,7}$]dodeca-1,3(7),5-trien-8-one,
12-phenyl-9-hydroxy-6-methyl-4-thia-2,5,12-triazatricyclo[7.3.0.0$^{3,7}$]dodeca-1,3(7),5-trien-8-one,
(9S)-9-hydroxy-4-thia-2,12-diazatricyclo[7.3.0.0$^{3,7}$]dodeca-1,3(7),5-trien-8-one,
(9S)-9-hydroxy-5-methyl-12-(thiophen-2-yl)-4-thia-2,12-diazatricyclo[7.3.0.0$^{3,7}$]dodeca-1,3(7),5-trien-8-one,
(9S)-9-hydroxy-12-(4-methoxyphenyl)-4-thia-2,12-diazatricyclo[7.3.0.0$^{3,7}$]dodeca-1,3(7),5-trien-8-one,
(9S)-9-hydroxy-12-[4-(trifluoromethoxy)phenyl]-4-thia-2,12-diazatricyclo[-7.3.0.0$^{3,7}$]dodeca-1,3(7),5-trien-8-one,
(9S)-4-{9-hydroxy-8-oxo-4-thia-2,12-diazatricyclo[7.3.0.0$^{3,7}$]dodeca-1,3(7),5-trien-12-yl}benzonitrile,
(9S)-12-(4-acetylphenyl)-9-hydroxy-4-thia-2,12-diazatricyclo[7.3.0.0$^{3,7}$]dodeca-1,3(7),5-trien-8-one,
(9S)-2-(4-{9-hydroxy-8-oxo-4-thia-2,12-diazatricyclo[7.3.0.0$^{3,7}$]dodeca-1,3(7),5-trien-12-yl}phenyl)acetonitrile,
(9S)-9-hydroxy-12-[4-(hydroxymethyl)phenyl]-4-thia-2,12-diazatricyclo[7.3.0.0$^{3,7}$]dodeca-1,3(7),5-trien-8-one,
(9S)-9-hydroxy-12-(thiophen-2-yl)-4-thia-2,12-diazatricyclo[7.3.0.0$^{3,7}$]dodeca-1,3(7),5-trien-8-one,
(9S)-9-hydroxy-12-(6-methoxypyridin-3-yl)-4-thia-2,12-diazatricyclo[7.3.0.0$^{3,7}$]dodeca-1,3(7),5-trien-8-one,
9-hydroxy-5-methyl-12-[4-(morpholin-4-yl)phenyl]-4-thia-2,12-diazatricyclo[7.3.0.0$^{3,7}$]dodeca-1,3(7),5-trien-8-one,
9-hydroxy-12-(4-methoxyphenyl)-5-methyl-4-thia-2,12-diazatricyclo[7.3.0.0$^{3,7}$]dodeca-1,3(7),5-trien-8-one,
9-hydroxy-5-methyl-12-[4-(trifluoromethoxy)phenyl]-4-thia-2,12-diazatricyclo[7.3.0.0$^{3,7}$]dodeca-1,3(7),5-trien-8-one,
4-{9-hydroxy-5-methyl-8-oxo-4-thia-2,12-diazatricyclo[7.3.0.0$^{3,7}$]dodeca-1,3(7),5-trien-12-yl}benzonitrile,
12-(4-acetylphenyl)-9-hydroxy-5-methyl-4-thia-2,12-diazatricyclo[7.3.0.0$^{3,7}$]dodeca-1,3(7),5-trien-8-one,
2-(4-{9-hydroxy-5-methyl-8-oxo-4-thia-2,12-diazatricyclo[7.3.0.0$^{3,7}$]-dodeca-1,3(7),5-trien-12-yl}phenyl)acetonitrile,
9-hydroxy-12-[4-(hydroxymethyl)phenyl]-5-methyl-4-thia-2,12-diazatricyclo-[7.3.0.0$^{3,7}$]dodeca-1,3(7),5-trien-8-one,
9-hydroxy-5-methyl-12-(thiophen-2-yl)-4-thia-2,12-diazatricyclo[7.3.0.0$^{3,7}$]dodeca-1,3(7),5-trien-8-one,
9-hydroxy-12-(6-methoxypyridin-3-yl)-5-methyl-4-thia-2,12-diazatricyclo[7.3.0.0$^{3,7}$]dodeca-1,3(7),5-trien-8-one,
9-hydroxy-5-methyl-4-thia-2,12-diazatricyclo[7.3.0.0$^{3,7}$]dodeca-1,3(7),5-trien-8-one,
(9S)-9-hydroxy-12-(4-methylphenyl)-4-thia-2,12-diazatricyclo[7.3.0.0$^{3,7}$]dodeca-1,3(7),5-trien-8-one,
12-[4-(methyl)phenyl]-9-hydroxy-5-methyl-4-thia-2,12-diazatricyclo[7.3.0.0$^{3,7}$]dodeca-1,3(7),5-trien-8-one,
3a-hydroxy-1-[4-(trifluoromethoxy)phenyl]-1H,2H,3H,3aH,4H-pyrrolo[2,3-b]1, naphthyridin-4-one,
1-(4-acetylphenyl)-3α-hydroxy-1H,2H,3H,3aH,4H-pyrrolo[2,3-b]1,7-naphthyridin-4-one,
1-[4-(methyl)phenyl]-3α-hydroxy-1H,2H,3H,3aH,4H-pyrrolo[2,3-b]1,-7-naphthyridin-4-one,
3a-hydroxy-1-[4-(morpholin-4-yl)phenyl]-1H,2H,3H,3aH,4H-pyrrolo[2,3-b]1,7-naphthyridin-4-one,
(9S)-12-[4-(dimethylamino)phenyl]-9-hydroxy-4-thia-2,12-diazatricyclo[7.3.0.0$^{3,7}$]dodeca-1,3(7),5-trien-8-one,
12-[4-(dimethylamino)phenyl]-9-hydroxy-5-methyl-4-thia-2,12-diazatricyclo-[7.3.0.0$^{3,7}$]dodeca-1,3(7),5-trien-8-one, 1-[4-(dimethylamino)phenyl]-3α-hydroxy-1H,2H,3H, 3aH,4H-pyrrolo[2,3-b]1,7-naphthyridin-4-one,
3a-hydroxy-1H,2H,3H,3aH,4H-pyrrolo[2,3-b]1,7-naphthyridin-4-one,
or a pharmaceutically acceptable salt, tautomer, or stereoisomer thereof.

6. A method of inhibiting a myosin II isoform in a subject, the method comprising administering to the subject the compound of claim 1, or a pharmaceutically acceptable salt, tautomer, or stereoisomer thereof, wherein the myosin II isoform is skeletal muscle myosin II, cardiac muscle myosin II, smooth muscle myosin II, or non-muscle myosin II.

7. A method of treating a condition or disease, the method comprising administering the compound of claim 1, or a pharmaceutically acceptable salt, tautomer, or stereoisomer thereof, to a subject suffering from or exhibiting symptoms of a condition or disease that is non-specific lower-back pain, lumbar spasm, spasmodic spasm, stress-induced occiput spasms, vaginal spasms, prolonged muscle spasm in limbs, epilepsia partialis continua, post-stroke spasticity, muscle spasms in cerebral palsy, muscle spasms in multiple sclerosis, vaginismus, musculoskeletal muscle spasm or drug-induced convulsions.

8. The compound of claim 1, or a pharmaceutically acceptable salt, tautomer, or stereoisomer thereof, wherein:
$R_1$ is H, 3-pyridyl, 2-thienyl, 2-methoxy-4-pyridyl, or

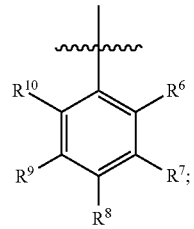

$R^2$, $R^3$, $R^4$, and $R^5$ are H;
$R^6$ and $R^{10}$ are H;
$R^7$, $R^8$, $R^9$ are each independently H, Cl, —$NO_2$, —CN, —$CONH_2$, —$OCH_3$, morpholinyl, ethoxy, propoxy, methyl, trifluoromethyl, trifluoromethoxy, dimethylamino, dipropylamino, cyanomethyl, acetyl, NH acylated with propionic acid, or propionic acid ester;
one of $Q^1$, $Q^2$, $Q^3$, and $Q^4$ is N and the others are CH; and $Q^5$ is S and $Q^6$ and $Q^7$ are CH; or $Q^7$ is S and $Q^5$ and $Q^6$ are CH; or $Q^5$ is N—$CH_3$ and $Q^6$ is N and $Q^7$ is CH; or $Q^5$ is S and $Q^6$ is C—$CH_3$ and $Q^7$ is CH.

9. The compound of claim 1, or a pharmaceutically acceptable salt, tautomer, or stereoisomer thereof, wherein the compound is of formula (I) or a pharmaceutically acceptable salt, tautomer, or stereoisomer thereof.

10. The compound of claim 1, or a pharmaceutically acceptable salt, tautomer, or stereoisomer thereof, wherein the compound is of formula (II), or a pharmaceutically acceptable salt, tautomer, or stereoisomer thereof.

11. The compound of claim 8, or a pharmaceutically acceptable salt, tautomer, or stereoisomer thereof, wherein:
$R^2$, $R^3$, $R^4$, $R^5$, $R^7$, and $R^9$ are H;
$R^8$ is morpholinyl;
one of $Q^1$, $Q^2$, $Q^3$, and $Q^4$ is N and the others are CH; and wherein $Q^5$ is S and $Q^6$ and $Q^7$ are CH; or $Q^7$ is S and $Q^5$ and $Q^6$ are CH; or $Q^5$ is N—$CH_3$ and $Q^6$ is N and $Q^7$ is CH.

12. The compound of claim 1, or a pharmaceutically acceptable salt, tautomer, or stereoisomer thereof, wherein:

one of $Q^1$, $Q^2$, $Q^3$, and $Q^4$ is N and the others are CH;
$Q^5$ is S and $Q^6$ and $Q^7$ are CH; or $Q^5$ is S, $Q^6$ is C—$CH_3$, and $Q^7$ is CH;
$R^2$, $R^3$, $R^4$, and $R^5$ are H;
$R^1$ is a 5-, 6-, or 7-membered, saturated, partially saturated, unsaturated, or aromatic heterocyclic group containing one or more N, O, or S atoms, and which may be substituted by one or more groups selected from the group consisting of C1-12 straight chain alkyl, C3-C12 branched chain alkyl, —OH, C1-12 hydroxyalkyl, —$NH_2$, C1-12 alkylamino, C1-12 dialkylamino, —$NO_2$, —CN, C1-12 alkylcyano, acetyl, and C1-12 alkoxy, wherein the C1-12 alkoxy may be substituted by one or more halogen atoms;
or $R^1$ is:

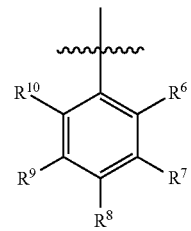

wherein $R^6$ and $R^{10}$ are H; and
$R^7$, $R^8$, and $R^9$ are each independently:
H;
halogen;
a 5-, 6-, or 7-membered, saturated, partially saturated, unsaturated, or aromatic heterocyclic group containing one or more N, O, or S atoms; or
C1-12 straight chain alkyl, C3-C12 branched chain alkyl, C1-12 hydroxyalkyl, C1-12 dialkylamino, —$NO_2$, —CN, C1-12 alkylcyano, acetyl, or C1-12 alkoxy, wherein the C1-12 alkoxy may be substituted by one or more halogen atoms.

13. The compound of claim 12, or a pharmaceutically acceptable salt, tautomer, or stereoisomer thereof, wherein $R^7$ and $R^9$ are H.

14. The compound of claim 12, or a pharmaceutically acceptable salt, tautomer, or stereoisomer thereof, wherein:
$R_1$ is selected from the group consisting of 3-pyridyl, 4-pyridyl, 2-thienyl, 3-thienyl, 2-methoxy-4-pyridyl, and 6-methoxy-3-pyridyl;
or $R^1$ is:

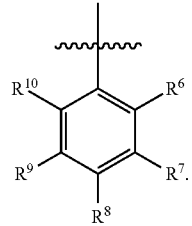

15. The compound of claim 12, or a pharmaceutically acceptable salt, tautomer, or stereoisomer thereof, wherein $R^1$ is:

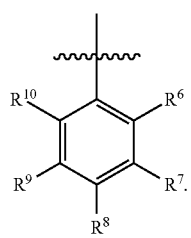

16. The compound of claim 15, or a pharmaceutically acceptable salt, tautomer, or stereoisomer thereof, wherein $R^7$ and $R^9$ are H.

17. The compound of claim 16, or a pharmaceutically acceptable salt, tautomer, or stereoisomer thereof, wherein $R^8$ is a 5-, 6-, or 7-membered, saturated, partially saturated, unsaturated, or aromatic heterocyclic group containing one or more N, O, or S atoms.

18. A compound which is:

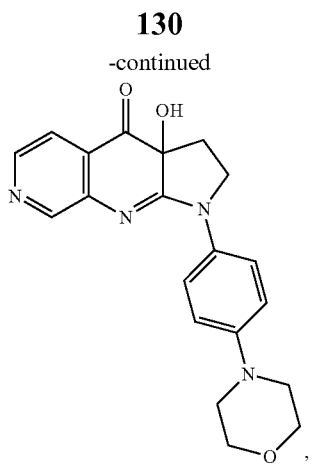

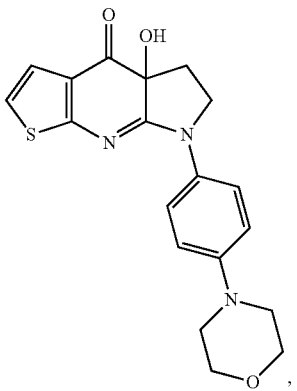

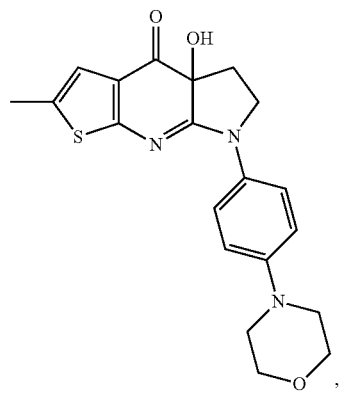

or a pharmaceutically acceptable salt or stereoisomer thereof.

19. The compound of claim 18 which is:

-continued

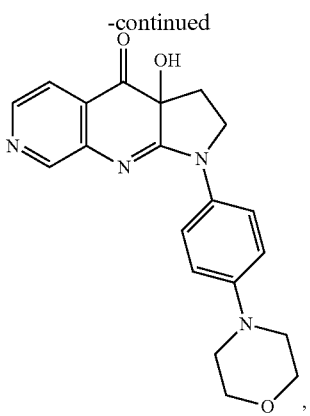

or a pharmaceutically acceptable salt or stereoisomer thereof.

20. A method of treating a condition or disease, the method comprising administering the compound of claim 1, or a pharmaceutically acceptable salt, tautomer, or stereoisomer thereof, to a subject suffering from or exhibiting symptoms of a condition or disease that is cardiomyopathy, or myopathy in myocardial muscle.

21. A method of treating a condition or disease, the method comprising administering the compound of claim 1, or a pharmaceutically acceptable salt, tautomer, or stereoisomer thereof, to a subject suffering from or exhibiting symptoms of muscles spasms, where the muscle spasms are lumbar spasms, spasmodic spasms, stress-induced occiput spasms, prolonged muscle spasms, muscle spasms in cerebral palsy, muscle spasms in multiple sclerosis, vaginal spasms, musculoskeletal muscle spasms, or smooth muscle spasms during labor.

22. A method of treating a condition or disease, the method comprising administering the compound of claim 18, or a pharmaceutically acceptable salt or stereoisomer thereof, to a subject suffering from or exhibiting symptoms of a condition or disease that is non-specific lower-back pain, lumbar spasm, spasmodic spasm, stress-induced occiput spasms, prolonged muscle spasms in limbs, epilepsia partialis continua, post-stroke spasticity, muscle spasms in cerebral palsy, muscle spasms in multiple sclerosis, vaginal spasms, vaginismus, musculoskeletal muscle spasm, or drug-induced convulsions.

23. A method of treating a condition or disease, the method comprising administering the compound of claim 18, or a pharmaceutically acceptable salt or stereoisomer thereof, to a subject suffering from or exhibiting symptoms of muscles spasms, where the muscle spasms are lumbar spasms, spasmodic spasms, stress-induced occiput spasms, prolonged muscle spasms, muscle spasms in cerebral palsy, muscle spasms in multiple sclerosis, vaginal spasms, or musculoskeletal muscle spasms.

\* \* \* \* \*